(12) United States Patent
Arieli et al.

(10) Patent No.: US 7,327,470 B2
(45) Date of Patent: *Feb. 5, 2008

(54) SPATIAL AND SPECTRAL WAVEFRONT ANALYSIS AND MEASUREMENT

(75) Inventors: Yoel Arieli, Jerusalem (IL); Shay Wolfling, Tel Aviv (IL); Eyal Shekel, Jerusalem (IL)

(73) Assignee: Icos Vision Systems N.V., Heverlee (BE)

( * ) Notice: Subject to any disclaimer, the term of this patent is extended or adjusted under 35 U.S.C. 154(b) by 37 days.

This patent is subject to a terminal disclaimer.

(21) Appl. No.: 10/988,361

(22) Filed: Nov. 12, 2004

(65) Prior Publication Data

US 2005/0094157 A1    May 5, 2005

Related U.S. Application Data

(63) Continuation of application No. 09/829,435, filed on Apr. 9, 2001, now Pat. No. 6,819,435.

(60) Provisional application No. 60/196,862, filed on Apr. 12, 2000.

(51) Int. Cl.
    *G01B 9/02* (2006.01)

(52) U.S. Cl. ..................................... 356/512

(58) Field of Classification Search .............. 356/521, 356/512–515, 499, 494, 488
See application file for complete search history.

(56) References Cited

U.S. PATENT DOCUMENTS

| | | | |
|---|---|---|---|
| 3,694,088 A | 9/1972 | Gallagher et al. | |
| 4,190,366 A | 2/1980 | Doyle | 356/346 |
| 4,407,569 A | 10/1983 | Piller et al. | 350/509 |
| 4,624,569 A | 11/1986 | Kwon | |
| 4,653,921 A | 3/1987 | Kwon | |
| 4,867,565 A | 9/1989 | Lequime | |
| 5,159,474 A | 10/1992 | Franke et al. | |
| 5,235,587 A | 8/1993 | Bearden et al. | 369/106 |
| 5,446,540 A | 8/1995 | Lin | 356/345 |
| 5,471,303 A | 11/1995 | Ai et al. | 356/357 |
| 5,600,440 A | 2/1997 | Bendall | 356/345 |
| 5,619,372 A | 4/1997 | Hellmuth et al. | 359/389 |
| 5,751,475 A | 5/1998 | Ishiwata et al. | 359/387 |

(Continued)

FOREIGN PATENT DOCUMENTS

| | | |
|---|---|---|
| EP | 0 555 099 | 8/1993 |
| GB | 2 315 700 | 2/1998 |
| JP | 6186504 | 7/1994 |
| JP | 7225341 | 8/1995 |
| JP | 7261089 | 10/1995 |
| JP | 8094936 | 4/1996 |
| JP | 9179029 | 7/1997 |
| JP | 9230247 | 9/1997 |

OTHER PUBLICATIONS

Phillion D.W. "General Methods for Generating Phase-Shifting Interferometry Algorithms", Applied Optics, vol. 36, 8098 (1997).

(Continued)

*Primary Examiner*—Hwa (Andrew) Lee
(74) *Attorney, Agent, or Firm*—Ladas & Parry LLP

(57) ABSTRACT

A method and apparatus for wavefront analysis including obtaining a plurality of differently phase changed transformed wavefronts corresponding to a wavefront being analyzed which has an amplitude and a phase, obtaining a plurality of intensity maps of the plurality of phase changed transformed wavefronts and employing the plurality of intensity maps to obtain an output indicating the amplitude and phase of the wavefront being analyzed.

6 Claims, 25 Drawing Sheets

U.S. PATENT DOCUMENTS

| | | | |
|---|---|---|---|
| 5,777,736 A | 7/1998 | Horton | |
| 5,814,815 A | 9/1998 | Matsumoto et al. | 250/311 |
| 5,870,191 A | 2/1999 | Shirley et al. | 345/356 |
| 5,936,253 A | 8/1999 | Sugaya | 250/548 |
| 5,969,853 A | 10/1999 | Takaoka | 359/370 |
| 5,969,855 A | 10/1999 | Ishiwata et al. | 359/386 |
| 6,819,435 B2 * | 11/2004 | Arieli et al. | 356/512 |
| 2005/0007603 A1 * | 1/2005 | Arieli et al. | 356/601 |

OTHER PUBLICATIONS

Pluta M., "Stray-Light Problem in Phase Contrast Microscopy or Toward Highly Sensitive Phase Contrast Devices: A review", Optical engineering, vol. 32, 3199 (1993).

Noda T. and Kawata S., "Separation of Phase and Absorption Images in Phase-Contrast Microscopy", Journal of the Optical Society of America A, vol. 9, 924 (1992).

Creath K., "Phase Measurement Interferometry Techniques", Progress in Optics XXVI, 348 (1988).

Greivenkamp J.E. "Generalized Data Reduction for heterodyne Interferometry", Optical Engineering, vol. 23, 350 (1984).

Morgan C.J. "Least-Squares Estimation in Phase-Measurement Interferometry", Optics Letters, vol. 7, 368 (1982).

Golden, L.J. "Zernike Test. 1: Analytical Aspects." *Applied Optics*, vol. 16, (1977) 205.

Bruning, J.H., et al. "Digital Wavefront Measuring Interferometry for Testing Optical Surfaces and Lenses." *Applied Optics*, vol. 13 (1974) 2693.

English Abstract of JP 9230247 dated Sep. 5, 1997.

English Abstract of JP 9179029 dated Jul. 11, 1997.

English Abstract of JP 8094936 dated Apr. 12, 1996.

English Abstract of JP 7261089 dated Oct. 13, 1995.

English Abstract of JP 7225341 dated Aug. 22, 1995.

English Abstract of JP 6186504 dated Jul. 8, 1994.

* cited by examiner

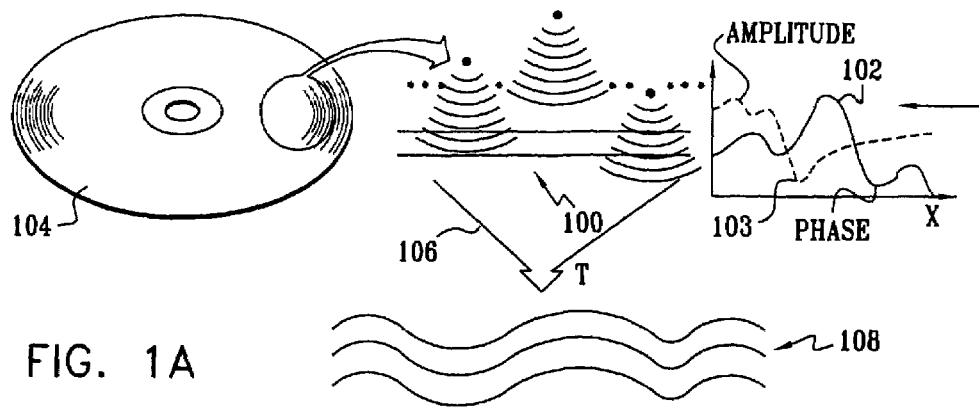
FIG. 1A
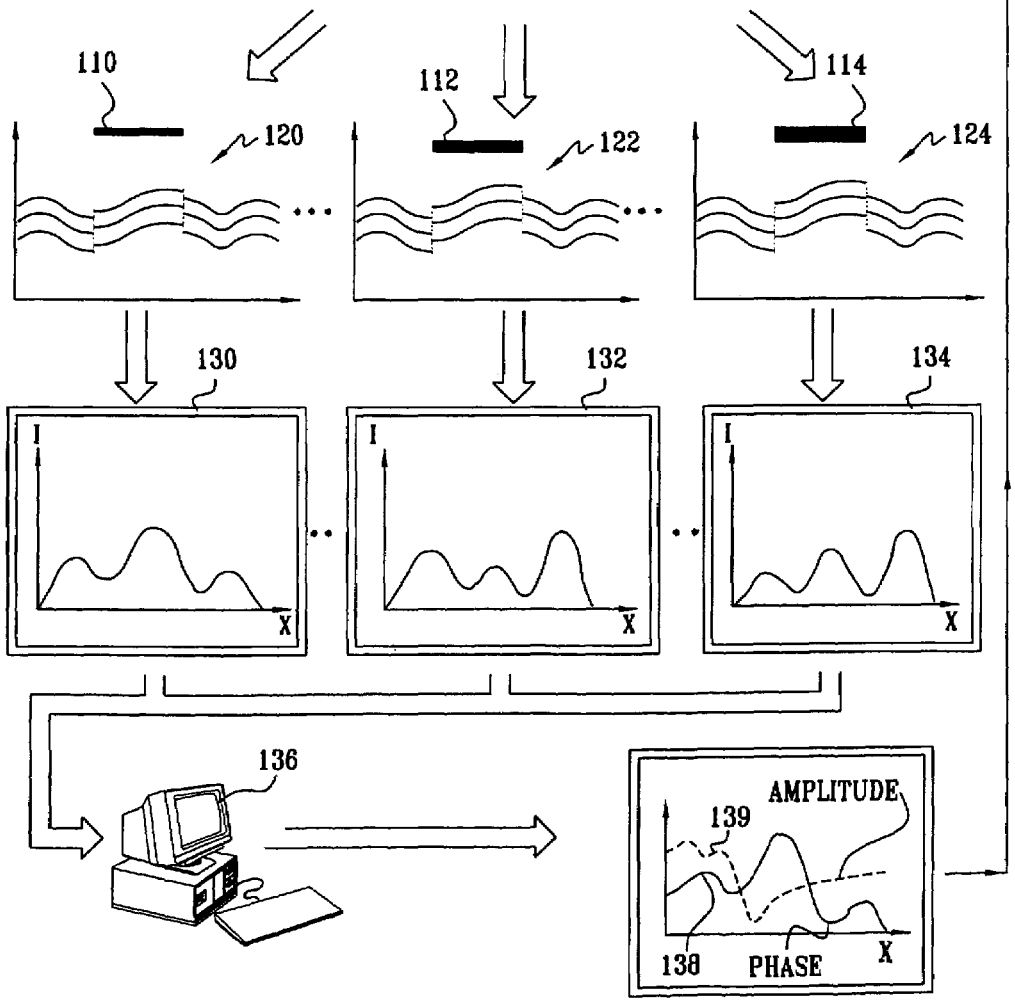

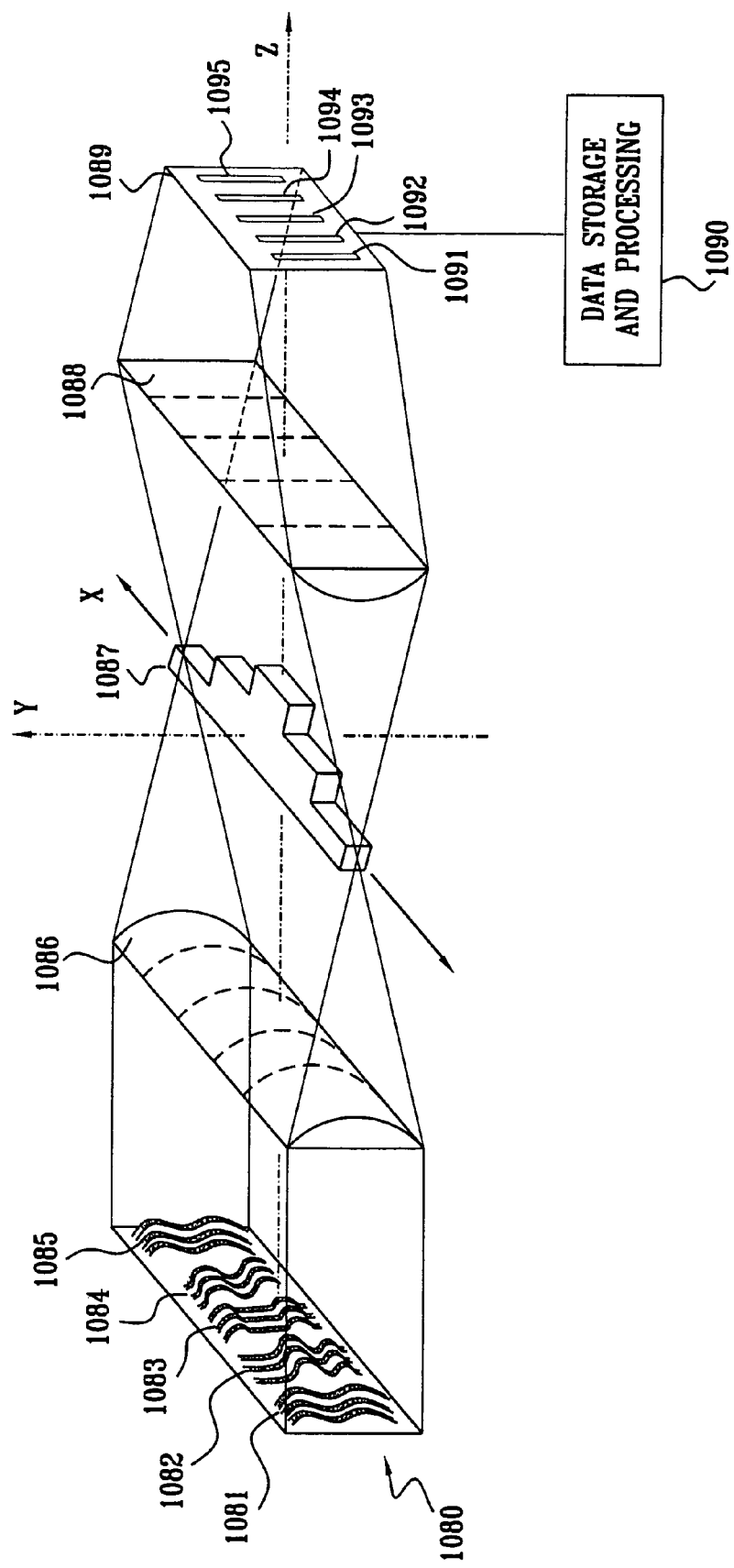

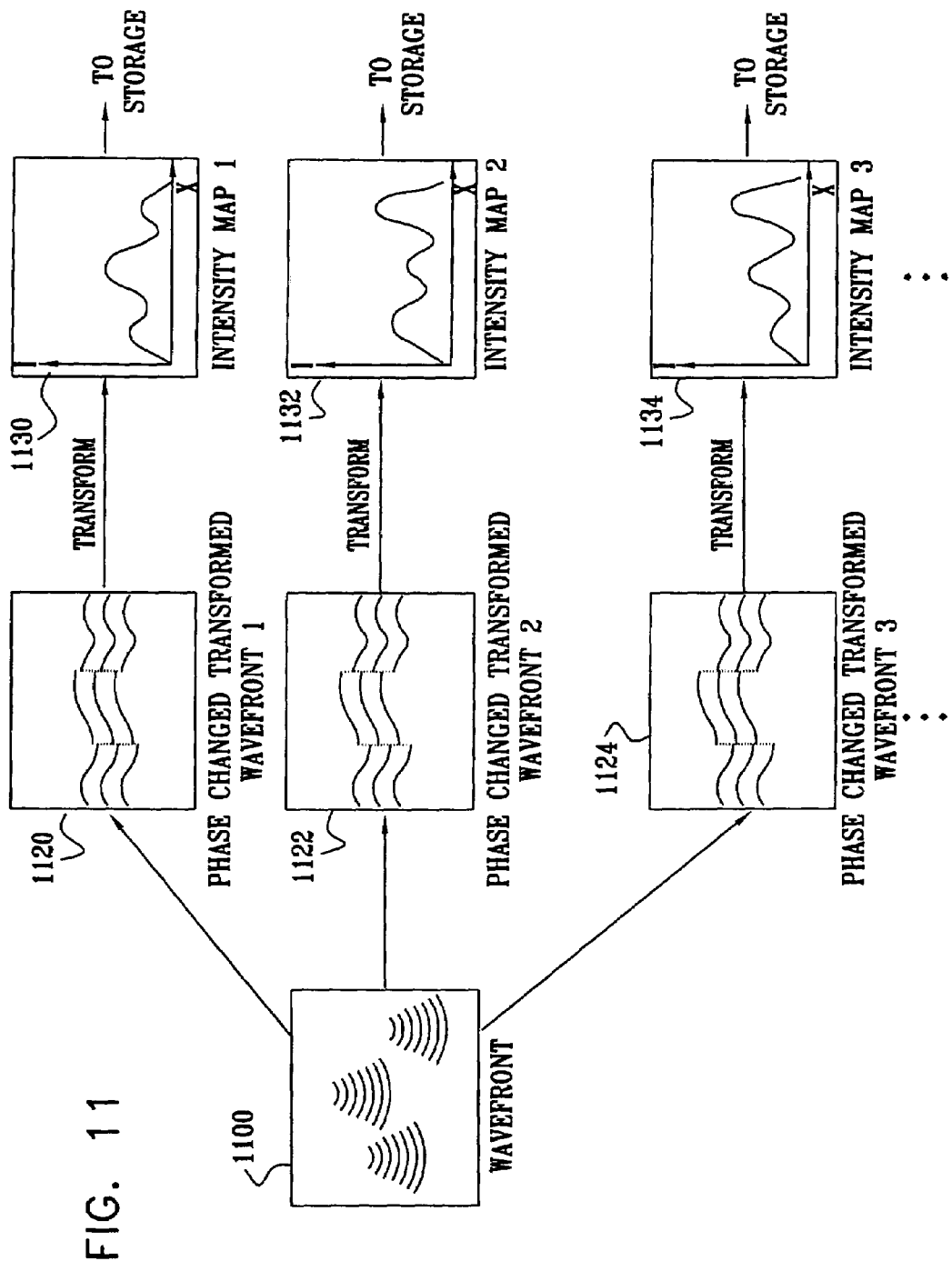

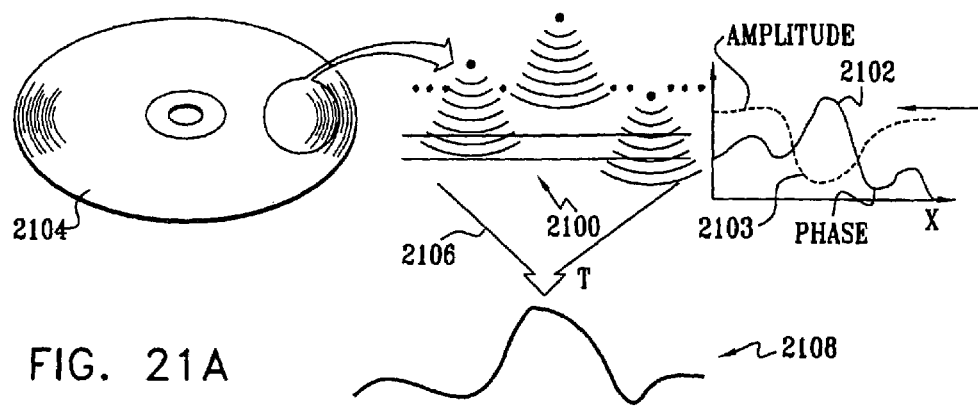
FIG. 21A
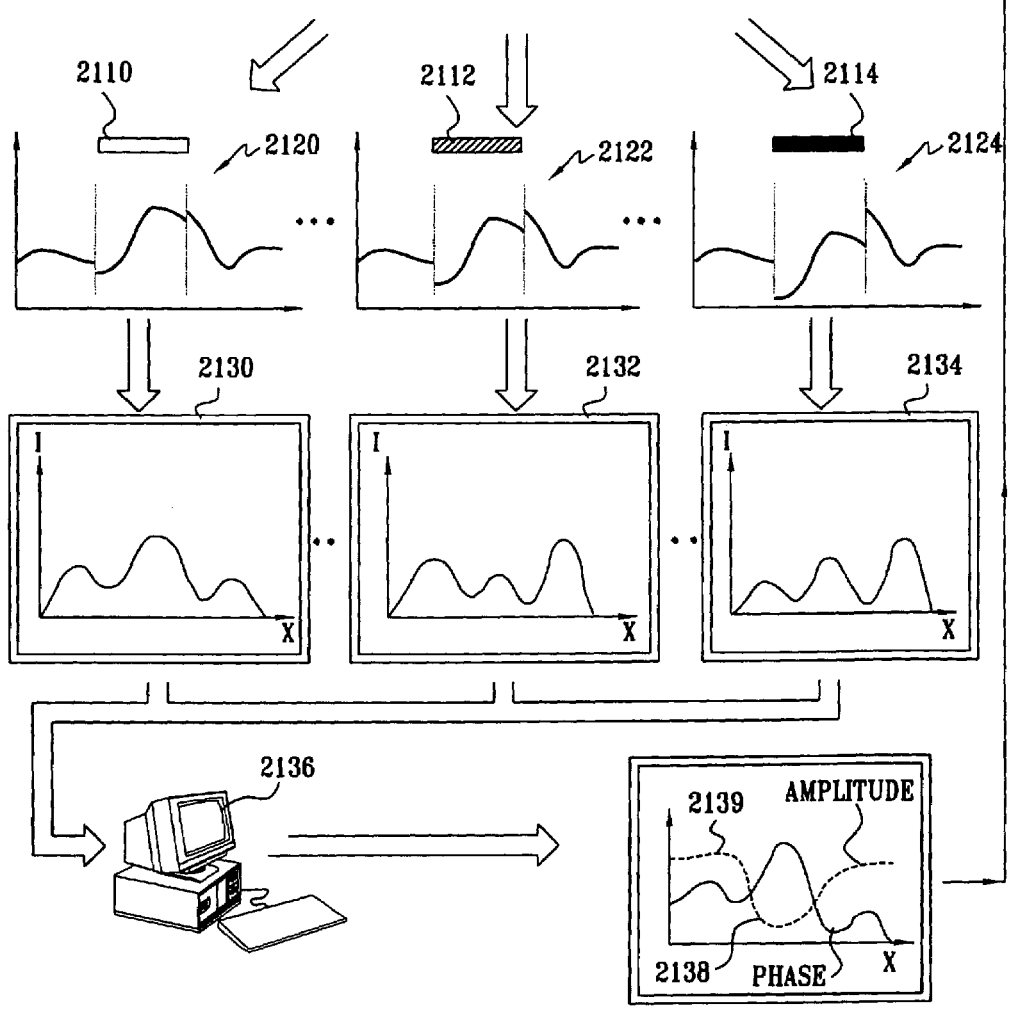

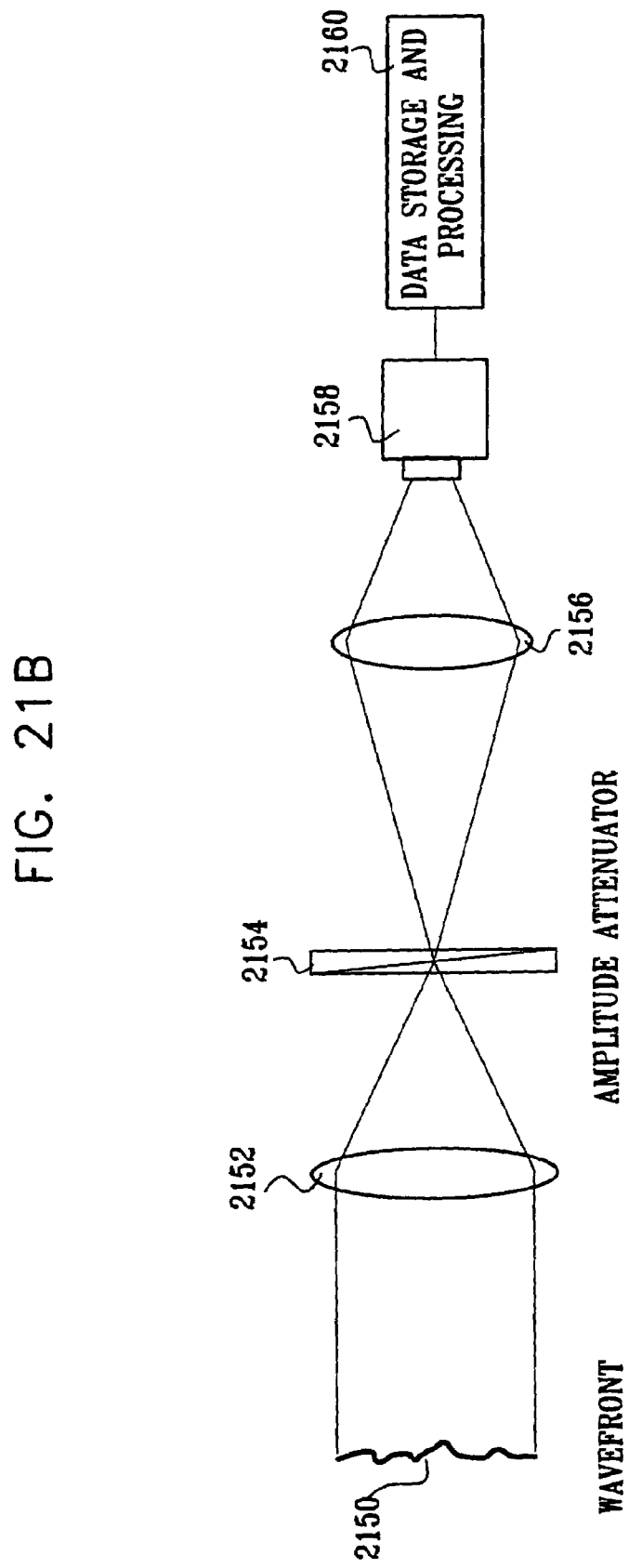

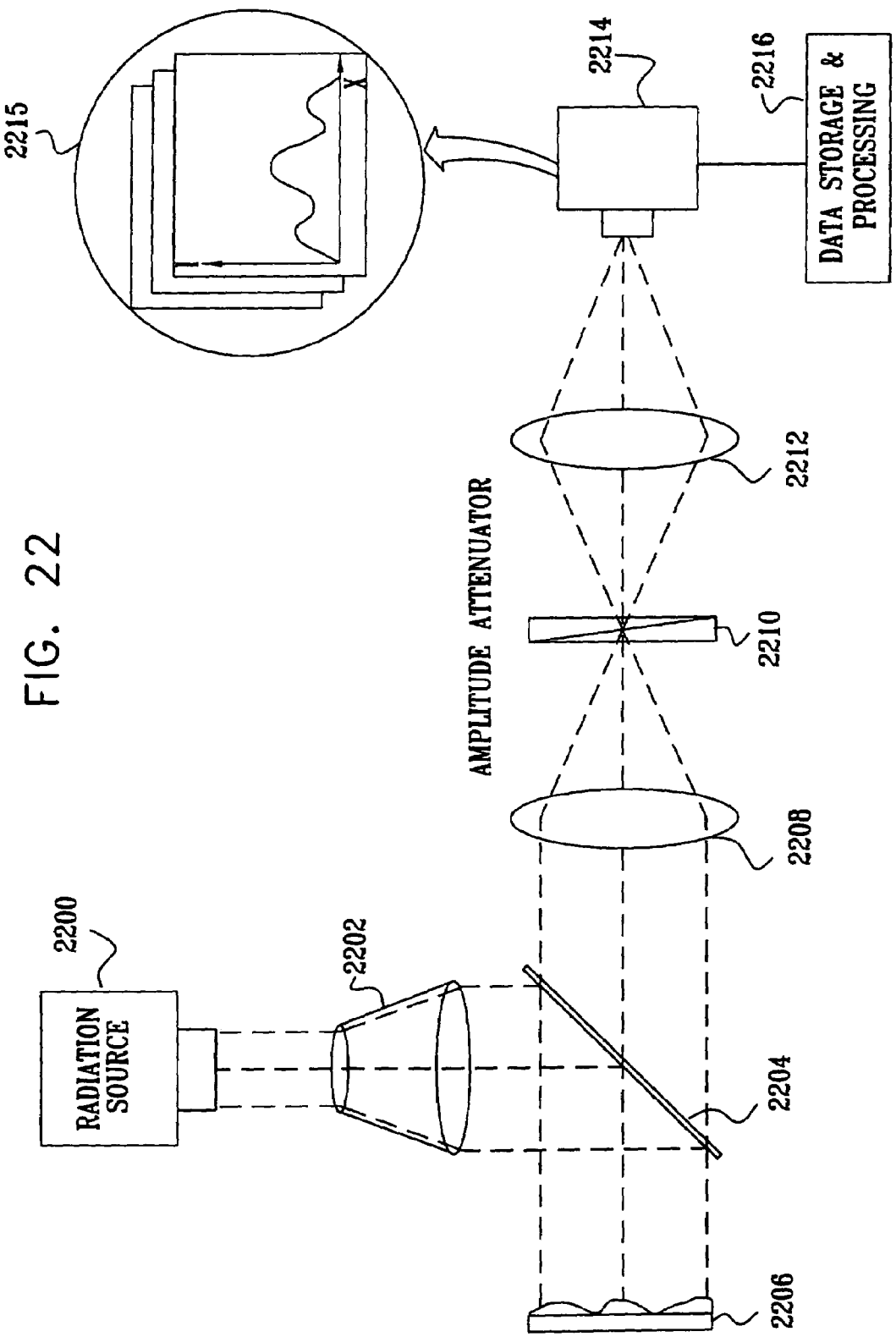

SPATIAL AND SPECTRAL WAVEFRONT ANALYSIS AND MEASUREMENT

REFERENCE TO RELATED APPLICATIONS

This is a continuation of application No. 09/829,435 filed on Apr. 9, 2001 now U.S. Pat. No. 6,819,435 which claims the benefit thereof and incorporates the same by reference. This application is based on provisional application U.S. Ser. No. 60/196,862, filed on Apr. 12, 2000.

FIELD OF THE INVENTION

The present invention relates to wavefront analysis generally and to various applications of wavefront analysis.

BACKGROUND OF THE INVENTION

The following patents and publications are believed to represent the current state of the art:

U.S. Pat. Nos.:
5,969,855; 5,969,853; 5,936,253; 5,870,191; 5,814,815; 5,751,475; 5,619,372; 5,600,440; 5,471,303; 5,446,540; 5,235,587; 4,407,569; 4,190,366;

Non-U.S. patents:
JP 9230247 (Abstract); JP 9179029 (Abstract); JP 8094936 (Abstract); JP 7261089 (Abstract); JP 7225341 (Abstract); JP 6186504 (Abstract);

Other Publications:
Phillion D. W. "General methods for generating phase-shifting interferometry algorithms"—Applied Optics, Vol. 36, 8098 (1997).
Pluta M. "Stray-light problem in phase contrast microscopy or toward highly sensitive phase contrast devices: a review"—Optical Engineering, Vol. 32, 3199 (1993).
Noda T. and Kawata S. "Separation of phase and absorption images in phase-contrast microscopy"—Journal of the Optical Society of America A, Vol. 9., 924 (1992).
Creath K. "Phase measurement interferometry techniques"—Progress in Optics XXVI, 348 (1988).
Greivenkamp J. E. "Generalized data reduction for heterodyne interferometry"—Optical Engineering, Vol. 23, 350 (1984).
Morgan C. J. "Least-squares estimation in phase-measurement interferometry"—Optics Letters, Vol. 7, 368 (1982).
Golden L. J. "Zernike test. 1: Analytical aspects"—Applied Optics, Vol. 16, 205 (1977).
Bruning J. H. et al. "Digital wavefront measuring interferometer for testing optical surfaces and lenses"—Applied Optics, Vol. 13, 2693 (1974).

SUMMARY OF THE INVENTION

The present invention seeks to provide methodologies and systems for wavefront analysis as well as for surface mapping, phase change analysis, spectral analysis, object inspection, stored data retrieval, three-dimensional; imaging and other suitable applications utilizing wavefront analysis.

There is thus provided in accordance with a preferred embodiment of the present invention a method of wavefront analysis. The method includes obtaining a plurality of differently phase changed transformed wavefronts corresponding to a wavefront being analyzed which has an amplitude and a phase, obtaining a plurality of intensity maps of the plurality of phase changed transformed wavefronts and employing the plurality of intensity maps to obtain an output indicating the amplitude and phase of the wavefront being analyzed.

There is also provided in accordance with a preferred embodiment of the present an apparatus for wavefront analysis including a wavefront transformer operating to provide a plurality of differently phase changed transformed wavefronts corresponding to a wavefront being analyzed which has an amplitude and a phase, an intensity map generator operating to provide a plurality of intensity maps of the plurality of phase changed transformed wavefronts and an intensity map utilizer, employing the plurality of intensity maps for providing an output indicating the amplitude and phase of the wavefront being analyzed.

Further in accordance with a preferred embodiment of the present invention the plurality of intensity maps are employed to provide an analytical output indicating the amplitude and phase.

Still further in accordance with a preferred embodiment of the present invention the plurality of differently phase changed transformed wavefronts are obtained by interference of the wavefront being analyzed along a common optical path.

Additionally in accordance with a preferred embodiment of the present invention the plurality of differently phase changed transformed wavefronts are realized in a manner substantially different from performing a delta-function phase change to the transformed wavefront.

Further in accordance with a preferred embodiment of the present invention the plurality of intensity maps are employed to obtain an output indicating the phase which is substantially free from halo and shading off distortions.

Preferably, the plurality of differently phase changed transformed wavefronts include a plurality of wavefronts resulting from at least one of application of spatial phase changes to a transformed wavefront and transforming of a wavefront following application of spatial phase changes thereto.

Additionally in accordance with a preferred embodiment of the present invention, the step of obtaining a plurality of differently phase changed transformed wavefronts includes applying a transform to the wavefront being analyzed thereby to obtain a transformed wavefront and applying a plurality of different phase changes to the transformed wavefront, thereby to obtain a plurality of differently phase changed transformed wavefronts. Preferably, the plurality of different phase changes includes spatial phase changes and the plurality of different spatial phase changes are effected by applying a time-varying spatial phase change to part of the transformed wavefront.

Further in accordance with a preferred embodiment of the present invention the plurality of different spatial phase changes are effected by applying a spatially uniform, time-varying spatial phase change to part of the transformed wavefront. Preferably, the transform applied to the wavefront being analyzed is a Fourier transform and wherein the step of obtaining a plurality of intensity maps of the plurality of phase changed transformed wavefronts includes applying a Fourier transform to the plurality of differently phase changed transformed wavefronts.

Further in accordance with a preferred embodiment of the present invention the transform applied to the wavefront being analyzed is a Fourier transform and the plurality of different spatial phase changes includes at least three different phase changes. Preferably, the plurality of intensity maps includes at least three intensity maps and the step of employing the plurality of intensity maps to obtain an output indicating the amplitude and phase of the wavefront being analyzed includes: expressing the wavefront being analyzed as a first complex function which has an amplitude and phase identical to the amplitude and phase of the wavefront being analyzed, expressing the plurality of intensity maps as a function of the first complex function and of a spatial function governing the spatially uniform, time-varying spatial phase change, defining a second complex function, having an absolute value and a phase, as a convolution of the first complex function and of a Fourier transform of the spatial function governing the spatially uniform, time-varying spatial phase change. Expressing each of the plurality of intensity maps as a third function of: the amplitude of the wavefront being analyzed, the absolute value of the second complex function, a difference between the phase of the wavefront being analyzed and the phase of the second complex function and a known phase delay produced by one of the at least three different phase changes corresponding to one of the at least three intensity maps, solving the third function to obtain the amplitude of the wavefront being analyzed, the absolute value of the second complex function and the difference between the phase of the wavefront being analyzed and the phase of the second complex function, solving the second complex function to obtain the phase of the second complex function and obtaining the phase of the wavefront being analyzed by adding the phase of the second complex function to the difference between the phase of the wavefront being analyzed and the phase of the second complex function.

Further in accordance with a preferred embodiment of the present invention the absolute value of the second complex function is obtained by approximating the absolute value to a polynomial of a given degree.

Still further in accordance with a preferred embodiment of the present invention the second complex function is obtained by expressing the second complex function as an eigen-value problem where the complex function is an eigen-vector obtained by an iterative process.

Preferably the second complex function is obtained by: approximating the Fourier transform of the spatial function governing the spatially uniform, time-varying spatial phase change to a polynomial and approximating the second complex function to a polynomial.

Preferably, the wavefront being analyzed, the absolute value of the second complex function, and the difference between the phase of the second complex function and the phase of the wavefront being analyzed, are obtained by a least-square method, which has increased accuracy as the number of the plurality of intensity maps increases.

Further in accordance with a preferred embodiment of the present invention the plurality of different phase changes includes at least four different phase changes, the plurality of intensity maps includes at least four intensity maps and employing the plurality of intensity maps to obtain an output indicating the amplitude and phase of the wavefront being analyzed and includes: expressing each of the plurality of intensity maps as a third function of: the amplitude of the wavefront being analyzed, the absolute value of the second complex function, a difference between the phase of the wavefront being analyzed and the phase of the second complex function, a known phase delay produced by one of the at least four different phase changes in which each corresponds to one of the at least four intensity maps and at least one additional unknown relating to the wavefront analysis, where the number of the at least one additional unknown is no greater than the number by which the plurality intensity maps exceeds three and solving the third function to obtain the amplitude of the wavefront being analyzed, the absolute value of the second complex function, the difference between the phase of the wavefront being analyzed and the phase of the second complex function and the additional unknown.

Further in accordance with a preferred embodiment of the present invention the phase changes are chosen as to maximize contrast in the intensity maps and to minimize effects of noise on the phase of the wavefront being analyzed.

Preferably, expressing each of the plurality of intensity maps as a third function of: the amplitude of the wavefront being analyzed, the absolute value of the second complex function, a difference between the phase of the wavefront being analyzed and the phase of the second complex function and a known phase delay produced by one of the at least three different phase changes which corresponds to one of the at least three intensity maps and includes: defining fourth, fifth and sixth complex functions, none of which being a function of any of the plurality of intensity maps or of the time-varying spatial phase change, each of the fourth, fifth and sixth complex functions being a function of the amplitude of the wavefront being analyzed, the absolute value of the second complex function and the difference between the phase of the wavefront being analyzed and the phase of the second complex function and expressing each of the plurality of intensity maps as a sum of the fourth complex function, the fifth complex function multiplied by the sine of the known phase delay corresponding to each one of the plurality of intensity maps and the sixth complex function multiplied by the cosine of the known phase delay corresponding to each one of the plurality of intensity maps.

Preferably, the step of solving the third function to obtain the amplitude of the wavefront being analyzed, the absolute value of the second complex function and the difference between the phase of the wavefront being analyzed and the phase of the second complex function includes: obtaining two solutions for each of the amplitude of the wavefront being analyzed, the absolute value of the second complex function and the difference between the phase of the wavefront being analyzed and the phase of the second complex function, the two solutions being a higher value solution and a lower value solution, combining the two solutions into an enhanced absolute value solution for the absolute value of the second complex function, by choosing at each spatial location either the higher value solution or the lower value solution of the two solutions in a way that the enhanced absolute value solution satisfies the second complex function. Preferably, combining the two solutions of the amplitude of the wavefront being analyzed into enhanced amplitude solution, by choosing at each spatial location the higher value solution or the lower value solution of the two solutions of the amplitude in the way that at each location where the higher value solution is chosen for the absolute value solution, the higher value solution is chosen for the amplitude solution and at each location where the lower value solution is chosen for the absolute value solution, the lower value solution is chosen for the amplitude solution, combining the two solutions of the difference between the phase of the wavefront being analyzed and the phase of the second complex function into an enhanced difference solution, by choosing at each spatial location the higher value solution or the lower value solution of the two solutions of the difference in the way that at each location where the higher value solution is chosen for the absolute value solution, the higher value solution is chosen for the difference solution and at each location where the lower value solution is chosen for the absolute value solution, the lower value solution is chosen for the difference solution.

Further in accordance with a preferred embodiment of the present invention the spatially uniform, time-varying spatial phase change is applied to a spatially central part of the transformed wavefront.

Preferably, the transform applied to the wavefront being analyzed is a Fourier transform and wherein the step of obtaining a plurality of intensity maps of the plurality of phase changed transformed wavefronts includes applying a Fourier transform to the plurality of differently phase changed transformed wavefronts.

Still further in accordance with a preferred embodiment of the present invention the method also includes adding a phase component including relatively high frequency components to the wavefront being analyzed prior to applying the transform thereto in order to increase the high-frequency content of the transformed wavefront prior to the applying the spatially uniform, time-varying spatial phase change to part of the transformed wavefront.

Preferably, the spatially uniform, time-varying spatial phase change is applied to a spatially centered generally circular region of the transformed wavefront and the spatially uniform, time-varying spatial phase change is applied to approximately one half of the transformed wavefront.

Additionally in accordance with a preferred embodiment of the present invention the transformed wavefront includes a DC region and a non-DC region and the spatially uniform, time-varying spatial phase change is applied to at least part of both the DC region and the non-DC region.

Further in accordance with a preferred embodiment of the present invention the plurality of differently phase changed transformed wavefronts include a plurality of wavefronts whose phase has been changed by employing an at least time varying phase change function. Alternatively, the plurality of differently phase changed transformed wavefronts include a plurality of wavefronts whose phase has been changed by applying an at least time varying phase change function to the wavefront being analyzed.

Preferably, the at least time varying phase change function is applied to the wavefront being analyzed prior to transforming thereof. Alternatively, the at least time varying phase change function is applied to the wavefront being analyzed subsequent to transforming thereof.

Further in accordance with a preferred embodiment of the present invention the plurality of differently phase changed transformed wavefronts include a plurality of wavefronts whose phase has been changed by employing an at least time varying phase change function.

Additionally or alternatively, the plurality of differently phase changed transformed wavefronts include a plurality of wavefronts whose phase has been changed by applying an at least time varying phase change function to the wavefront to be analyzed.

Preferably, the at least time varying phase change function is a spatially uniform spatial function.

Additionally in accordance with a preferred embodiment of the present invention the transformed wavefront includes a plurality of different wavelength components and the plurality of different spatial phase changes are effected by applying a phase change to the plurality of different wavelength components of the transformed wavefront.

Preferably, the phase change applied to the plurality of different wavelength components of the transformed wavefront is a time-varying spatial phase change.

Further in accordance with a preferred embodiment of the present invention the phase change applied to the plurality of different wavelength components of the transformed wavefront is effected by passing the transformed wavefront through an object, at least one of whose thickness and refractive index varies spatially.

Still further in accordance with a preferred embodiment of the present invention the phase change applied to the plurality of different wavelength components of the transformed wavefront is effected by reflecting the transformed wavefront from a spatially varying surface.

Further in accordance with a preferred embodiment of the present invention the phase change applied to the plurality of different wavelength components of the transformed wavefront is selected to be different to a predetermined extent for at least some of the plurality of different wavelength components.

Additionally in accordance with a preferred embodiment of the present invention the phase change applied to the plurality of different wavelength components of the transformed wavefront is identical for at least some of the plurality of different wavelength components.

Further in accordance with a preferred embodiment of the present invention the wavefront being analyzed includes a plurality of different wavelength components.

Preferably, the plurality of differently phase changed transformed wavefronts are obtained by applying a phase change to the plurality of different wavelength components of the wavefront being analyzed.

Preferably, the phase change is applied to the plurality of different wavelength components of the wavefront being analyzed prior to transforming thereof.

Further in accordance with a preferred embodiment of the present invention the phase change applied to the plurality of different wavelength components is effected by passing the wavefront being analyzed through an object, at least one of whose thickness and refractive index varies spatially.

Further in accordance with a preferred embodiment of the present invention the step of obtaining a plurality of intensity maps is performed simultaneously for all of the plurality of different wavelength components and obtaining a plurality of intensity maps includes dividing the plurality of phase changed transformed wavefronts into separate wavelength components.

Still further in accordance with a preferred embodiment of the present invention the step of dividing the plurality of phase changed transformed wavefronts is effected by passing the plurality of phase changed transformed wavefronts through a dispersion element.

Additionally in accordance with a preferred embodiment of the present invention the phase change applied to the plurality of different wavelength components is effected by passing the wavefront being analyzed through an object, at least one of whose thickness and refractive index varies spatially, following transforming of the wavefront being analyzed.

Preferably, the phase change which is applied to the plurality of different wavelength components is effected by reflecting the wavefront being analyzed from a spatially varying surface, following transforming of the wavefront being analyzed.

Further in accordance with a preferred embodiment of the present invention the phase change applied to the plurality of different wavelength components is selected to be different to a predetermined extent for at least some of the plurality of different wavelength components. Preferably, the phase change which is applied to the plurality of different wavelength components is identical for at least some of the plurality of different wavelength components.

Further in accordance with a preferred embodiment of the present invention the phase change applied to the plurality of different wavelength components is effected by passing the wavefront being analyzed through a plurality of objects, each characterized in that at least one of its thickness and refractive index varies spatially.

Preferably, the phase change applied to the plurality of different wavelength components is effected by passing the wavefront being analyzed through a plurality of objects, each characterized in that at least one of its thickness and refractive index varies spatially, following transforming of the wavefront being analyzed.

Further in accordance with a preferred embodiment of the present invention the wavefront being analyzed includes a plurality of different polarization components and the plurality of differently phase changed transformed wavefronts are obtained by applying a phase change to the plurality of different polarization components of the wavefront being analyzed prior to transforming thereof.

Still further in accordance with a preferred embodiment of the present invention the transformed wavefront includes a plurality of different polarization components and the plurality of different spatial phase changes are effected by applying a phase change to the plurality of different polarization components of the transformed wavefront.

Additionally in accordance with a preferred embodiment of the present invention the phase change applied to the plurality of different polarization components of the transformed wavefront is different for at least some of the plurality of different polarization components.

Further in accordance with a preferred embodiment of the present invention the phase change applied to the plurality of different polarization components of the transformed wavefront is identical for at least some of the plurality of different polarization components.

Additionally in accordance with a preferred embodiment of the present invention the step of obtaining a plurality of intensity maps of the plurality of phase changed transformed wavefronts includes applying a transform to the plurality of differently phase changed transformed wavefronts.

Preferably, the plurality of phase changed transformed wavefronts are reflected from a reflecting surface so that the transform applied to the plurality of differently phase changed transformed wavefronts is identical to the transform applied to the wavefront being analyzed.

Further in accordance with a preferred embodiment of the present invention the transform applied to the wavefront being analyzed is a Fourier transform.

Still further in accordance with a preferred embodiment of the present invention the plurality of intensity maps are obtained by reflecting the plurality of differently phase changed transformed wavefronts from a reflecting surface so as to transform the plurality of differently phase changed transformed wavefronts.

Additionally in accordance with a preferred embodiment of the present invention the method of obtaining a plurality of intensity maps of the plurality of phase changed transformed wavefronts includes applying a transform to the plurality of differently phase changed transformed wavefronts.

Further in accordance with a preferred embodiment of the present invention the method of employing the plurality of intensity maps to obtain an output indicating the amplitude and phase of the wavefront being analyzed includes expressing the plurality of intensity maps as at least one mathematical function of phase and amplitude of the wavefront being analyzed and employing the at least one mathematical function to obtain an output indicating the phase and amplitude.

Preferably, the method of employing the plurality of intensity maps to obtain an output indicating the amplitude and phase of the wavefront being analyzed includes expressing the plurality of intensity maps as at least one mathematical function of phase and amplitude of the wavefront being analyzed and of the plurality of different phase changes, wherein the phase and amplitude are unknowns and the plurality of different phase changes are known and employing the at least one mathematical function to obtain an output indicating the phase and amplitude.

Further in accordance with a preferred embodiment of the present invention the plurality of intensity maps includes at least four intensity maps and employing the plurality of intensity maps to obtain an output indicating the amplitude and phase of the wavefront being analyzed, includes employing a plurality of combinations, each of at least three of the plurality of intensity maps, to provide a plurality of indications of the amplitude and phase of the wavefront being analyzed.

Preferably, the method also includes employing the plurality of indications of the amplitude and phase of the wavefront being analyzed to provide an enhanced indication of the amplitude and phase of the wavefront being analyzed.

Further in accordance with a preferred embodiment of the present invention at least some of the plurality of indications of the amplitude and phase are at least second order indications of the amplitude and phase of the wavefront being analyzed.

Further in accordance with a preferred embodiment of the present invention the step of obtaining a plurality of differently phase changed transformed wavefronts includes applying a transform to the wavefront being analyzed, thereby obtaining a transformed wavefront and applying a plurality of different phase and amplitude changes to the transformed wavefront, thereby obtaining a plurality of differently phase and amplitude changed transformed wavefronts.

Further in accordance with a preferred embodiment of the present invention the plurality of different phase and amplitude changes includes at least three different phase and intensity changes, the plurality of different phase and amplitude changes are effected by applying at least one of a spatially uniform, time-varying spatial phase change and a spatially uniform, time-varying spatial amplitude change to at least part of the transformed wavefront, the plurality of intensity maps includes at least three intensity maps. Preferably, the step of employing the plurality of intensity maps to obtain an output indicating the amplitude and phase of the wavefront being analyzed includes: expressing the wavefront being analyzed as a first complex function which has an amplitude and phase identical to the amplitude and phase of the wavefront being analyzed, expressing the plurality of intensity maps as a function of the first complex function and of a spatial function governing at least one of a spatially uniform, time-varying spatial phase change and a spatially uniform, time-varying spatial amplitude change, defining a second complex function having an absolute value and a phase as a convolution of the first complex function and of a Fourier transform of the spatial function governing the spatially uniform, time-varying spatial phase change, expressing each of the plurality of intensity maps as a third function of: the amplitude of the wavefront being analyzed, the absolute value of the second complex function and a difference between the phase of the wavefront being analyzed and the phase of the second complex function. Preferably, the spatial function governing at least one of a spatially uniform, time-varying spatial phase change and a spatially uniform, time-varying spatial amplitude change includes: defining fourth, fifth, sixth and seventh complex functions, none of which is a function of any of the plurality of intensity maps or of the time-varying spatial phase change. Preferably, each of the fourth, fifth, sixth and seventh complex functions being a function of at least one of: the amplitude of the wavefront being analyzed, the absolute value of the second complex function and the difference between the phase of the wavefront being analyzed and the phase of the second complex function, defining an eighth function of a phase delay and of an amplitude change, both produced by one of the at least three different phase and amplitude changes, corresponding to the at least three intensity maps and expressing each of the plurality of intensity maps as a sum of the fourth complex function, the fifth complex function multiplied by the absolute value squared of the eighth function, the sixth complex function multiplied by the eighth function and the seventh complex function multiplied by the complex conjugate of the eighth function, solving the third function to obtain the amplitude of the wavefront being analyzed, the absolute value of the second complex function and the difference between the phase of the wavefront being analyzed and the phase of the second complex function, solving the second complex function to obtain the phase of the second complex function and obtaining the phase of the wavefront being analyzed by adding the phase of the second complex function to the difference between the phase of the wavefront being analyzed and phase of the second complex function.

Further in accordance with a preferred embodiment of the present invention the wavefront being analyzed includes at least two wavelength components. Preferably, the step of obtaining a plurality of intensity maps also includes dividing the phase changed transformed wavefronts according to the at least two wavelength components in order to obtain at least two wavelength components of the phase changed transformed wavefronts and in order to obtain at least two sets of intensity maps, each set corresponding to a different one of the at least two wavelength components of the phase changed transformed wavefronts and employing the plurality of intensity maps to obtain an output indicating the amplitude and phase of the wavefront being analyzed, obtaining an output indicative of the phase of the wavefront being analyzed from each of the at least two sets of intensity maps and combining the outputs to provide an enhanced indication of phase of the wavefront being analyzed, in which enhanced indication, there is no $2\pi$ ambiguity.

Additionally in accordance with a preferred embodiment of the present invention the wavefront being analyzed is an acoustic radiation wavefront.

Still further in accordance with a preferred embodiment of the present invention the wavefront being analyzed includes at least one one-dimensional component, the transform applied to the wavefront being analyzed is a one-dimensional Fourier transform, performed in a dimension perpendicular to a direction of propagation of the wavefront being analyzed, thereby to obtain at least one one-dimensional component of the transformed wavefront in the dimension perpendicular to the direction of propagation. The plurality of differently phase changed transformed wavefronts are obtained by applying the plurality of different phase changes to each of the at least one one-dimensional component, thereby obtaining at least one one-dimensional component of the plurality of phase changed transformed wavefronts and the plurality of intensity maps are employed to obtain an output indicating amplitude and phase of the at least one one-dimensional component of the wavefront being analyzed.

Preferably, the plurality of different phase changes is applied to each of the one-dimensional component by providing a relative movement between the wavefront being analyzed and an element. Preferably, the element generates spatially varying, time-constant phase changes, the relative movement being in an additional dimension which is perpendicular both to the direction of propagation and to the dimension perpendicular to the direction of propagation.

Further in accordance with a preferred embodiment of the present invention the wavefront being analyzed includes a plurality of different wavelength components, the plurality of different phase changes are applied to the plurality of different wavelength components of each of the plurality of one-dimensional components of the wavefront being analyzed and the step of obtaining a plurality of intensity maps includes dividing the plurality of one-dimensional components of the plurality of phase changed transformed wavefronts into separate wavelength components.

Still further in accordance with a preferred embodiment of the present invention dividing the plurality of one-dimensional components of the plurality of phase changed transformed wavefronts into separate wavelength components is achieved by passing the plurality of phase changed transformed wavefronts through a dispersion element.

Further in accordance with a preferred embodiment of the present invention the transform applied to the wavefront being analyzed includes an additional Fourier transform to minimize cross-talk between different one-dimensional components of the wavefront being analyzed.

There is provided in accordance with another preferred embodiment of the present invention a method of surface mapping. The method includes obtaining a surface mapping wavefront having an amplitude and a phase, by reflecting radiation from a surface and analyzing the surface mapping wavefront by: obtaining a plurality of differently phase changed transformed wavefronts corresponding to the surface mapping wavefront, obtaining a plurality of intensity maps of the plurality of phase changed transformed wavefronts and employing the plurality of intensity maps to obtain an output indicating the amplitude and phase of the surface mapping wavefront.

There is further provided in accordance with a preferred embodiment of the present invention an apparatus for surface mapping. The apparatus includes a wavefront obtainer operating to obtain a surface mapping wavefront having an amplitude and a phase, by reflecting radiation from a surface, a wavefront analyzer, analyzing the surface mapping wavefront and including a wavefront transformer operating to provide a plurality of differently phase changed transformed wavefronts corresponding to the surface mapping wavefront, an intensity map generator operating to provide a plurality of intensity maps of the plurality of phase changed transformed wavefronts and an intensity map utilizer, the plurality of intensity maps provide an output indicating the amplitude and phase of the surface mapping wavefront.

Further in accordance with a preferred embodiment of the present invention the radiation reflected from the surface has a narrow band about a given wavelength, causing the phase of the surface mapping wavefront to be proportional to geometrical variations in the surface, the proportion being an inverse linear function of the wavelength.

Still further in accordance with a preferred embodiment of the present invention the radiation reflected from the surface has at least two narrow bands, each centered about a different wavelength, providing at least two wavelength components in the surface mapping wavefront and at least two indications of the phase of the surface mapping wavefront, thereby enabling an enhanced mapping of the surface to be obtained by avoiding an ambiguity in the mapping which exceeds the larger of the different wavelengths about which the two narrow bands are centered.

Additionally in accordance with a preferred embodiment of the present invention the step of obtaining a plurality of differently phase changed transformed wavefronts includes applying a transform to the surface mapping wavefront, thereby to obtain a transformed wavefront and applying a plurality of different phase changes, including spatial phase changes, to the transformed wavefront, thereby to obtain a plurality of differently phase changed transformed wavefronts.

Further in accordance with a preferred embodiment of the present invention the transform applied to the surface mapping wavefront is a Fourier transform, the plurality of different phase changes includes at least three different phase changes, effected by applying a spatially uniform, time-varying spatial phase change to part of the transformed wavefront, the plurality of intensity maps includes at least three intensity maps. Preferably, the step of employing the plurality of intensity maps to obtain an output indicates the amplitude and phase of the surface mapping wavefront and includes expressing the surface mapping wavefront as a first complex function which has an amplitude and phase identical to the amplitude and phase of the surface mapping wavefront, expressing the plurality of intensity maps as a function of the first complex function and of a spatial function governing the spatially uniform, time-varying spatial phase change, defining a second complex function having an absolute value and a phase as a convolution of the first complex function and of a Fourier transform of the spatial function governing the spatially uniform, time-varying spatial phase change. Preferably, expressing each of the plurality of intensity maps as a third function of: the amplitude of the surface mapping wavefront, the absolute value of the second complex function, a difference between the phase of the surface mapping wavefront and the phase of the second complex function and a known phase delay produced by one of the at least three different phase changes, corresponding to one of the at least three intensity maps, solving the third function to obtain the amplitude of the surface mapping wavefront, the absolute value of the second complex function and the difference between the phase of the surface mapping wavefront and the phase of the second complex function, solving the second complex function to obtain the phase of the second complex function and obtaining the phase of the surface mapping wavefront by adding the phase of the second complex function to the difference between the phase of the surface mapping wavefront and phase of the second complex function.

Preferably, the surface mapping wavefront includes a plurality of different wavelength components. The plurality of differently phase changed transformed wavefronts are preferably obtained by: transforming the surface mapping wavefront thereby obtaining a transformed wavefront including a plurality of different wavelength components and applying a phase change to the plurality of different wavelength components of the transformed wavefront by passing the transformed wavefront through an object, at least one of whose thickness and refractive index varies spatially.

There is also provided in accordance with yet another preferred embodiment of the present invention a method of inspecting an object. The method includes obtaining an object inspection wavefront which has an amplitude and a phase, by transmitting radiation through the object and analyzing the object inspection wavefront by: obtaining a plurality of differently phase changed transformed wavefronts corresponding to the object inspection wavefront, obtaining a plurality of intensity maps of the plurality of phase changed transformed wavefronts and employing the plurality of intensity maps to obtain an output indicating the amplitude and phase of the object inspection wavefront.

There is further provided in accordance with a preferred embodiment of the present invention an apparatus for inspecting an object. The apparatus includes a wavefront obtainer operating to obtain an object inspection wavefront which has an amplitude and a phase, by transmitting radiation through the object, a wavefront analyzer, analyzing the object inspection wavefront and including a wavefront transformer operating to provide a plurality of differently phase changed transformed wavefronts corresponding to the object inspection wavefront, an intensity map generator operating to provide a plurality of intensity maps of the plurality of phase changed transformed wavefronts and an intensity map utilizer, employing the plurality of intensity maps to provide an output indicating the amplitude and phase of the object inspection wavefront.

Preferably, when the object is substantially uniform in material and other optical properties, the phase of the object inspection wavefront is proportional to the object thickness.

Additionally, when the object is substantially uniform in thickness, the phase of the object inspection wavefront is proportional to optical properties of the object.

Further in accordance with a preferred embodiment of the present invention the radiation has at least two narrow bands, each centered about a different wavelength, providing at least two wavelength components in the object inspection wavefront and at least two indications of the phase of the object inspection wavefront, thereby enabling an enhanced mapping of thickness of the object to be inspected by avoiding an ambiguity in the mapping which exceeds the larger of the different wavelengths about which the two narrow bands are centered.

Still further in accordance with a preferred embodiment of the present invention the method of obtaining a plurality of differently phase changed transformed wavefronts includes applying a transform to the object inspection wavefront, thereby obtaining a transformed wavefront and applying a plurality of different phase changes, including spatial phase changes, to the transformed wavefront, thereby obtaining a plurality of differently phase changed transformed wavefronts.

Further in accordance with a preferred embodiment of the present invention the transform applied to the object inspection wavefront is a Fourier transform, the plurality of different phase changes includes at least three different phase changes, effected by applying a spatially uniform, time-varying spatial phase change to part of the transformed wavefront. Preferably, the plurality of intensity maps includes at least three intensity maps and employing the plurality of intensity maps to obtain an output indicating the amplitude and phase of the object inspection wavefront and includes: expressing the object inspection wavefront as a first complex function which has an amplitude and phase identical to the amplitude and phase of the object inspection wavefront, expressing the plurality of intensity maps as a function of the first complex function and of a spatial function governing the spatially uniform, time-varying spatial phase change, defining a second complex function having an absolute value and a phase as a convolution of the first complex function and of a Fourier transform of the spatial function governing the spatially uniform, time-varying spatial phase change, expressing each of the plurality of intensity maps as a third function of: the amplitude of the object inspection wavefront, the absolute value of the second complex function, a difference between the phase of the object inspection wavefront and the phase of the second complex function and a known phase delay produced by one of the at least three different phase changes, corresponding to one of the at least three intensity maps, solving the third function to obtain the amplitude of the object inspection wavefront, the absolute value of the second complex function and the difference between the phase of the object inspection wavefront and the phase of the second complex function, solving the second complex function to obtain the phase of the second complex function and obtaining the phase of the object inspection wavefront by adding the phase of the second complex function to the difference between the phase of the object inspection wavefront and phase of the second complex function.

Still further in accordance with a preferred embodiment of the present invention the object inspection wavefront includes a plurality of different wavelength components. The plurality of differently phase changed transformed wavefronts are preferably obtained by: transforming the object inspection wavefront thereby obtaining a transformed wavefront including a plurality of different wavelength components and applying a phase change to the plurality of different wavelength components of the transformed wavefront by reflecting the transformed wavefront from a spatially varying surface.

There is also provided in accordance with yet another preferred embodiment of the present invention a method of spectral analysis. The method includes obtaining a spectral analysis wavefront having an amplitude and a phase, by causing radiation to impinge on an object, analyzing the spectral analysis wavefront by: obtaining a plurality of differently phase changed transformed wavefronts corresponding to the spectral analysis wavefront which has an amplitude and a phase, obtaining a plurality of intensity maps of the plurality of phase changed transformed wavefronts and employing the plurality of intensity maps to obtain an output indicating the amplitude and phase of the spectral analysis wavefront and employing the output indicating the amplitude and phase to obtain an output indicating spectral content of the radiation.

There is provided in accordance with a further preferred embodiment of the present invention an apparatus for spectral analysis. The apparatus includes a wavefront obtainer operating to obtain a spectral analysis wavefront having an amplitude and a phase, by causing radiation to impinge on an object, a wavefront analyzer, analyzing the spectral analysis wavefront, including a wavefront transformer operating to provide a plurality of differently phase changed transformed wavefronts corresponding to the spectral analysis wavefront which has an amplitude and a phase, an intensity map generator operating to provide a plurality of intensity maps of the plurality of phase changed transformed wavefronts, an intensity map utilizer, employing the plurality of intensity maps to provide an output indicating the amplitude and phase of the spectral analysis wavefront and a phase and amplitude utilizer, employing the output indicating the amplitude and phase to obtain an output indicating spectral content of the radiation.

Further in accordance with a preferred embodiment of the present invention and wherein obtaining the spectral analysis wavefront is effected by reflecting the radiation from the object.

Still further in accordance with a preferred embodiment of the present invention and wherein obtaining the spectral analysis wavefront is effected by transmitting the radiation through the object.

Additionally in accordance with a preferred embodiment of the present invention the radiation is substantially of a single wavelength, the phase of the spectral analysis wavefront is inversely proportional to the single wavelength, and is related to at least one of a surface characteristic and thickness of the impinged object.

Still further in accordance with a preferred embodiment of the present invention the step of employing the plurality of intensity maps to obtain an output indicating the amplitude and phase of the spectral analysis wavefront includes: expressing the plurality of intensity maps as at least one mathematical function of phase and amplitude of the spectral analysis wavefront and of the plurality of different phase changes, wherein at least the phase is unknown and a function generating the plurality of phase changed transformed wavefronts is known and employing the at least one mathematical function to obtain an output indicating at least the phase.

Additionally in accordance with a preferred embodiment of the present invention the step of obtaining a plurality of differently phase changed transformed wavefronts includes applying a transform to the spectral analysis wavefront, thereby obtaining a transformed wavefront and applying a plurality of different phase changes, including spatial phase changes, to the transformed wavefront, thereby obtaining a plurality of differently phase changed transformed wavefronts.

Further in accordance with a preferred embodiment of the present invention the transform applied to the spectral analysis wavefront is a Fourier transform, the plurality of different phase changes includes at least three different phase changes, effected by applying a spatially uniform, time-varying spatial phase change to part of the transformed wavefront. Preferably, the plurality of intensity maps includes at least three intensity maps and employing the plurality of intensity maps to obtain an output indicating the amplitude and phase of the spectral analysis wavefront includes: expressing the spectral analysis wavefront as a first complex function which has an amplitude and phase identical to the amplitude and phase of the spectral analysis wavefront, expressing the plurality of intensity maps as a function of the first complex function and of a spatial function governing the spatially uniform, time-varying spatial phase change, defining a second complex function having an absolute value and a phase as a convolution of the first complex function and of a Fourier transform of the spatial function governing the spatially uniform, time-varying spatial phase change, expressing each of the plurality of intensity maps as a third function of: the amplitude of the spectral analysis wavefront, the absolute value of the second complex function, a difference between the phase of the spectral analysis wavefront and the phase of the second complex function and a known phase delay produced by one of the at least three different phase changes, corresponding to one of the at least three intensity maps, solving the third function to obtain the amplitude of the spectral analysis wavefront, the absolute value of the second complex function and the difference between the phase of the spectral analysis wavefront and the phase of the second complex function, solving the second complex function to obtain the phase of the second complex function and obtaining the phase of the spectral analysis wavefront by adding the phase of the second complex function to the difference between the phase of the spectral analysis wavefront and phase of the second complex function.

Further in accordance with a preferred embodiment of the present invention the spectral analysis wavefront includes a plurality of different wavelength components and the plurality of differently phase changed transformed wavefronts are obtained by applying a phase change to the plurality of different wavelength components of the spectral analysis wavefront.

There is further provided in accordance with a preferred embodiment of the present invention a method of phase change analysis. The method includes obtaining a phase change analysis wavefront which has an amplitude and a phase, applying a transform to the phase change analysis wavefront thereby to obtain a transformed wavefront, applying a plurality of different phase changes to the transformed wavefront, thereby to obtain a plurality of differently phase changed transformed wavefronts, obtaining a plurality of intensity maps of the plurality of phase changed transformed wavefronts and employing the plurality of intensity maps to obtain an output indication of differences between the plurality of different phase changes applied to the transformed phase change analysis wavefront.

There is also provided in accordance with yet another preferred embodiment of the present invention an apparatus for phase change analysis. The apparatus includes a wavefront obtainer, operating to obtain a phase change analysis wavefront which has an amplitude and a phase, a transform applier, applying a transform to the phase change analysis wavefront thereby to obtain a transformed wavefront, a phase change applier, applying at least one phase change to the transformed wavefront, thereby to obtain at least one phase changed transformed wavefront, an intensity map generator operating to provide at least one intensity map of the phase changed transformed wavefront and an intensity map utilizer, employing the plurality of intensity maps to provide an output indication of differences between the plurality of different phase changes applied to the transformed phase change analysis wavefront.

Typically, when lateral shifts appear in the plurality of different phase changes, corresponding changes appear in the plurality of intensity maps and the step of employing the plurality of intensity maps results in obtaining an indication of the lateral shifts.

Still further in accordance with a preferred embodiment of the present invention the step of employing the plurality of intensity maps to obtain an output indication of differences between the plurality of different phase changes applied to the transformed phase change analysis wavefront includes: expressing the plurality of intensity maps as at least one mathematical function of phase and amplitude of the phase change analysis wavefront and of the plurality of different phase changes, where at least the phase and amplitude are known and the plurality of different phase changes are unknown and employing the mathematical function to obtain an output indicating the differences between the plurality of different phase changes.

There is further provided in accordance with yet a further preferred embodiment of the present invention a method of phase change analysis. The method includes obtaining a phase change analysis wavefront which has an amplitude and a phase, applying a transform to the phase change analysis wavefront thereby to obtain a transformed wavefront, applying at least one phase change to the transformed wavefront, thereby to obtain at least one phase changed transformed wavefront, obtaining at least one intensity map of the at least one phase changed transformed wavefront and employing the intensity map to obtain an output indication of the at least one phase change applied to the transformed phase change analysis wavefront.

There is also provided in accordance with yet another preferred embodiment of the present invention an apparatus for phase change analysis. The apparatus includes a wavefront obtainer, operating to obtain a phase change analysis wavefront which has an amplitude and a phase, a transform applier, applying a transform to the phase change analysis wavefront thereby to obtain a transformed wavefront, a phase change applier, applying at least one phase change to the transformed wavefront, thereby to obtain at least one phase changed transformed wavefront, an intensity map generator operating to provide at least one intensity map of the phase changed transformed wavefront and an intensity map utilizer, employing the intensity map to provide an output indication of the phase change applied to the transformed phase change analysis wavefront.

Preferably, the phase change is a phase delay, having a value selected from a plurality of pre-determined values, and the output indication of the phase change includes the value of the phase delay.

There is also provided in accordance with a preferred embodiment of the present invention a method of stored data retrieval. The method includes obtaining a stored data retrieval wavefront which has an amplitude and a phase, by reflecting radiation from the media in which information is encoded, by selecting the height of the media at each of a multiplicity of different locations on the media. Preferably, analyzing the stored data retrieval wavefront by: obtaining a plurality of differently phase changed transformed wavefronts corresponding to the stored data retrieval wavefront, obtaining a plurality of intensity maps of the plurality of phase changed transformed wavefronts and employing the plurality of intensity maps to obtain an indication of the amplitude and phase of the stored data retrieval wavefront and employing the indication of the amplitude and phase to obtain the information.

There is further provided in accordance with yet another preferred embodiment of the present invention an apparatus for stored data retrieval. The apparatus includes a wavefront obtainer operating to obtain a stored data retrieval wavefront which has an amplitude and a phase, by reflecting radiation from the media in which information is encoded by selecting the height of the media at each of a multiplicity of different locations on the media, a wavefront analyzer, analyzing the stored data retrieval wavefront and including a wavefront transformer operating to provide a plurality of differently phase changed transformed wavefronts corresponding to the stored data retrieval wavefront, an intensity map generator operating to obtain a plurality of intensity maps of the plurality of phase changed transformed wavefronts and an intensity map utilizer, employing the plurality of intensity maps to provide an indication of the amplitude and phase of the stored data retrieval wavefront and a phase and amplitude utilizer, employing the indication of the amplitude and phase to provide the information.

Preferably, the step of obtaining a plurality of differently phase changed transformed wavefronts includes: applying a transform to the stored data retrieval wavefront thereby to obtain a transformed wavefront and applying a plurality of different phase changes to the transformed wavefront, thereby to obtain a plurality of differently phase changed transformed wavefronts.

Further in accordance with a preferred embodiment of the present invention the transform applied to the stored data retrieval wavefront is a Fourier transform, the plurality of different phase changes includes at least three different phase changes, effected by applying a spatially uniform, time-varying spatial phase change to part of the transformed wavefront, the plurality of intensity maps includes at least three intensity maps and employing the plurality of intensity maps to obtain an output indicating the amplitude and phase of the stored data retrieval wavefront includes: expressing the stored data retrieval wavefront as a first complex function which has an amplitude and phase identical to the amplitude and phase of the stored data retrieval wavefront, expressing the plurality of intensity maps as a function of the first complex function and of a spatial function governing the spatially uniform, time-varying spatial phase change, defining a second complex function having an absolute value and a phase as a convolution of the first complex function and of a Fourier transform of the spatial function governing the spatially uniform, time-varying spatial phase change, expressing each of the plurality of intensity maps as a third function of: the amplitude of the stored data retrieval wavefront, the absolute value of the second complex function, a difference between the phase of the stored data retrieval wavefront and the phase of the second complex function and a known phase delay produced by one of the at least three different phase changes, corresponding to one of the at least three intensity maps, solving the third function to obtain the amplitude of the stored data retrieval wavefront, the absolute value of the second complex function and the difference between the phase of the stored data retrieval wavefront and the phase of the second complex function, solving the second complex function to obtain the phase of the second complex function and obtaining the phase of the stored data retrieval wavefront by adding the phase of the second complex function to the difference between the phase of the stored data retrieval wavefront and phase of the second complex function.

Still further in accordance with a preferred embodiment of the present invention the stored data retrieval wavefront includes at least one one-dimensional component, the transform applied to the data retrieval wavefront is a one-dimensional Fourier transform, performed in a dimension perpendicular to a direction of propagation of the data retrieval wavefront, thereby to obtain at least one one-dimensional component of the transformed wavefront in the dimension perpendicular to the direction of propagation, the plurality of differently phase changed transformed wavefronts are obtained by applying the plurality of different phase changes to each of the one-dimensional component, thereby obtaining at least one one-dimensional component of the plurality of phase changed transformed wavefronts and the plurality of intensity maps are employed to obtain an output indicating amplitude and phase of the one-dimensional component of the data retrieval wavefront.

Preferably, the plurality of different phase changes is applied to each of the at least one one-dimensional component by providing a relative movement between the media and a component generating spatially varying, time-constant phase changes, the relative movement being in a dimension perpendicular to the direction of propagation and to the dimension perpendicular to the direction of propagation.

Additionally in accordance with a preferred embodiment of the present invention the information is encoded on the media whereby: an intensity value is realized by reflection of light from each location on the media to lie within a predetermined range of values, the range corresponding an element of the information stored at the location and by employing the plurality of intensity maps, multiple intensity values are realized for each location, providing multiple elements of information for each location on the media.

Preferably, the plurality of differently phase changed transformed wavefronts include a plurality of wavefronts whose phase has been changed by applying an at least time varying phase change function to the stored data retrieval wavefront.

Further in accordance with a preferred embodiment of the present invention the stored data retrieval wavefront includes a plurality of different wavelength components and the plurality of differently phase changed transformed wavefronts are obtained by applying at least one phase change to the plurality of different wavelength components of the stored data retrieval wavefront.

Further in accordance with a preferred embodiment of the present invention the radiation which is reflected from the media includes a plurality of different wavelength components, resulting in the stored data retrieval wavefront including a plurality of different wavelength components and the plurality of differently phase changed transformed wavefronts are obtained by applying a phase change to the plurality of different wavelength components of the stored data retrieval wavefront.

Still further in accordance with a preferred embodiment of the present invention the information encoded by selecting the height of the media at each of a multiplicity of different locations on the media is also encoded by selecting the reflectivity of the media at each of a plurality of different locations on the media and employing the indication of the amplitude and phase to obtain the information includes employing the indication of the phase to obtain the information encoded by selecting the height of the media and employing the indication of the amplitude to obtain the information encoded by selecting the reflectivity of the media.

There is provided in accordance with another preferred embodiment of the present invention a method of 3-dimensional imaging. The method includes obtaining a 3-dimensional imaging wavefront, which has an amplitude and a phase, by reflecting radiation from an object to be viewed and analyzing the 3-dimensional imaging wavefront by: obtaining a plurality of differently phase changed transformed wavefronts corresponding to the 3-dimensional imaging wavefront, obtaining a plurality of intensity maps of the plurality of differently phase changed transformed wavefronts and employing the plurality of intensity maps to obtain an output indicating the amplitude and phase of the 3-dimensional imaging wavefront.

There is further provided in accordance with a preferred embodiment of the present invention an apparatus for 3-dimensional imaging. The apparatus includes a wavefront obtainer operating to obtain a 3-dimensional imaging wavefront, which has an amplitude and a phase, by reflecting radiation from an object to be viewed, a wavefront analyzer, analyzing the 3-dimensional imaging wavefront including a wavefront transformer operative to provide a plurality of differently phase changed transformed wavefronts corresponding to the 3-dimensional imaging wavefront, an intensity map generator operative to provide a plurality of intensity maps of the plurality of differently phase changed transformed wavefronts and an intensity map utilizer, employing the plurality of intensity maps to provide an output indicating the amplitude and phase of the 3-dimensional imaging wavefront.

Further in accordance with a preferred embodiment of the present invention the radiation reflected from the object has a narrow band about a given wavelength, causing the phase of the 3-dimensional imaging wavefront to be proportional to geometrical variations in the object, the proportion being an inverse linear function of the wavelength.

Additionally in accordance with a preferred embodiment of the present invention the step of obtaining a plurality of differently phase changed transformed wavefronts includes applying a transform to the 3-dimensional imaging wavefront, thereby to obtain a transformed wavefront and applying a plurality of different phase changes, including spatial phase changes, to the transformed wavefront, thereby to obtain a plurality of differently phase changed transformed wavefronts.

Still further in accordance with a preferred embodiment of the present invention the 3-dimensional imaging wavefront includes a plurality of different wavelength components and the plurality of differently phase changed transformed wavefronts are obtained by: transforming the 3-dimensional imaging wavefront, thereby obtaining a transformed wavefront including a plurality of different wavelength components and applying phase changes to the plurality of different wavelength components of the transformed wavefront by passing the transformed wavefront through an object, at least one of whose thickness and refractive index varies spatially.

There is also provided in accordance with yet another preferred embodiment of the present invention a method of wavefront analysis. The method includes obtaining a plurality of differently phase changed transformed wavefronts corresponding to a wavefront being analyzed, obtaining a plurality of intensity maps of the plurality of phase changed transformed wavefronts and employing the plurality of intensity maps to obtain an output indicating at least the phase of the wavefront being analyzed by combining the plurality of intensity maps into a second plurality of combined intensity maps, the second plurality being less than the first plurality, obtaining at least an output indicative of the phase of the wavefront being analyzed from each of the second plurality of combined intensity maps and combining the outputs to provide at least an enhanced indication of phase of the wavefront being analyzed.

There is also provided in accordance with yet another preferred embodiment of the present invention an apparatus wavefront analysis. The apparatus includes a wavefront transformer operating to provide a plurality of differently phase changed transformed wavefronts corresponding to a wavefront being analyzed, an intensity map generator operating to obtain a plurality of intensity maps of the plurality of phase changed transformed wavefronts and an intensity map utilizer, employing the plurality of intensity maps to obtain an output indicating at least amplitude of the wavefront being analyzed and including an intensity combiner operating to combine the plurality of intensity maps into a second plurality of combined intensity maps, the second plurality being less than the first plurality, an indication provider operating to provide at least an output indicative of the amplitude of the wavefront being analyzed from each of the second plurality of combined intensity maps and an enhanced indication provider, combining the outputs to provide at least an enhanced indication of amplitude of the wavefront being analyzed.

There is provided in accordance with a further preferred embodiment of the present invention a method of wavefront analysis. The method includes obtaining a plurality of differently phase changed transformed wavefronts corresponding to a wavefront being analyzed, obtaining a plurality of intensity maps of the plurality of phase changed transformed wavefront and employing the plurality of intensity maps to obtain an output indicating at least amplitude of the wavefront being analyzed by combining the plurality of intensity maps into a second plurality of combined intensity maps, the second plurality being less than the first plurality, obtaining at least an output indicative of the amplitude of the wavefront being analyzed from each of the second plurality of combined intensity maps and combining the outputs to provide at least an enhanced indication of amplitude of the wavefront being analyzed.

There is provided in accordance with a preferred embodiment of the present invention an apparatus for wavefront analysis. The apparatus includes a wavefront transformer operating to provide a plurality of differently phase changed transformed wavefronts corresponding to a wavefront being analyzed, an intensity map generator operating to provide a plurality of intensity maps of the plurality of phase changed transformed wavefronts and an intensity map utilizer, employing the plurality of intensity maps to provide an output indicating at least the phase of the wavefront being analyzed. Preferably, the apparatus also includes an intensity map expresser, expressing the plurality of intensity maps as a function of: amplitude of the wavefront being analyzed, phase of the wavefront being analyzed and a phase change function characterizing the plurality of differently phase changed transformed wavefronts, a complex function definer, defining a complex function of: the amplitude of the wavefront being analyzed, the phase of the wavefront being analyzed and the phase change function characterizing the plurality of differently phase changed transformed wavefronts, the complex function being characterized in that the intensity at each location in the plurality of intensity maps is a function predominantly of a value of the complex function at the location and of the amplitude and the phase of the wavefront being analyzed at the location. The apparatus also typically, includes complex function expresser, expressing the complex function as a function of the plurality of intensity maps and a phase obtainer, obtaining values for the phase by employing the complex function expressed as a function of the plurality of intensity maps.

There is also provided in accordance with another preferred embodiment of the present invention a method of wavefront analysis. The method includes obtaining a plurality of differently phase changed transformed wavefronts corresponding to a wavefront being analyzed, obtaining a plurality of intensity maps of the plurality of phase changed transformed wavefronts and employing the plurality of intensity maps to provide an output indicating at least the phase of the wavefront being analyzed by: expressing the plurality of intensity maps as a function of: amplitude of the wavefront being analyzed, phase of the wavefront being analyzed and a phase change function characterizing the plurality of differently phase changed transformed wavefronts. Additionally, defining a complex function of: the amplitude of the wavefront being analyzed, the phase of the wavefront being analyzed and the phase change function characterizing the plurality of differently phase changed transformed wavefronts, the complex function being characterized in that the intensity at each location in the plurality of intensity maps is a function predominantly of a value of the complex function at the location and of the amplitude and the phase of the wavefront being analyzed at the location, expressing the complex function as a function of the plurality of intensity maps and obtaining values for the phase by employing the complex function expressed as a function of the plurality of intensity maps.

There is further provided in accordance with yet a further preferred embodiment of the present invention a method of wavefront analysis. The method includes applying a Fourier transform to a wavefront being analyzed which has an amplitude and a phase, thereby obtaining a transformed wavefront, applying a spatially uniform time-varying spatial phase change to part of the transformed wavefront, thereby to obtain at least three differently phase changed transformed wavefronts, applying a second Fourier transform to obtain at least three intensity maps of the at least three phase changed transformed wavefronts and employing the at least three intensity maps to obtain an output indicating at least one of the phase and the amplitude of the wavefront being analyzed by: expressing the wavefront being analyzed as a first complex function which has an amplitude and phase identical to the amplitude and phase of the wavefront being analyzed, expressing the plurality of intensity maps as a function of the first complex function and of a spatial function governing the spatially uniform, time-varying spatial phase change, defining a second complex function having an absolute value and a phase as a convolution of the first complex function and of a Fourier transform of the spatial function governing the spatially uniform, time-varying spatial phase change, expressing each of the plurality of intensity maps as a third function of: the amplitude of the wavefront being analyzed, the absolute value of the second complex function, a difference between the phase of the wavefront being analyzed and the phase of the second complex function and a known phase delay produced by one of the at least three different phase changes, which each correspond to one of the at least three intensity maps, solving the third function to obtain the amplitude of the wavefront being analyzed, the absolute value of the second complex function and the difference between the phase of the wavefront being analyzed and the phase of the second complex function, solving the second complex function to obtain the phase of the second complex function and obtaining the phase of the wavefront being analyzed by adding the phase of the second complex function to the difference between the phase of the wavefront being analyzed and phase of the second complex function.

There is further provided in accordance with yet a further preferred embodiment of the present invention an apparatus for wavefront analysis. The apparatus includes a first transform applier, applying a Fourier transform to a wavefront being analyzed which has an amplitude and a phase thereby to obtain a transformed wavefront, a phase change applier, applying a spatially uniform time-varying spatial phase change to part of the transformed wavefront, thereby obtaining at least three differently phase changed transformed wavefronts, a second transform applier, applying a second Fourier transform to the at least three differently phase changed transformed wavefronts, thereby obtaining at least three intensity maps. The apparatus also typically includes an intensity map utilizer, employing the at least three intensity maps to provide an output indicating the phase and the amplitude of the wavefront being analyzed and a wavefront expresser, expressing the wavefront being analyzed as a first complex function which has an amplitude and phase identical to the amplitude and phase of the wavefront being analyzed, a first intensity map expresser, expressing the plurality of intensity maps as a function of the first complex function and of a spatial function governing the spatially uniform, time-varying spatial phase change. Preferably, the apparatus also includes a complex function definer, defining a second complex function having an absolute value and a phase as a convolution of the first complex function and of a Fourier transform of the spatial function governing the spatially uniform, time-varying spatial phase change, a second intensity map expresser, expressing each of the plurality of intensity maps as a third function of: the amplitude of the wavefront being analyzed, the absolute value of the second complex function, a difference between the phase of the wavefront being analyzed and the phase of the second complex function and a known phase delay produced by one of the at least three different phase changes, which each correspond to one of the at least three intensity maps. The apparatus further typically includes a first function solver, solving the third function to obtain the amplitude of the wavefront being analyzed, the absolute value of the second complex function and the difference between the phase of the wavefront being analyzed and the phase of the second complex function, a second function solver, solving the second complex function to obtain the phase of the second complex function and a phase obtainer, obtaining the phase of the wavefront being analyzed by adding the phase of the second complex function to the difference between the phase of the wavefront being analyzed and the phase of the second complex function.

BRIEF DESCRIPTION OF THE DRAWINGS

The present invention will be understood and appreciated more fully from the following detailed description, taken in conjunction with the drawings in which:

FIG. 1A is a simplified partially schematic, partially pictorial illustration of wavefront analysis functionality operative in accordance with a preferred embodiment of the present invention;

FIG. 10B is a simplified partially schematic, partially pictorial illustration of a wavefront analysis system suitable for carrying out the functionality of FIG. 10A in accordance with a preferred embodiment of the present invention;

FIG. 11 is a simplified functional block diagram illustration of the functionality of FIG. 1A where an additional transform is applied following the application of spatial phase changes;

FIG. 21A is a simplified partially schematic, partially pictorial illustration of wavefront analysis functionality operative in accordance with another preferred embodiment of the present invention;

FIG. 21B is a simplified partially schematic, partially block diagram illustration of a wavefront analysis system suitable for carrying out the functionality of FIG. 21A in accordance with another preferred embodiment of the present invention; and FIG. 22 is a simplified partially schematic, partially pictorial illustration of a system for surface mapping employing the functionality and structure of FIGS. 21A and 21B.

DETAILED DESCRIPTION OF PREFERRED EMBODIMENTS

Figure 1B:
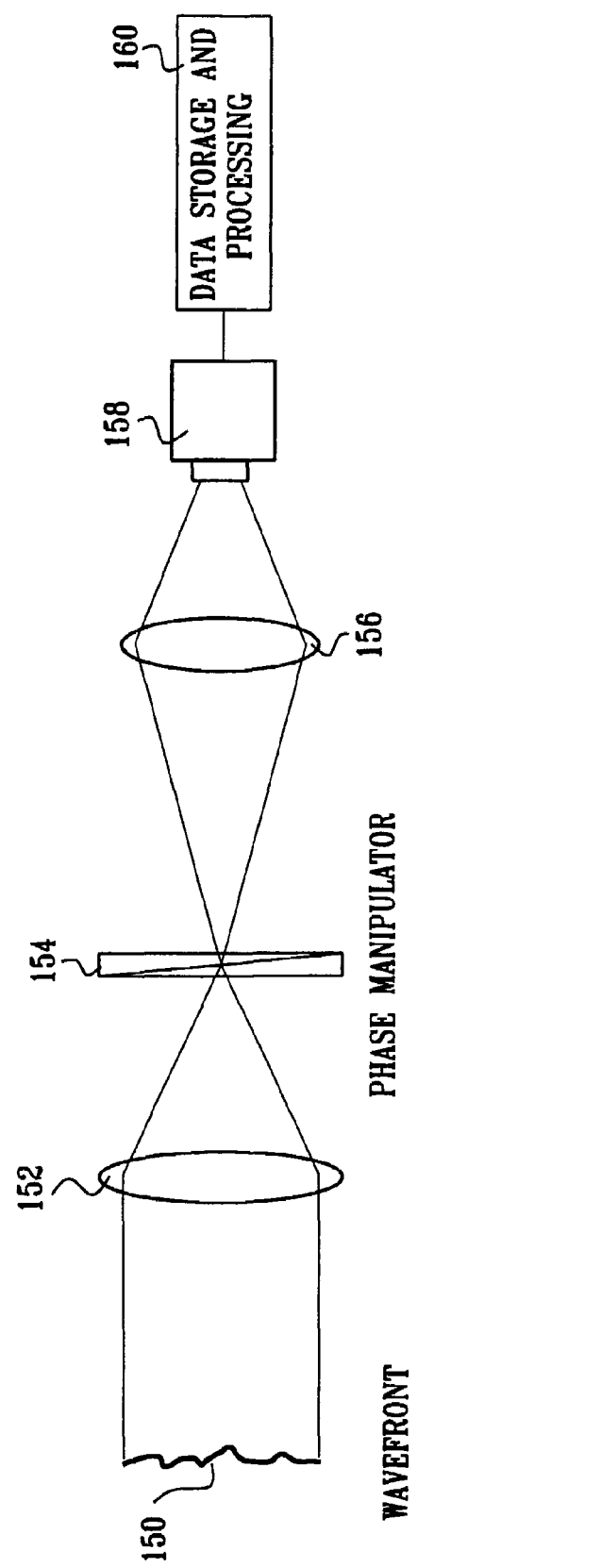
FIG. 1B is a simplified partially schematic, partially block diagram illustration of a wavefront analysis system suitable for carrying out the functionality of FIG. 1A in accordance with a preferred embodiment of the present invention.

Reference is now made to FIG. 1A, which is a simplified partially schematic, partially pictorial illustration of wavefront analysis functionality operative in accordance with a preferred embodiment of the present invention. The functionality of FIG. 1A can be summarized as including the following sub-functionalities:

A. obtaining a plurality of differently phase changed transformed wavefronts corresponding to a wavefront being analyzed, which has an amplitude and a phase;

B. obtaining a plurality of intensity maps of the plurality of phase changed transformed wavefronts; and C. employing the plurality of intensity maps to obtain an output indicating at least one and possibly both of the phase and the amplitude of the wavefront being analyzed.

As seen in FIG. 1A, the first sub-functionality, designated "A" may be realized by the following functionalities:

A wavefront, which may be represented by a plurality of point sources of light, is generally designated by reference numeral 100. Wavefront 100 has a phase characteristic which is typically spatially non-uniform, shown as a solid line and indicated generally by reference numeral 102. Wavefront 100 also has an amplitude characteristic which is also typically spatially non-uniform, shown as a dashed line and indicated generally by reference numeral 103. Such a wavefront may be obtained in a conventional manner by receiving light from any object, such as by reading an optical disk, for example a DVD or compact disk 104.

A principal purpose of the present invention is to measure the phase characteristic, such as that indicated by reference numeral 102, which is not readily measured. Another purpose of the present invention is to measure the amplitude characteristic, such as that indicated by reference numeral 103 in an enhanced manner. A further purpose of the present invention is to measure both the phase characteristic 102 and the amplitude characteristic 103. While there exist various techniques for carrying out such measurements, the present invention provides a methodology which is believed to be superior to those presently known, inter alia due to its relative insensitivity to noise.

A transform, indicated here symbolically by reference numeral 106, is applied to the wavefront being analyzed 100, thereby to obtain a transformed wavefront. A preferred transform is a Fourier transform. The resulting transformed wavefront is symbolically indicated by reference numeral 108.

A plurality of different phase changes, preferably spatial phase changes, represented by optical path delays 110, 112 and 114 are applied to the transformed wavefront 108, thereby to obtain a plurality of differently phase changed transformed wavefronts, represented by reference numerals 120, 122 and 124 respectively. It is appreciated that the illustrated difference between the individual ones of the plurality of differently phase changed transformed wavefronts is that portions of the transformed wavefront are delayed differently relative to the remainder thereof. The difference in the phase changes, which are applied to the transformed wavefront 108, is represented in FIG. 1A by the change in thickness of the optical path delays 110, 112 and 114.

As seen in FIG. 1A, the second sub-functionality, designated "B", may be realized by applying a transform, preferably a Fourier transform, to the plurality of differently phase changed transformed wavefronts. Alternatively, the sub-functionality B may be realized without the use of a Fourier transform, such as by propagation of the differently phase changed transformed wavefronts over an extended space. Finally, functionality B requires detection of the intensity characteristics of plurality of differently phase changed transformed wavefronts. The outputs of such detection are the intensity maps, examples of which are designated by reference numerals 130, 132 and 134.

As seen in FIG. 1A, the third sub-functionality, designated "C" may be realized by the following functionalities:

expressing, such as by employing a computer 136, the plurality of intensity maps, such as maps 130, 132 and 134, as at least one mathematical function of phase and amplitude of the wavefront being analyzed and of the plurality of different phase changes, wherein at least one and possibly both of the phase and the amplitude are unknown and the plurality of different phase changes, typically represented by optical path delays 110, 112 and 114 to the transformed wavefront 108, are known; and employing, such as by means of the computer 136, the at least one mathematical function to obtain an indication of at least one and possibly both of the phase and the amplitude of the wavefront being analyzed, here represented by the phase function designated by reference numeral 138 and the amplitude function designated by reference numeral 139, which, as can be seen, respectively represent the phase characteristics 102 and the amplitude characteristics 103 of the wavefront 100. In this example, wavefront 100 may represent the information contained in the compact disk or DVD 104.

In accordance with an embodiment of the present invention, the plurality of intensity maps comprises at least four intensity maps. In such a case, employing the plurality of intensity maps to obtain an output indicating at least the phase of the wavefront being analyzed includes employing a plurality of combinations, each of at least three of the plurality of intensity maps, to provide a plurality of indications at least of the phase of the wavefront being analyzed.

Preferably, the methodology also includes employing the plurality of indications of at least the phase of the wavefront being analyzed to provide an enhanced indication at least of the phase of the wavefront being analyzed.

Also in accordance with an embodiment of the present invention, the plurality of intensity maps comprises at least four intensity maps. In such a case, employing the plurality of intensity maps to obtain an output indicating at least the amplitude of the wavefront being analyzed includes employing a plurality of combinations, each of at least three of the plurality of intensity maps, to provide a plurality of indications at least of the amplitude of the wavefront being analyzed.

Preferably, the methodology also includes employing the plurality of indications of at least the amplitude of the wavefront being analyzed to provide an enhanced indication at least of the amplitude of the wavefront being analyzed.

It is appreciated that in this manner, enhanced indications of both phase and amplitude of the wavefront may be obtained.

In accordance with a preferred embodiment of the present invention, at least some of the plurality of indications of the amplitude and phase are at least second order indications of the amplitude and phase of the wavefront being analyzed.

In accordance with one preferred embodiment of the present invention, the plurality of intensity maps are employed to provide an analytical output indicating the amplitude and phase.

Preferably, the phase changed transformed wavefronts are obtained by interference of the wavefront being analyzed along a common optical path.

In accordance with one preferred embodiment of the present invention, the plurality of differently phase changed transformed wavefronts are realized in a manner substantially different from performing a delta-function phase change to the transformed wavefront, whereby a delta-function phase change is applying a uniform phase delay to a small spatial region, having the characteristics of a delta-function, of the transformed wavefront.

In accordance with another preferred embodiment of the present invention, the plurality of intensity maps are employed to obtain an output indicating the phase of the wavefront being analyzed, which is substantially free from halo and shading off distortions, which are characteristic of many of the existing 'phase-contrast' methods.

In accordance with another embodiment of the present invention the output indicating the phase of the wavefront being analyzed may be processed to obtain the polarization mode of the wavefront being analyzed.

In accordance with still another embodiment of the present invention, the plurality of intensity maps may be employed to obtain an output indicating the phase of the wavefront being analyzed by combining the plurality of intensity maps into a second plurality of combined intensity maps, the second plurality being less than the first plurality, obtaining at least an output indicative of the phase of the wavefront being analyzed from each of the second plurality of combined intensity maps and combining the outputs to provide an enhanced indication of the phase of the wavefront being analyzed.

In accordance with yet another embodiment of the present invention, the plurality of intensity maps may be employed to obtain an output indicating amplitude of the wavefront being analyzed by combining the plurality of intensity maps into a second plurality of combined intensity maps, the second plurality being less than the first plurality, obtaining at least an output indicative of the amplitude of the wavefront being analyzed from each of the second plurality of combined intensity maps and combining the outputs to provide an enhanced indication of the amplitude of the wavefront being analyzed.

Additionally in accordance with a preferred embodiment of the present invention, the foregoing methodology may be employed for obtaining a plurality of differently phase changed transformed wavefronts corresponding to a wavefront being analyzed, obtaining a plurality of intensity maps of the plurality of phase changed transformed wavefronts and employing the plurality of intensity maps to obtain an output of an at least second order indication of phase of the wavefront being analyzed.

Additionally or alternatively in accordance with a preferred embodiment of the present invention, the foregoing methodology may be employed for obtaining a plurality of differently phase changed transformed wavefronts corresponding to a wavefront being analyzed, obtaining a plurality of intensity maps of the plurality of phase changed transformed wavefronts and employing the plurality of intensity maps to obtain an output of an at least second order indication of amplitude of the wavefront being analyzed.

In accordance with yet another embodiment of the present invention, the obtaining of the plurality of differently phase changed transformed wavefronts comprises applying a transform to the wavefront being analyzed, thereby to obtain a transformed wavefront, and then applying a plurality of different phase and amplitude changes to the transformed wavefront, where each of these changes can be a phase change, an amplitude change or a combined phase and amplitude change, thereby to obtain a plurality of differently phase and amplitude changed transformed wavefronts.

In accordance with yet another embodiment of the present invention, a wavefront being analyzed comprises at least two wavelength components. In such a case, obtaining a plurality of intensity maps also includes dividing the phase changed transformed wavefronts according to the at least two wavelength components in order to obtain at least two wavelength components of the phase changed transformed wavefronts and in order to obtain at least two sets of intensity maps, each set corresponding to a different one of the at least two wavelength components of the phase changed transformed wavefronts.

Subsequently, the plurality of intensity maps are employed to provide an output indicating the amplitude and phase of the wavefront being analyzed by obtaining an output indicative of the phase of the wavefront being analyzed from each of the at least two sets of intensity maps and combining the outputs to provide an enhanced indication of phase of the wavefront being analyzed. In the enhanced indication, there is no $2\pi$ ambiguity once the value of the phase exceeds $2\pi$, which conventionally results when detecting a phase of a single wavelength wavefront.

It is appreciated that the wavefront being analyzed may be an acoustic radiation wavefront.

It is also appreciated that the wavefront being analyzed may be an electromagnetic radiation wavefront, of any suitable wavelength, such as visible light, infrared, ultraviolet and X-ray radiation.

It is further appreciated that wavefront 100 may be represented by a relatively small number of point sources and defined over a relatively small spatial region. In such a case, the detection of the intensity characteristics of the plurality of differently phase changed transformed wavefronts may be performed by a detector comprising only a single detection pixel or several detection pixels. Additionally, the output indicating at least one and possibly both of the phase and amplitude of the wavefront being analyzed, may be provided by computer 136 in a straight-forward manner.

Reference is now made to FIG. 1B, which is a simplified partially schematic, partially block diagram illustration of a wavefront analysis system suitable for carrying out the functionality of FIG. 1A in accordance with a preferred embodiment of the present invention. As seen in FIG. 1B, a wavefront, here designated by reference numeral 150 is focused, as by a lens 152, onto a phase manipulator 154, which is preferably located at the focal plane of lens 152. The phase manipulator 154 generates phase changes, and may be, for example, a spatial light modulator or a series of different transparent, spatially non-uniform objects.

A second lens 156 is arranged so as to image wavefront 150 onto a detector 158, such as a CCD detector. Preferably the second lens 156 is arranged such that the detector 158 lies in its focal plane. The output of detector 158 is preferably supplied to data storage and processing circuitry 160, which preferably carries out functionality "C" described hereinabove with reference to FIG. 1A.

Figure 2:
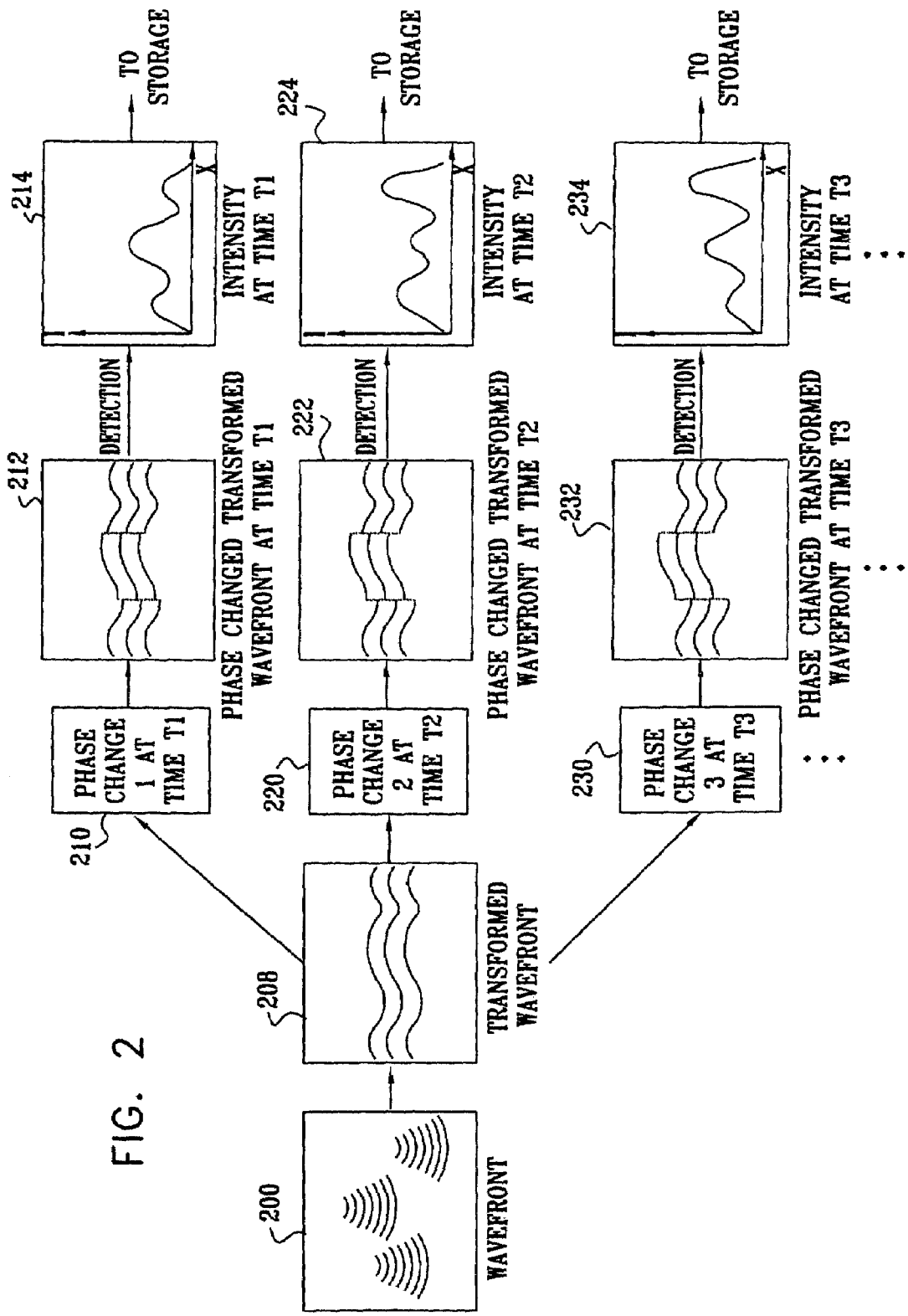
FIG. 2 is a simplified functional block diagram illustration of the functionality of FIG. 1A where time-varying phase changes are applied to a transformed wavefront.

Reference is now made to FIG. 2, which is a simplified functional block diagram illustration of the functionality of FIG. 1A where time-varying phase changes are applied to a transformed wavefront. As seen in FIG. 2, and as explained hereinabove with reference to FIG. 1A, a wavefront 200 is preferably transformed to provide a transformed wavefront 208.

A first phase change, preferably a spatial phase change, is applied to the transformed wavefront 208 at a first time T1, as indicated by reference numeral 210, thereby producing a phase changed transformed wavefront 212 at time T1. This phase changed transformed wavefront 212 is detected, as by detector 158 (FIG. 1B), producing an intensity map, an example of which is designated by reference numeral 214, which map is stored as by circuitry 160 (FIG. 1B).

Thereafter, a second phase change, preferably a spatial phase change, is applied to the transformed wavefront 208 at a second time T2, as indicated by reference numeral 220, thereby producing a phase changed transformed wavefront 222 at time T2. This phase changed transformed wavefront 222 is detected, as by detector 158 (FIG. 1B), producing an intensity map, an example of which is designated by reference numeral 224, which map is stored as by circuitry 160 (FIG. 1B).

Thereafter, a third phase change, preferably a spatial phase change, is applied to the transformed wavefront 208 at a third time T3, as indicated by reference numeral 230, thereby producing a phase changed transformed wavefront 232 at time T3. This phase changed transformed wavefront 232 is detected, as by detector 158 (FIG. 1B), producing an intensity map, an example of which is designated by reference numeral 234, which map is stored as by circuitry 160 (FIG. 1B).

It is appreciated that any suitable number of spatial phase changes may be made at successive times and stored for use in accordance with the present invention.

In accordance with a preferred embodiment of the present invention, at least some of the phase changes 210, 220 and 230, are spatial phase changes effected by applying a spatial phase change to part of the transformed wavefront 208.

In accordance with another preferred embodiment of the present invention, at least some of the phase changes 210, 220 and 230, are spatial phase changes effected by applying a time-varying spatial phase change to part of the transformed wavefront 208.

In accordance with another preferred embodiment of the present invention, at least some of the phase changes 210, 220 and 230, are spatial phase changes effected by applying a non time-varying spatial phase change to part of transformed wavefront 208, producing spatially phase changed transformed wavefronts 212, 222 and 232, which subsequently produce spatially varying intensity maps 214, 224 and 234 respectively.

Figure 3:
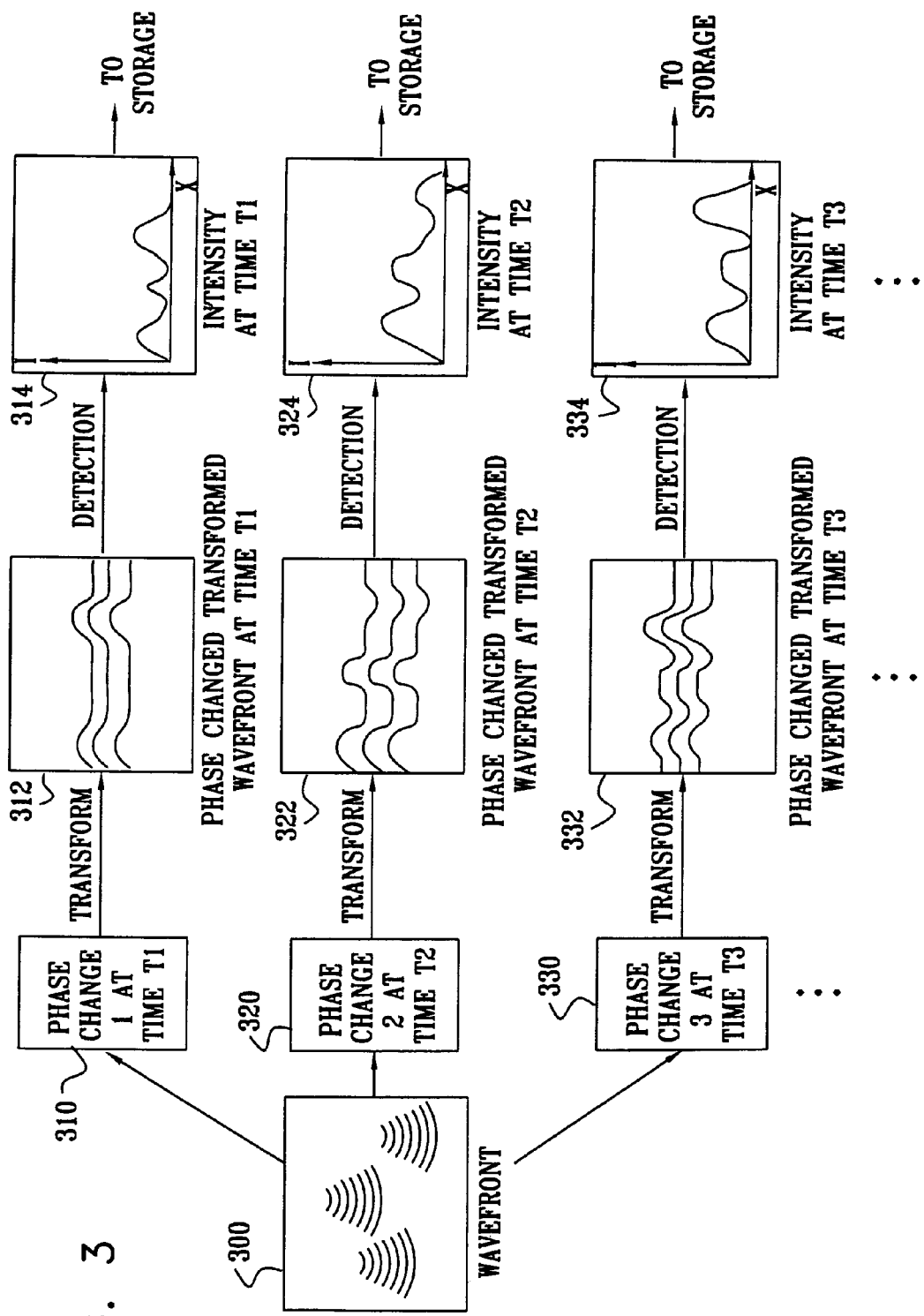
FIG. 3 is a simplified functional block diagram illustration of the functionality of FIG. 1A where time-varying phase changes are applied to a wavefront prior to transforming thereof.

Reference is now made to FIG. 3, which is a simplified functional block diagram illustration of the functionality of FIG. 1A where time-varying phase changes are applied to a wavefront prior to transforming thereof. As seen in FIG. 3, a first phase change, preferably a spatial phase change, is applied to a wavefront 300 at a first time T1, as indicated by reference numeral 310. Following application of the first phase change to wavefront 300, a transform, preferably a Fourier transform, is applied thereto, thereby producing a phase changed transformed wavefront 312 at time T1. This phase changed transformed wavefront 312 is detected, as by detector 158 (FIG. 1B), producing an intensity map, an example of which is designated by reference numeral 314, which map is stored as by circuitry 160 (FIG. 1B).

Thereafter, a second phase change, preferably a spatial phase change, is applied to wavefront 300 at a second time T2, as indicated by reference numeral 320. Following application of the second phase change to wavefront 300, a transform, preferably a Fourier transform, is applied thereto, thereby producing a phase changed transformed wavefront 322 at time T2. This phase changed transformed wavefront 322 is detected, as by detector 158 (FIG. 1B), producing an intensity map, an example of which is designated by reference numeral 324, which map is stored as by circuitry 160 (FIG. 1B).

Thereafter, a third phase change, preferably a spatial phase change, is applied to wavefront 300 at a third time T3, as indicated by reference numeral 330. Following application of the third phase change to wavefront 300, a transform, preferably a Fourier transform, is applied thereto, thereby producing a phase changed transformed wavefront 332 at time T3. This phase changed transformed wavefront 332 is detected, as by detector 158 (FIG. 1B), producing an intensity map, an example of which is designated by reference numeral 334, which map is stored as by circuitry 160 (FIG. 1B).

It is appreciated that any suitable number of spatial phase changes may be made at successive times and stored for use in accordance with the present invention.

In accordance with a preferred embodiment of the present invention, at least some of the phase changes 310, 320 and 330, are spatial phase changes effected by applying a spatial phase change to part of wavefront 300.

In accordance with another preferred embodiment of the present invention, at least some of the phase changes 310, 320 and 330, are spatial phase changes, effected by applying a time-varying spatial phase change to part of wavefront 300.

In accordance with another preferred embodiment of the present invention, at least some of the phase changes 310, 320 and 330, are spatial phase changes, effected by applying a non time-varying spatial phase change to part of wavefront 300, producing spatially phase changed transformed wavefronts 312, 322 and 332, which subsequently produce spatially varying intensity maps 314, 324 and 334 respectively.

Figure 4:
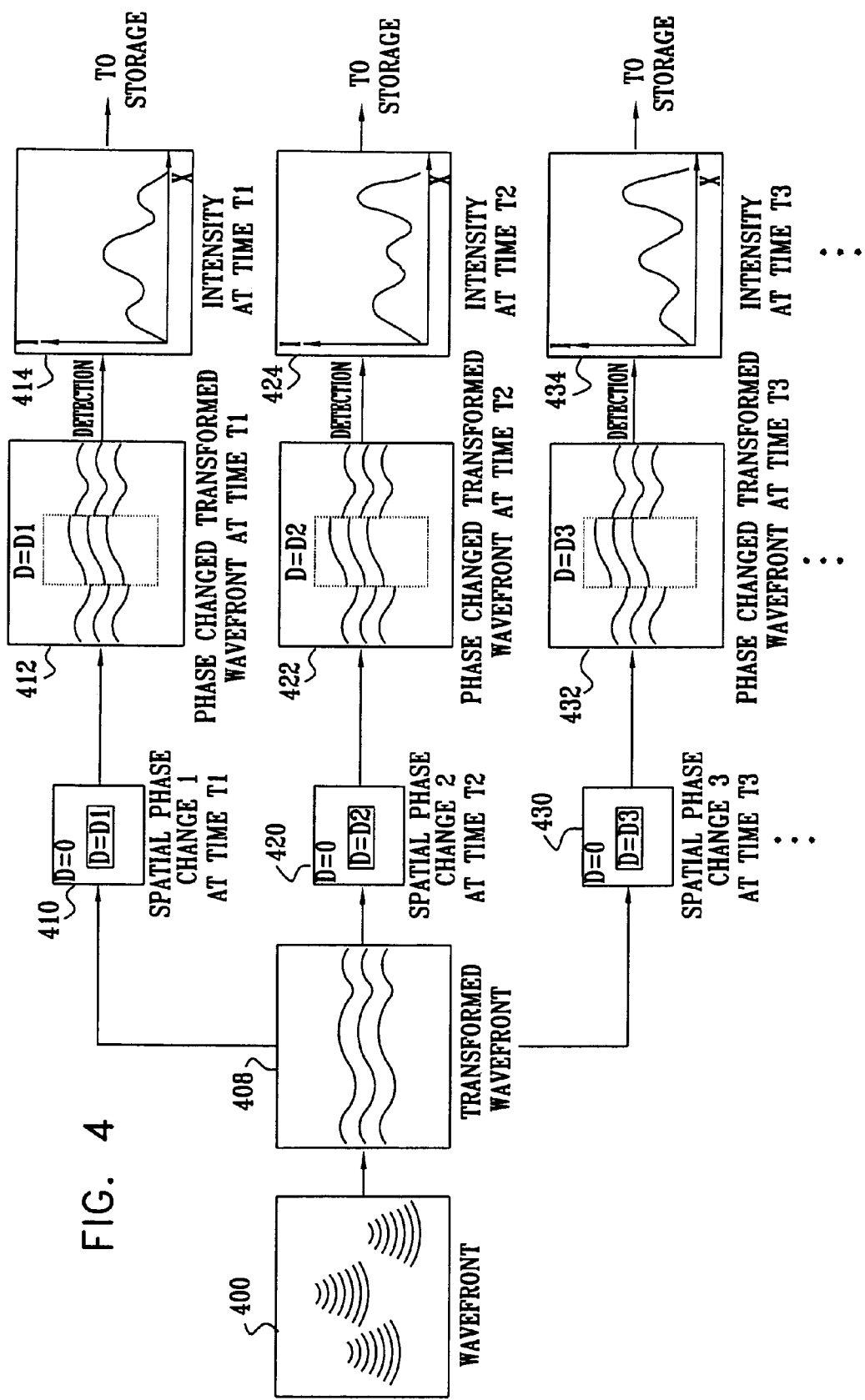
FIG. 4 is a simplified functional block diagram illustration of the functionality of FIG. 2 where time-varying, non-spatially varying spatial phase changes are applied to a transformed wavefront.

Reference is now made to FIG. 4, which is a simplified functional block diagram illustration of the functionality of FIG. 2, specifically in a case where time-varying, non-spatially varying, spatial phase changes are applied to a transformed wavefront. As seen in FIG. 4, and as explained hereinabove with reference to FIG. 1A, a wavefront 400 is preferably transformed to provide a transformed wavefront 408. A preferred transform is a Fourier transform.

A first spatial phase change is applied to the transformed wavefront 408 at a first time T1, as indicated by reference numeral 410. This phase change preferably is effected by applying a spatially uniform spatial phase delay D, designated by reference 'D=D1', to a given spatial region of the transformed wavefront 408. Thus, at the given spatial region of the transformed wavefront, the value of the phase delay at time T1 is D1, while at the remainder of the transformed wavefront, where no phase delay is applied, the value of the phase delay is D=0.

The first spatial phase change 410 thereby produces a spatially phase changed transformed wavefront 412 at time T1. This spatially phase changed transformed wavefront 412 is detected, as by detector 158 (FIG. 1B), producing a spatially varying intensity map, an example of which is designated by reference numeral 414, which map is stored as by circuitry 160 (FIG. 1B).

Thereafter, a second spatial phase change is applied to the transformed wavefront 408 at a second time T2, as indicated by reference numeral 420. This phase change preferably is effected by applying a spatially uniform spatial phase delay D, designated by reference 'D=D2', to a given spatial region of the transformed wavefront 408. Thus, at the given spatial region of the transformed wavefront, the value of the phase delay at time T2 is D2, while at the remainder of the transformed wavefront, where no phase delay is applied, the value of the phase delay is D=0.

The second spatial phase change 420 thereby produces a spatially phase changed transformed wavefront 422 at time T2. This spatially phase changed transformed wavefront 422 is detected, as by detector 158 (FIG. 1B), producing a spatially varying intensity map, an example of which is designated by reference numeral 424, which map is stored as by circuitry 160 (FIG. 1B).

Thereafter, a third spatial phase change is applied to the transformed wavefront 408 at a third time T3, as indicated by reference numeral 430. This phase change preferably is effected by applying a spatially uniform spatial phase delay D, designated by reference 'D=D3', to a given spatial region of the transformed wavefront 408. Thus, at the given spatial region of the transformed wavefront, the value of the phase delay at time T3 is D3, while at the remainder of the transformed wavefront, where no phase delay is applied, the value of the phase delay is D=0.

The third spatial phase change 430 thereby produces a spatially phase changed transformed wavefront 432 at time T3. This spatially phase changed transformed wavefront 432 is detected, as by detector 158 (FIG. 1B), producing a spatially varying intensity map, an example of which is designated by reference numeral 434, which map is stored as by circuitry 160 (FIG. 1B).

It is appreciated that any suitable number of spatial phase changes may be made at successive times and stored for use in accordance with the present invention.

In accordance with a preferred embodiment of the present invention, the transform applied to the wavefront 400 is a Fourier transform, thereby providing a Fourier-transformed wavefront 408. In addition, the plurality of phase changed transformed wavefronts 412, 422 and 432 may be further transformed, preferably by a Fourier transform, prior to detection thereof.

In accordance with a preferred embodiment of the present invention, the spatial region of the transformed wavefront 408 to which the spatially uniform, spatial phase delays D1, D2 and D3 are applied at times T1, T2 and T3 respectively is a spatially central region of the transformed wavefront 408.

In accordance with an embodiment of the present invention, a phase component comprising relatively high frequency components may be added to the wavefront 400 prior to applying the transform thereto, in order to increase the high-frequency content of the transformed wavefront 408 prior to applying the spatially uniform, spatial phase delays to a spatial region thereof.

Additionally, in accordance with a preferred embodiment of the present invention, the spatial region of the transformed wavefront 408 to which the spatially uniform, spatial phase delays D1, D2 and D3 are applied at times T1, T2 and T3 respectively is a spatially central region of the transformed wavefront 408, the transform applied to the wavefront 400 is a Fourier transform, and the plurality of phase changed transformed wavefronts 412, 422 and 432 are Fourier transformed prior to detection thereof.

In accordance with another embodiment of the present invention, the region of the transformed wavefront 408 to which the spatially uniform, spatial phase delays D1, D2 and D3 are applied at times T1, T2 and T3 respectively is a spatially centered generally circular region of the transformed wavefront 408.

In accordance with yet another embodiment of the present invention, the region of the transformed wavefront 408 to which the spatially uniform, spatial phase delays D1, D2 and D3 are applied at times T1, T2 and T3 respectively is a region covering approximately one half of the entire region in which transformed wavefront 408 is defined.

In accordance with a preferred embodiment of the present invention, the transformed wavefront 408 includes a non-spatially modulated region, termed a DC region, which represents an image of a light source generating the wavefront 400, and a non-DC region. The region of the transformed wavefront 408 to which the spatially uniform, spatial phase delays D1, D2 and D3 are applied at times T1, T2 and T3 respectively includes at least parts of both the DC region and the non-DC region.

Figure 5:
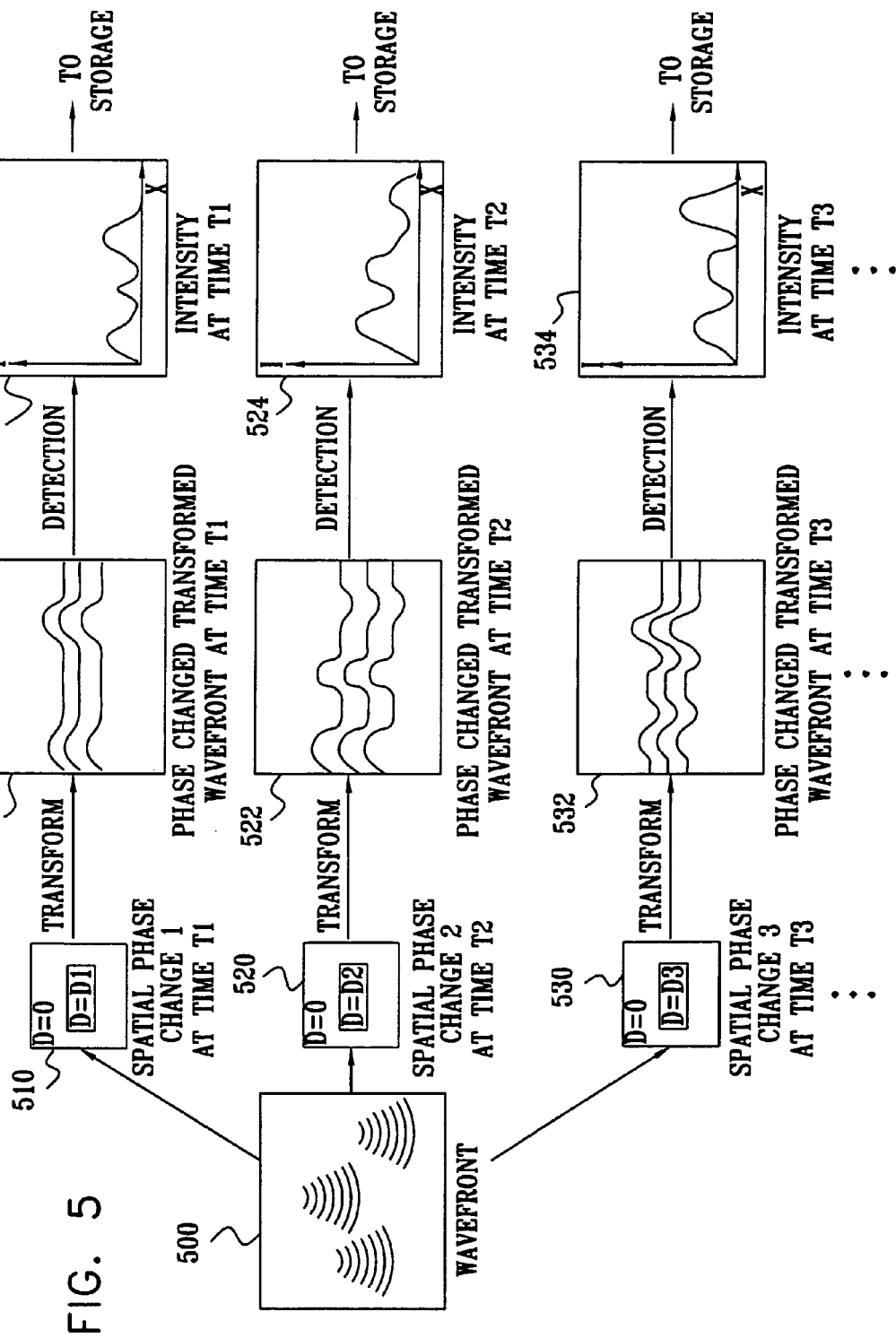
FIG. 5 is a simplified functional block diagram illustration of the functionality of FIG. 3 where time-varying, non-spatially varying spatial phase changes are applied to a wavefront prior to transforming thereof.

Reference is now made to FIG. 5, which is a simplified functional block diagram illustration of the functionality of FIG. 3, where time-varying, non-spatially varying, spatial phase changes are applied to a wavefront prior to transforming thereof.

As seen in FIG. 5, a first spatial phase change is applied to a wavefront 500 at a first time T1, as indicated by reference numeral 510. This phase change preferably is effected by applying a spatially uniform spatial phase delay D, designated by reference 'D=D1', to a given spatial region of the wavefront 500. Thus, at the given spatial region of the wavefront, the value of the phase delay at time T1 is D1, while at the remainder of the wavefront, where no phase delay is applied, the value of the phase delay is D=0.

Following application of the first spatial phase change to wavefront 500, a transform, preferably a Fourier transform, is applied thereto, thereby producing a spatially phase changed transformed wavefront 512 at time T1. This spatially phase changed transformed wavefront 512 is detected, as by detector 158 (FIG. 1B), producing a spatially varying intensity map, an example of which is designated by reference numeral 514, which map is stored as by circuitry 160 (FIG. 1B).

Thereafter, a second spatial phase change is applied to wavefront 500 at a second time T2, as indicated by reference numeral 520. This phase change preferably is effected by applying a spatially uniform spatial phase delay D, designated by reference 'D=D2', to a given spatial region of the wavefront 500. Thus, at the given spatial region of the wavefront, the value of the phase delay at time T2 is D2, while at the remainder of the wavefront, where no phase delay is applied, the value of the phase delay is D=0.

Following application of the second spatial phase change to wavefront 500, a transform, preferably a Fourier transform, is applied thereto, thereby producing a spatially phase changed transformed wavefront 522 at time T2. This spatially phase changed transformed wavefront 522 is detected, as by detector 158 (FIG. 1B), producing a spatially varying intensity map, an example of which is designated by reference numeral 524, which map is stored as by circuitry 160 (FIG. 1B).

Thereafter, a third spatial phase change is applied to wavefront 500 at a third time T3, as indicated by reference numeral 530. This phase change preferably is effected by applying a spatially uniform spatial phase delay D, designated by reference 'D=D3', to a given spatial region of the wavefront 500. Thus, at the given spatial region of the wavefront, the value of the phase delay at time T3 is D3, while at the remainder of the wavefront, where no phase delay is applied, the value of the phase delay is D=0.

Following application of the third spatial phase change to wavefront 500, a transform, preferably a Fourier transform, is applied thereto, thereby producing a spatially phase changed transformed wavefront 532 at time T3. This spatially phase changed transformed wavefront 532 is detected, as by detector 158 (FIG. 1B), producing a spatially varying intensity map, an example of which is designated by reference numeral 534, which map is stored as by circuitry 160 (FIG. 1B).

It is appreciated that any suitable number of spatial phase changes may be made at successive times and stored for use in accordance with the present invention.

In accordance with a preferred embodiment of the present invention, the spatial region of the wavefront 500 to which the spatially uniform, spatial phase delays D1, D2 and D3 are applied at times T1, T2 and T3 respectively is a spatially central region of the wavefront 500.

In accordance with an embodiment of the present invention, a phase component comprising relatively high frequency components may be added to the wavefront 500 prior to applying the spatial phase changes thereto, in order to increase the high-frequency content of the wavefront 500.

Additionally, in accordance with a preferred embodiment of the present invention, the spatial region of the wavefront 500 to which the spatially uniform, spatial phase delays D1, D2 and D3 are applied at times T1, T2 and T3 respectively is a spatially central region of the wavefront 500, the transforms are Fourier transforms, and the plurality of phase changed transformed wavefronts 512, 522 and 532 are Fourier transformed prior to detection thereof.

In accordance with another embodiment of the present invention, the region of the wavefront 500 to which the spatially uniform, spatial phase delays D1, D2 and D3 are applied at times T1, T2 and T3 respectively is a spatially centered generally circular region of the wavefront 500.

In accordance with yet another embodiment of the present invention, the region of the wavefront 500 to which the spatially uniform, spatial phase delays D1, D2 and D3 are applied at times T1, T2 and T3 respectively is a region covering approximately one half of the entire region in which wavefront 500 is defined.

In accordance with a preferred embodiment of the present invention, the wavefront 500 includes a non-spatially modulated region, termed a DC region, which represents an image of a light source generating the wavefront 500, and a non-DC region. The region of the wavefront 500 to which the spatially uniform, spatial phase delays D1, D2 and D3 are applied at times T1, T2 and T3 respectively includes at least parts of both the DC region and the non-DC region.

Figure 6:
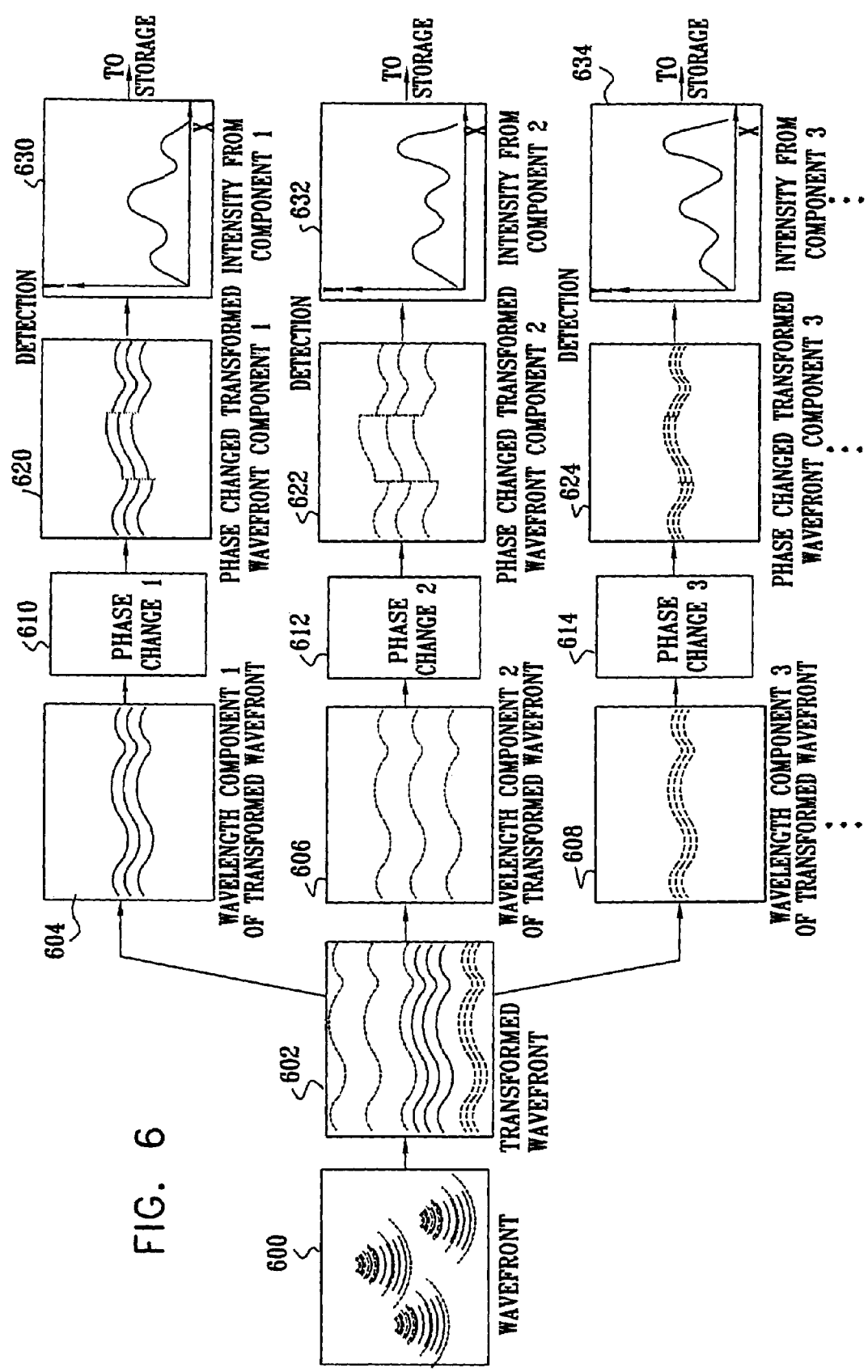
FIG. 6 is a simplified functional block diagram illustration of the functionality of FIG. 1A where phase changes are applied to a plurality of different wavelength components of a transformed wavefront.

Reference is now made to FIG. 6, which is a simplified functional block diagram illustration of the functionality of FIG. 1A where phase changes are applied to a plurality of different wavelength components of a transformed wavefront. As seen in FIG. 6, a wavefront 600, which comprises a plurality of different wavelength components, is preferably transformed to obtain a transformed wavefront 602. The transform is preferably a Fourier transform.

Similarly to wavefront 600, the transformed wavefront 602 also includes a plurality of different wavelength components, represented by reference numerals 604, 606 and 608. It is appreciated that both the wavefront 600 and the transformed wavefront 602 can include any suitable number of wavelength components.

A plurality of phase changes, preferably spatial phase changes, represented by reference numerals 610, 612 and 614 are applied to respective wavelength components 604, 606 and 608 of the transformed wavefront, thereby providing a plurality of differently phase changed transformed wavefront components, represented by reference numerals 620, 622 and 624 respectively.

The phase changed transformed wavefront components 620, 622, and 624 may be transformed, preferably by a Fourier transform, and are subsequently detected, as by detector 158 (FIG. 1B), producing spatially varying intensity maps, examples of which are designated by reference numerals 630, 632 and 634 respectively. These intensity maps are subsequently stored as by circuitry 160 (FIG. 1B).

In accordance with an embodiment of the present invention, phase changes 610, 612 and 614 are effected by passing the transformed wavefront 602 through an object, at least one of whose thickness and refractive index varies spatially, thereby applying a different spatial phase delay to each of the wavelength components 604, 606 and 608 of the transformed wavefront.

In accordance with another embodiment of the present invention, the phase changes 610, 612 and 614 are effected by reflecting the transformed wavefront 602 from a spatially varying surface, thereby applying a different spatial phase delay to each of the wavelength components 604, 606 and 608 of the transformed wavefront.

In accordance with yet another embodiment of the present invention, the phase changes 610, 612 and 614 are realized by passing the transformed wavefront 602 through a plurality of objects, each characterized in that at least one of its thickness and refractive index varies spatially. The spatial variance of the thickness or of the refractive index of the plurality of objects is selected in a way such that the phase changes 610, 612 and 614 differ to a selected predetermined extent for at least some of the plurality of different wavelength components 604, 606 and 608.

Alternatively, the spatial variance of the thickness or refractive index of the plurality of objects is selected in a way such that the phase changes 610, 612 and 614 are identical for at least some of the plurality of different wavelength components 604, 606 and 608.

Additionally, in accordance with an embodiment of the present invention, the phase changes 610, 612 and 614 are time-varying spatial phase changes. In such a case, the plurality of phase changed transformed wavefront components 620, 622 and 624 include a plurality of differently phase changed transformed wavefronts for each wavelength component thereof, and the intensity maps 630, 632 and 634 include a time-varying intensity map for each such wavelength component.

In accordance with an embodiment of the present invention, termed a "white light" embodiment, all the wavelength components may be detected by a single detector, resulting in a time-varying intensity map representing several wavelength components.

In accordance with another embodiment of the present invention, the plurality of phase changed transformed wavefront components 620, 622 and 624 are broken down into separate wavelength components, such as by a spatial separation effected, for example, by passing the phase changed transformed wavefront components through a dispersion element. In such a case, the intensity maps 630, 632 and 634 are provided simultaneously for all of the plurality of different wavelength components.

Figure 7:
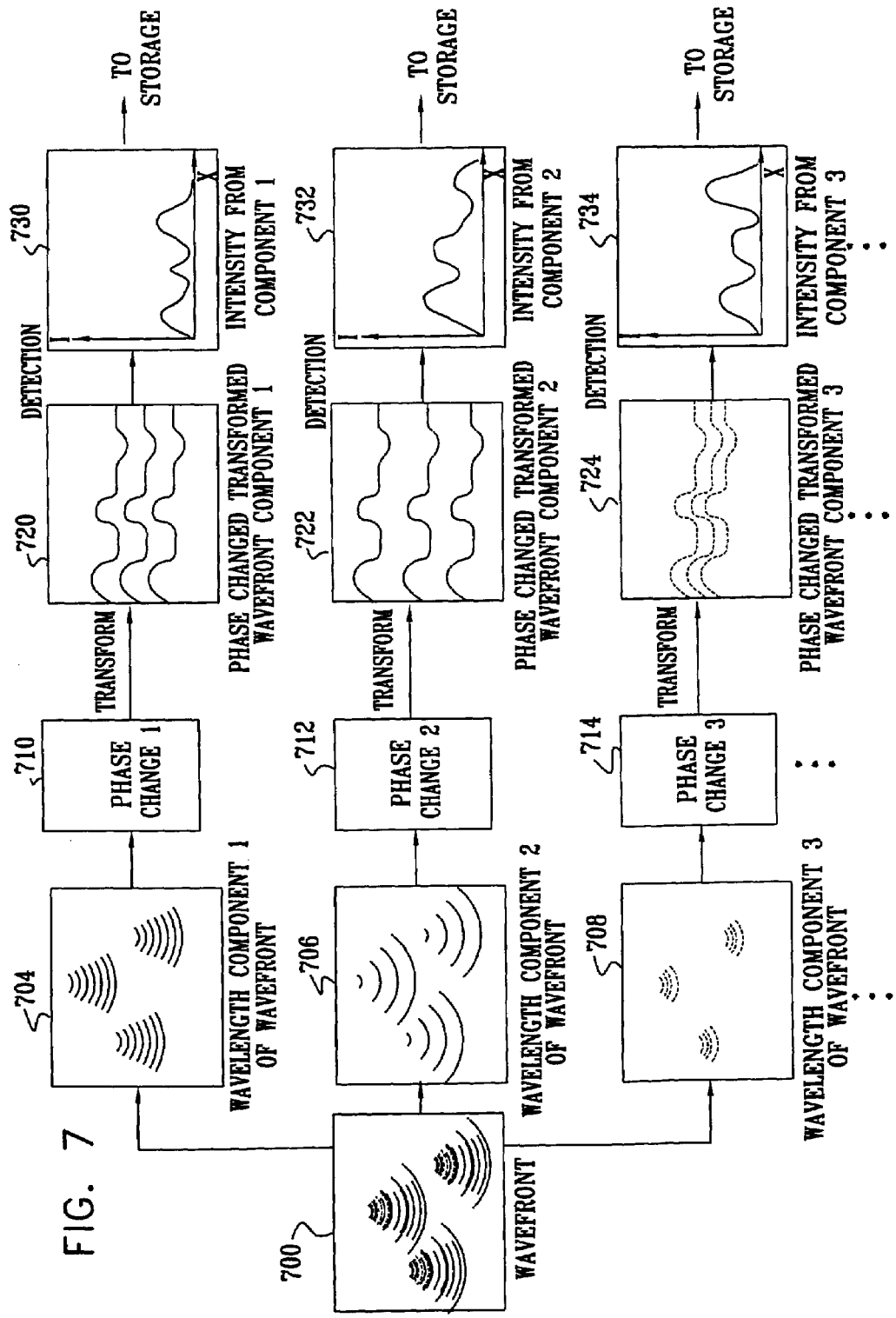
FIG. 7 is a simplified functional block diagram illustration of the functionality of FIG. 1A where phase changes are applied to a plurality of different wavelength components of a wavefront prior to transforming thereof.

Reference is now made to FIG. 7, which is a simplified functional block diagram illustration of the functionality of FIG. 1A where phase changes are applied to a plurality of different wavelength components of a wavefront, prior to transforming thereof As seen in FIG. 7, a wavefront 700 comprises a plurality of different wavelength components 704, 706 and 708. It is appreciated that the wavefront can include any suitable number of wavelength components.

A plurality of phase changes, preferably spatial phase changes, represented by reference numerals 710, 712 and 714, are applied to the respective wavelength components 704, 706 and 708 of the wavefront.

Following application of the spatial phase changes to wavefront components 704, 706 and 708, a transform, preferably a Fourier transform, is applied thereto, thereby providing a plurality of different phase changed transformed wavefront components, represented by reference numerals 720, 722 and 724 respectively.

These phase changed transformed wavefront components 720, 722 and 724 are subsequently detected, as by detector 158 (FIG. 1B), producing spatially varying intensity maps, examples of which are designated by reference numerals 730, 732 and 734. These intensity maps are subsequently stored as by circuitry 160 (FIG. 1B).

In accordance with an embodiment of the present invention, phase changes 710, 712 and 714 are effected by passing the wavefront 700 through an object, at least one of whose thickness and refractive index varies spatially, thereby applying a different spatial phase delay to each of the wavelength components 704, 706 and 708 of the wavefront.

In accordance with another embodiment of the present invention, the phase changes 710, 712 and 714 are effected by reflecting the wavefront 700 from a spatially varying surface, thereby applying a different spatial phase delay to each of the wavelength components 704, 706 and 708 of the wavefront.

In accordance with yet another embodiment of the present invention phase changes 710, 712 and 714 are realized by passing the wavefront 700 through a plurality of objects, each characterized in that at least one of its thickness and refractive index varies spatially. The spatial variance of the thickness or refractive index of these objects is selected in a way such that the phase changes 710, 712 and 714 differ to a selected predetermined extent for at least some of the plurality of different wavelength components 704, 706 and 708.

Alternatively, the spatial variance of the thickness or refractive index of these objects is selected in a way that the phase changes 710, 712 and 714 are identical for at least some of the plurality of different wavelength components 704, 706 and 708.

Figure 8:
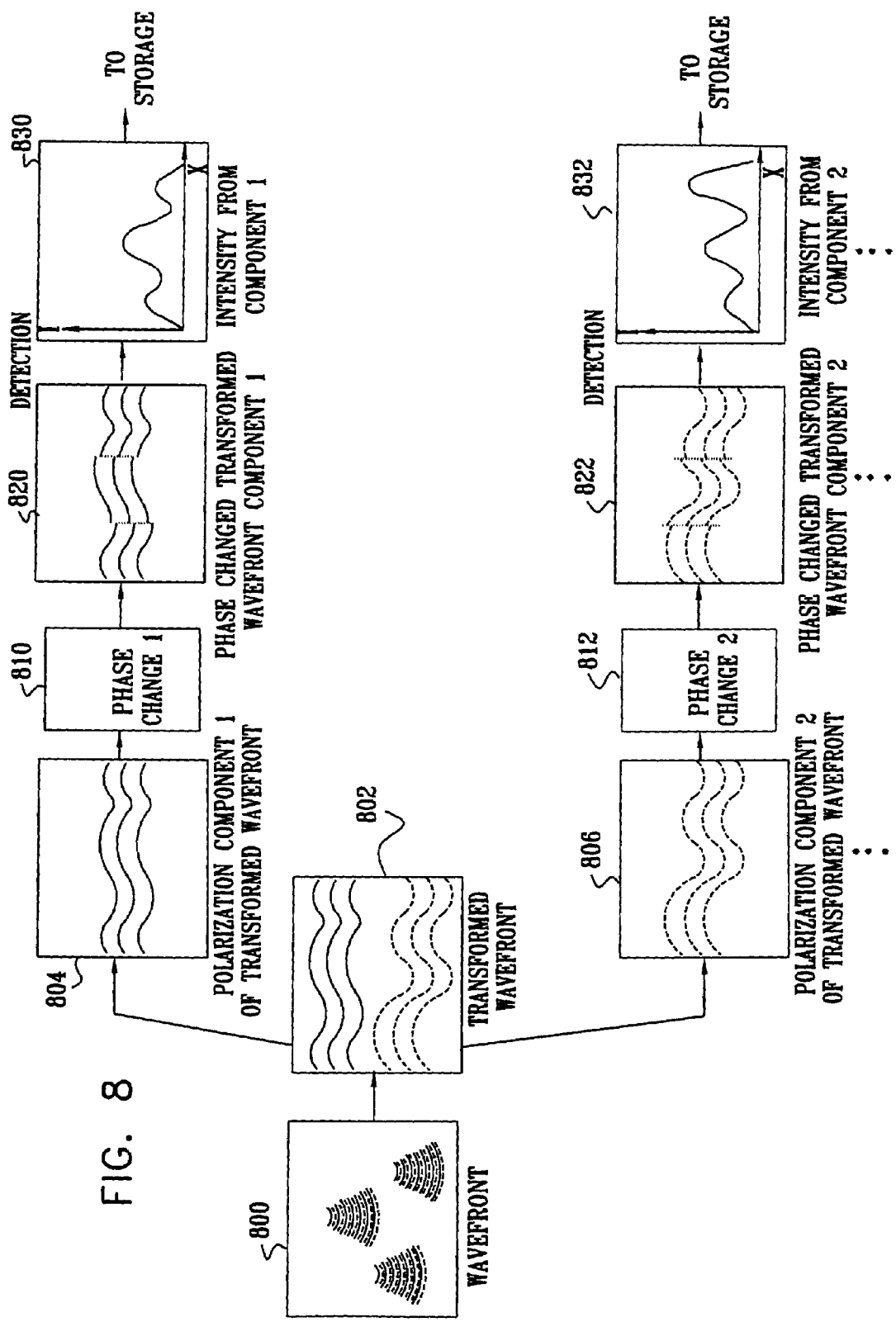
FIG. 8 is a simplified functional block diagram illustration of the functionality of FIG. 1A where phase changes are applied to a plurality of different polarization components of a transformed wavefront.

Reference is now made to FIG. 8, which is a simplified functional block diagram illustration of the functionality of FIG. 1A where phase changes are applied to a plurality of different polarization components of a transformed wavefront. As seen in FIG. 8, a wavefront 800, which comprises a plurality of different polarization components, is preferably transformed to obtain a transformed wavefront 802. The transform is preferably a Fourier transform. Similarly to wavefront 800, the transformed wavefront 802 also includes a plurality of different polarization components, represented by reference numerals 804 and 806. It is appreciated that the polarization components 804 and 806 can be either spatially different or spatially identical, but are each of different polarization. It is further appreciated that both the wavefront 800 and the transformed wavefront 802 preferably each include two polarization components but can include any suitable number of polarization components.

A plurality of phase changes, preferably spatial phase changes, represented by reference numerals 810 and 812, are applied to the respective polarization components 804 and 806 of the transformed wavefront 802, thereby providing a plurality of differently phase changed transformed wavefront components, represented by reference numerals 820 and 822 respectively.

It is appreciated that phase changes 810 and 812 can be different for at least some of the plurality of different polarization components 804 and 806. Alternatively, phase changes 810 and 812 can be identical for at least some of the plurality of different polarization components 804 and 806.

The phase changed transformed wavefront components 820 and 822 are detected, as by detector 158 (FIG. 1B), producing spatially varying intensity maps, examples of which are designated by reference numerals 830 and 832. These intensity maps are subsequently stored as by circuitry 160 (FIG. 1B).

Figure 9:
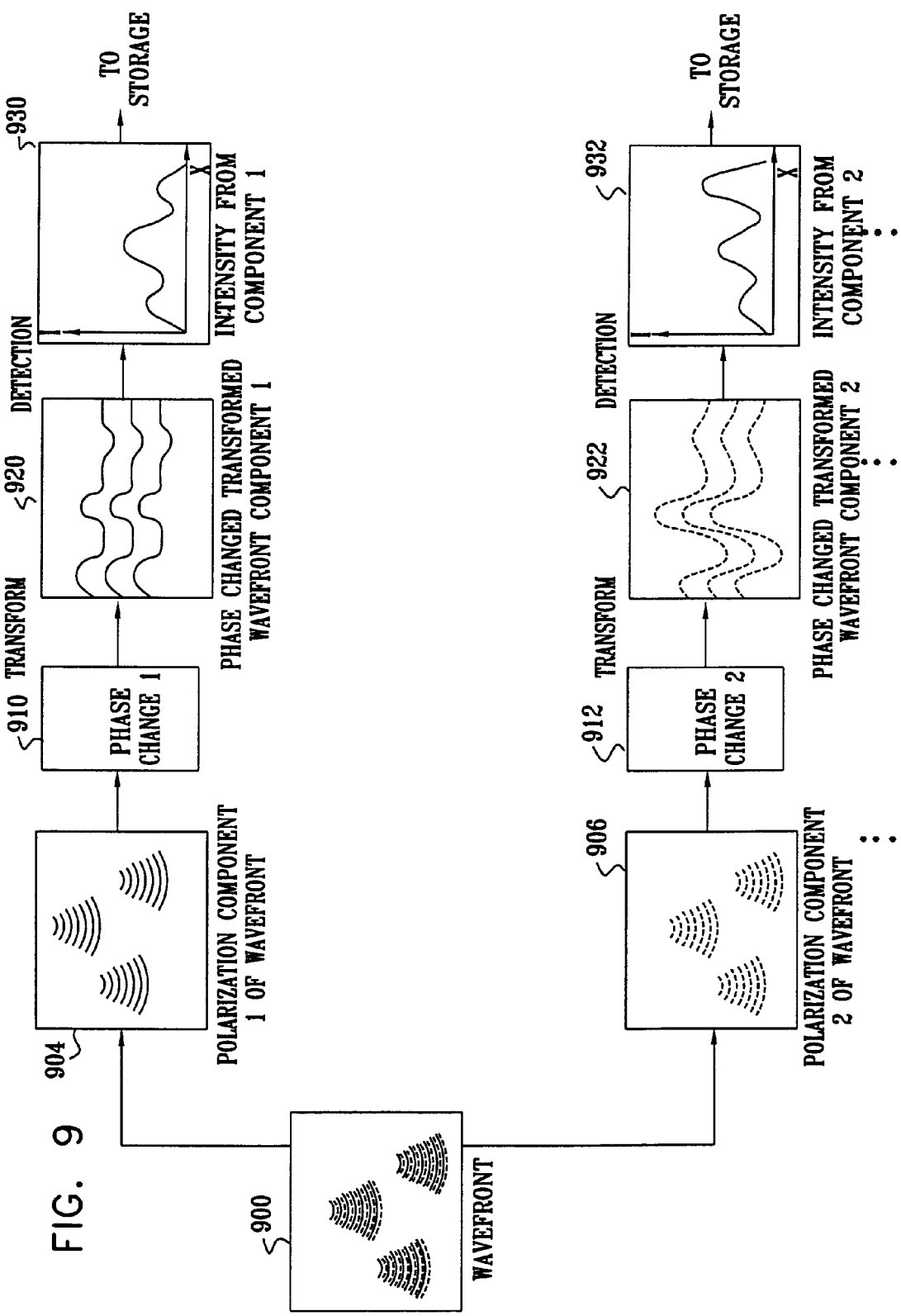
FIG. 9 is a simplified functional block diagram illustration of the functionality of FIG. 1A where phase changes are applied to a plurality of different polarization components of a wavefront prior to transforming thereof.

Reference is now made to FIG. 9, which is a simplified functional block diagram illustration of the functionality of FIG. 1A where phase changes are applied to a plurality of different polarization components of a wavefront prior to transforming thereof. As seen in FIG. 9, a wavefront 900 comprises a plurality of different polarization components 904 and 906. It is appreciated that the wavefront preferably includes two polarization components but can include any suitable number of polarization components.

A plurality of phase changes, preferably spatial phase changes, represented by reference numerals 910 and 912, are applied to the respective polarization components 904 and 906 of the wavefront.

It is appreciated that phase changes 910 and 912 can be different for at least some of the plurality of different polarization components 904 and 906. Alternatively, phase changes 910 and 912 can be set to be identical for at least some of the plurality of different polarization components 904 and 906.

Following application of the spatial phase changes to wavefront components 904 and 906, a transform, preferably a Fourier transform, is applied thereto, thereby providing a plurality of different phase changed transformed wavefront components, designated by reference numerals 920 and 922 respectively.

Phase changed transformed wavefront components 920 and 922 are subsequently detected, as by detector 158 (FIG. 1B), producing spatially varying intensity maps, examples of which are designated by reference numeral 930 and 932. These intensity maps are subsequently stored as by circuitry 160 (FIG. 1B).

Figure 10A:
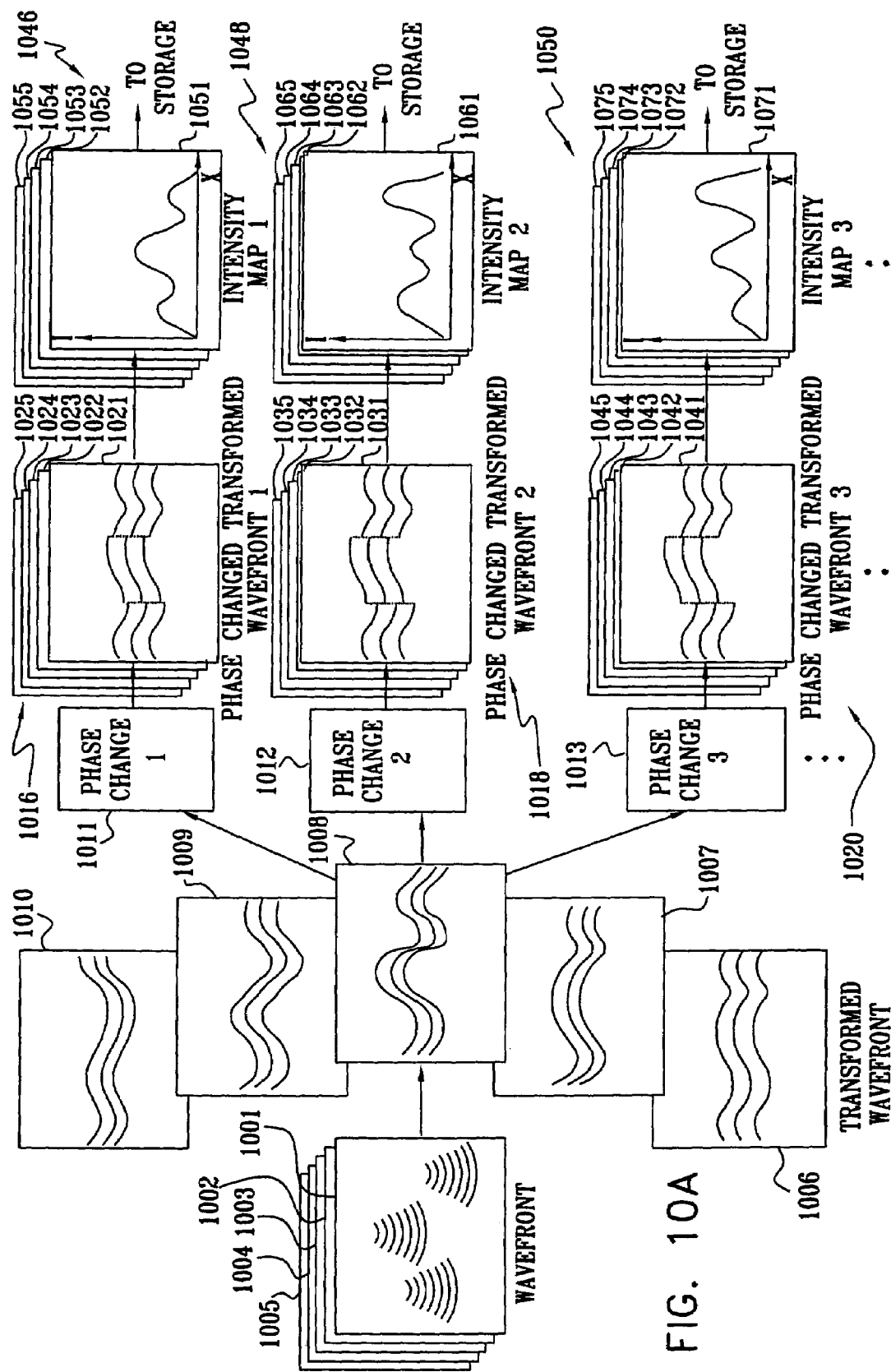
FIG. 10A is a simplified functional block diagram illustration of the functionality of FIG. 1A where a wavefront being analyzed comprises at least one one-dimensional component.

Reference is now made to FIG. 10A, which is a simplified functional block diagram illustration of the functionality of FIG. 1A, where a wavefront being analyzed comprises at least one one-dimensional component. In the embodiment of FIG. 10A, a one-dimensional Fourier transform is applied to the wavefront. Preferably, the transform is performed in a dimension perpendicular to a direction of propagation of the wavefront being analyzed, thereby to obtain at least one one-dimensional component of the transformed wavefront in the dimension perpendicular to the direction of propagation.

A plurality of different phase changes are applied to each of the at least one one-dimensional components, thereby obtaining at least one one-dimensional component of the plurality of phase changed transformed wavefronts.

A plurality of intensity maps are employed to obtain an output indicating amplitude and phase of the at least one one-dimensional component of the wavefront being analyzed.

As seen in FIG. 10A, a plurality of different phase changes are applied to at least one one-dimensional component of a transformed wavefront. In the illustrated embodiment, typically five one-dimensional components of a wavefront are shown and designated by reference numerals 1001, 1002, 1003, 1004 and 1005. The wavefront is transformed, preferably by a Fourier transform. It is thus appreciated that due to transform of the wavefront, the five one-dimensional components 1001, 1002, 1003, 1004 and 1005 are transformed into five corresponding one-dimensional components of the transformed wavefront, respectively designated by reference numerals 1006, 1007, 1008, 1009 and 1010.

Three phase changes, respectively designated 1011, 1012 & 1013 are each applied to the one-dimensional components 1006, 1007, 1008, 1009 and 1010 of transformed wavefront to produce three phase changed transformed wavefronts, designated generally by reference numerals 1016, 1018 and 1020.

In the illustrated embodiment, phase changed transformed wavefront 1016 includes five one-dimensional components, respectively designated by reference numerals 1021, 1022, 1023, 1024 and 1025.

In the illustrated embodiment, phase changed transformed wavefront 1018 includes five one-dimensional components, respectively designated by reference numerals 1031, 1032, 1033, 1034 and 1035.

In the illustrated embodiment, phase changed transformed wavefront 1020 includes five one-dimensional components, respectively designated by reference numerals 1041, 1042, 1043, 1044 and 1045.

The phase changed transformed wavefronts 1016, 1018 and 1020 are detected, as by detector 158 (FIG. 1B), producing three intensity maps, designated generally by reference numerals 1046, 1048 and 1050.

In the illustrated embodiment, intensity map 1046 includes five one-dimensional intensity map components, respectively designated by reference numerals 1051, 1052, 1053, 1054 and 1055.

In the illustrated embodiment, intensity map 1048 includes five one-dimensional intensity map components, respectively designated by reference numerals 1061, 1062, 1063, 1064 and 1065.

In the illustrated embodiment, intensity map 1050 includes five one-dimensional intensity map components, respectively designated by reference numerals 1071, 1072, 1073, 1074 and 1075.

The intensity maps 1046, 1048 and 1050 are stored as by circuitry 160 (FIG. 1B).

In accordance with an embodiment of the present invention, the wavefront being analyzed, illustrated in FIG. 10A by the one-dimensional components 1001, 1002, 1003, 1004 and 1005, may comprise a plurality of different wavelength components and the plurality of different phase changes, 1011, 1012 and 1013, are applied to the plurality of different wavelength components of each of the plurality of one-dimensional components of the wavefront being analyzed. Preferably, obtaining a plurality of intensity maps 1046, 1048 and 1050, includes dividing the plurality of one-dimensional components of the plurality of phase changed transformed wavefronts 1016, 1018 and 1020 into separate wavelength components.

Preferably, dividing the plurality of one-dimensional components of the plurality of phase changed transformed wavefronts into separate wavelength components is achieved by passing the plurality of phase changed transformed wavefronts 1016, 1018 and 1020 through a dispersion element.

Reference is now made to FIG. 10B, which is a simplified partially schematic, partially pictorial illustration of a wavefront analysis system suitable for carrying out the functionality of FIG. 10A in accordance with a preferred embodiment of the present invention.

As seen in FIG. 10B, a wavefront, here designated by reference numeral 1080, and here including five one-dimensional components 1081, 1082, 1083, 1084 and 1085 is focused, as by a cylindrical lens 1086 onto a single axis displaceable phase manipulator 1087, which is preferably located at the focal plane of lens 1086. Lens 1086 preferably produces a one-dimensional Fourier transform of each of the one-dimensional wavefront components 1081, 1082, 1083, 1084 and 1085 along the Y-axis.

As seen in FIG. 10B, the phase manipulator 1087 preferably comprises a multiple local phase delay element, such as a spatially non-uniform transparent object, typically including five different phase delay regions, each arranged to apply a phase delay to one of the one-dimensional components at a given position of the object along an axis, here designated as the X-axis, extending perpendicularly to the direction of propagation of the wavefront along a Z-axis and perpendicular to the axis of the transform produced by lens 1086, here designated as the Y-axis.

A second lens 1088, preferably a cylindrical lens, is arranged so as to image the one-dimensional components 1081, 1082, 1083, 1084 and 1085 onto a detector 1089, such as a CCD detector. Preferably the second lens 1088 is arranged such that the detector 1089 lies in its focal plane. The output of detector 1089 is preferably supplied to data storage and processing circuitry 1090, which preferably carries out functionality "C" described hereinabove with reference to FIG. 1A.

There is provided relative movement between the optical system comprising phase manipulator 1087, lenses 1086 and 1088 and detector 1089 and the one-dimensional wavefront components 1081, 1082, 1083, 1084 and 1085 along the X-axis. This relative movement sequentially matches different phase delay regions with different wavefront components, such that preferably each wavefront component passes through each phase delay region of the phase manipulator 1087.

It is a particular feature of the embodiment of FIGS. 10A and 10B, that each of the one dimensional components of the wavefront is separately processed. Thus, in the context of FIG. 10B, it can be seen that the five one-dimensional wavefront components 1081, 1082, 1083, 1084 and 1085 are each focused by a separate portion of the cylindrical lens 1086, are each imaged by a corresponding separate portion of the cylindrical lens 1088 and each pass through a distinct region of the phase manipulator 1087. The images of each of the five one-dimensional wavefront components 1081, 1082, 1083, 1084 and 1085 at detector 1089 are thus seen to be separate and distinct images, as designated respectively by reference numerals 1091, 1092, 1093, 1094 and 1095. It is appreciated that these images may appear on separate detectors together constituting detector 1089 instead of on a monolithic detector.

In accordance with an embodiment of the present invention, the transform applied to the wavefront includes an additional Fourier transform. This additional Fourier transform may be performed by lens 1086 or by an additional lens and is operative to minimize cross-talk between different one-dimensional components of the wavefront. In such a case, preferably a further transform is applied to the phase changed transformed wavefront. This further transform may be performed by lens 1088 or by an additional lens.

Reference is now made to FIG. 11, which is a simplified functional block diagram illustration of the functionality of FIG. 1A, where an additional transform is applied following the application of spatial phase changes. As seen in FIG. 11, and as explained hereinabove with reference to FIG. 1A, a wavefront 1100 is transformed, preferably by a Fourier transform and a plurality of phase changes are applied to the transformed wavefront, thereby to provide a plurality of differently phased changed transformed wavefronts, represented by reference numerals 1120, 1122, and 1124.

The phase changed transformed wavefronts are subsequently transformed, preferably by a Fourier transform, and then detected, as by detector 158 (FIG. 1B), producing spatially varying intensity maps, examples of which are designated by reference numerals 1130, 1132 and 1134. These intensity maps are subsequently stored as by circuitry 160 (FIG. 1B).

It is appreciated that any suitable number of differently phased changed transformed wavefronts can be obtained, and subsequently transformed to a corresponding plurality of intensity maps to be stored for use in accordance with the present invention.

Figure 12:
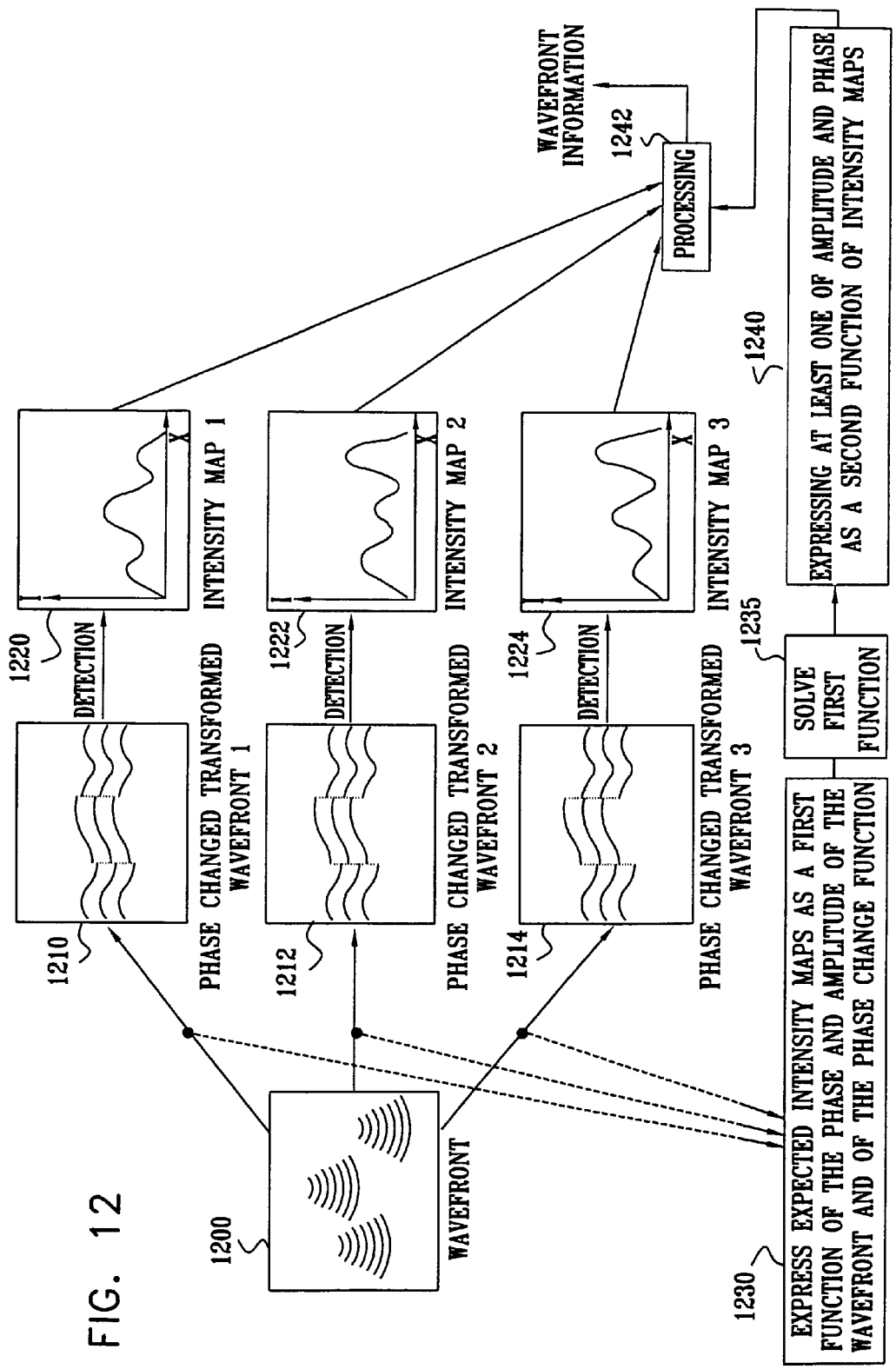
FIG. 12 is a simplified functional block diagram illustration of the functionality of FIG. 1A, wherein intensity maps are employed to provide information about a wavefront being analyzed, such as indications of amplitude and phase of the wavefront.

Reference in now made to FIG. 12, which is a simplified functional block diagram illustration of the functionality of FIG. 1A, wherein intensity maps are employed to provide information about a wavefront being analyzed, such as indications of amplitude and phase of the wavefront. As seen in FIG. 12, and as explained hereinabove with reference to FIG. 1A, a wavefront 1200 is transformed, preferably by a Fourier transform, and phase changed by a phase-change function to obtain several, preferably at least three, differently phase-changed transformed wavefronts, respectively designated by reference numerals 1210, 1212 and 1214. The phase changed transformed wavefronts 1210, 1212 and 1214 are subsequently detected, as by detector 158 (FIG. 1B), producing spatially varying intensity maps, examples of which are designated by reference numerals 1220, 1222 and 1224.

In parallel to producing the plurality of intensity maps, such as intensity maps 1220, 1222 and 1224, the expected intensity maps are expressed as a first function of the amplitude of wavefront 1200, of the phase of wavefront 1200, and of the phase change function characterizing the differently phase changed transformed wavefronts 1210, 1212 and 1214, as indicated at reference numeral 1230.

In accordance with a preferred embodiment of the present invention, at least one of the phase and the amplitude of the wavefront is unknown or both the phase and the amplitude are unknown. The phase-change function is known.

The first function of the phase and amplitude of the wavefront and of the phase change function is subsequently solved as indicated at reference numeral 1235, such as by means of a computer 136 (FIG. 1A), resulting in an expression of at least one and possibly both of the amplitude and phase of wavefront 1200 as a second function of the intensity maps 1220, 1222 and 1224, as indicated at reference numeral 1240.

The second function is then processed together with the intensity maps 1220, 1222 and 1224 as indicated at reference numeral 1242. As part of this processing, detected intensity maps 1220, 1222 and 1224 are substituted into the second function. The processing may be carried out by means of a computer 136 (FIG. 1A) and provides information regarding wavefront 1200, such as indications of at least one and possibly both of the amplitude and the phase of the wavefront.

In accordance with a further embodiment of the present invention, the plurality of intensity maps comprises at least four intensity maps. In such a case, employing the plurality of intensity maps to obtain an indication of at least one of the phase and the amplitude of the wavefront 1200 includes employing a plurality of combinations, each of the combinations being a combination of at least three of the plurality of intensity maps, to provide a plurality of indications of at least one of the phase and the amplitude of wavefront 1200. Preferably, this methodology also includes employing the plurality of indications of at least one of the phase and the amplitude of the wavefront 1200 to provide an enhanced indication at least one of the phase and the amplitude of the wavefront 1200.

In accordance with a preferred embodiment of the present invention, at least some of the plurality of indications of the amplitude and phase are at least second order indications of the amplitude and phase of the wavefront 1200.

In accordance with another embodiment of the present invention, the first function may be solved as a function of some unknowns to obtain the second function by expressing, as indicated by reference numeral 1240, some unknowns, such as at least one of the amplitude and phase of wavefront 1200, as a second function of the intensity maps.

Accordingly, solving the first function may include:
defining a complex function of the amplitude of wavefront 1200, of the phase of wavefront 1200, and of the phase change function characterizing the differently phase changed transformed wavefronts 1210, 1212 and 1214. This complex function is characterized in that intensity at each location in the plurality of intensity maps is a function predominantly of a value of the complex function at that location and of the amplitude and the phase of wavefront 1200 at the same location;
expressing the complex function as a third function of the plurality of intensity maps 1220, 1222 and 1224; and
obtaining values for the unknowns, such as at least one of phase and amplitude of wavefront 1200, by employing the complex function expressed as a function of the plurality of intensity maps.

In accordance with this embodiment, preferably the complex function is a convolution of another complex function, which has an amplitude and phase identical to the amplitude and phase of wavefront 1200, and of a Fourier transform of the phase change function characterizing the differently phase changed transformed wavefronts 1210, 1212 and 1214.

Figure 13:
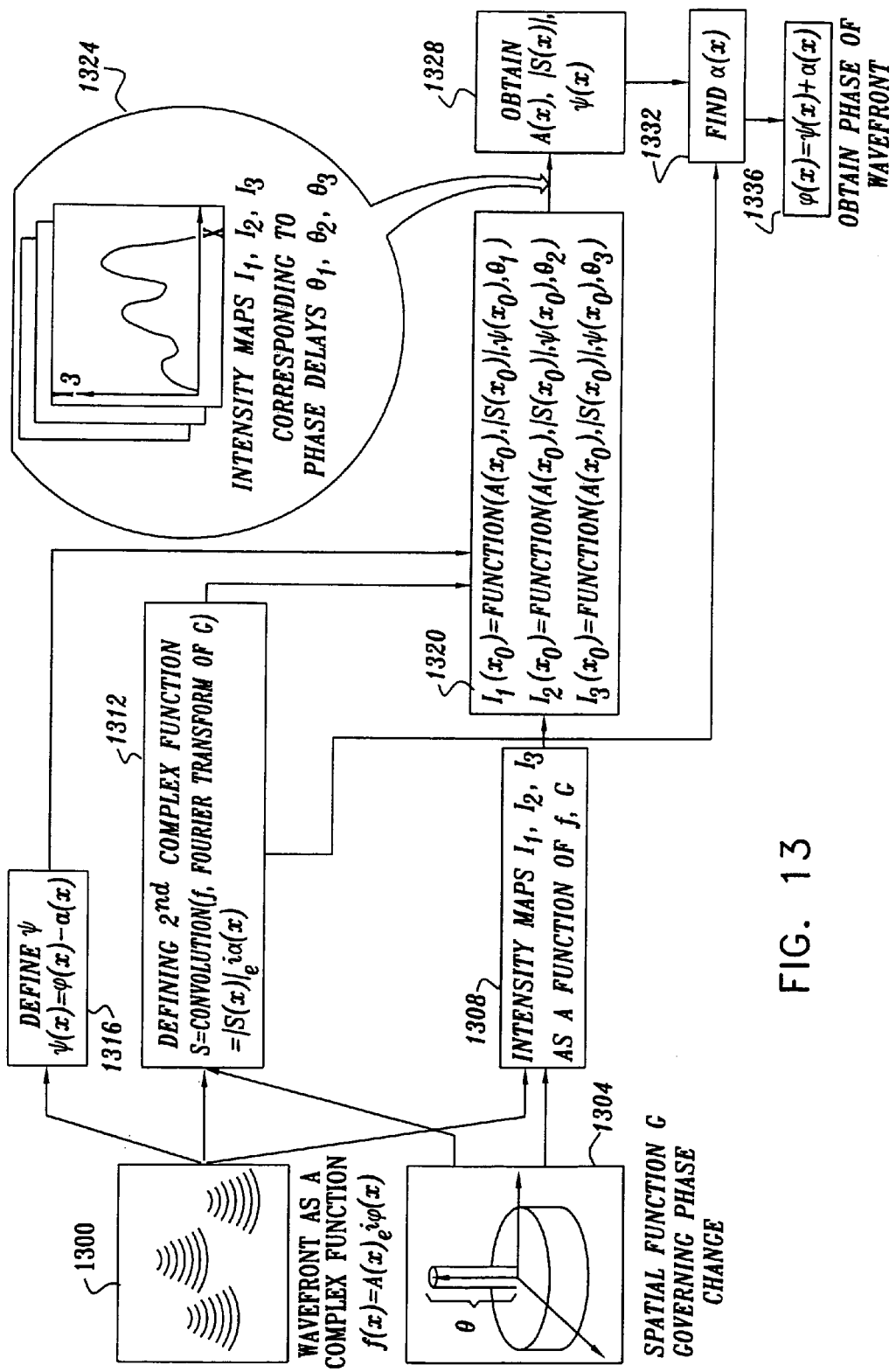
FIG. 13 is a simplified functional block diagram illustration of part of the functionality of FIG. 1A, wherein the transform applied to the wavefront being analyzed is a Fourier transform, wherein at least three different spatial phase changes are applied to a transformed wavefront, and wherein at least three intensity maps are employed to obtain indications of at least the phase of a wavefront.

Reference in now made to FIG. 13, which is a simplified functional block diagram illustration of part of the functionality of FIG. 1A, wherein the transform applied to the wavefront being analyzed is a Fourier transform, wherein at least three different spatial phase changes are applied to the thus transformed wavefront, and wherein at least three intensity maps are employed to obtain indications of at least one of the phase and the amplitude of the wavefront.

As explained hereinabove with reference to FIG. 1A, a wavefront 100 (FIG. 1A) being analyzed, is transformed and phase changed by at least three different spatial phase changes, all governed by a spatial function, to obtain at least three differently phase-changed transformed wavefronts, represented by reference numerals 120, 122 and 124 (FIG. 1A) which are subsequently detected, as by detector 158 (FIG. 1B), producing spatially varying intensity maps, examples of which are designated by reference numerals 130, 132 and 134 (FIG. 1A). As seen in FIG. 13, and designated as sub-functionality "C" hereinabove with reference in FIG. 1A, the intensity maps are employed to obtain an output indication of at least one and possibly both of the phase and the amplitude of the wavefront being analyzed.

Turning to FIG. 13, it is seen that the wavefront being analyzed is expressed as a first complex function $f(x)=A(x)e^{i\phi(x)}$, where 'x' is a general indication of a spatial location. The complex function has an amplitude distribution $A(x)$ and a phase distribution $\phi(x)$ identical to the amplitude and phase of the wavefront being analyzed. The first complex function $f(x)=A(x)e^{i\phi(x)}$ is indicated by reference numeral 1300.

As noted hereinabove with reference to FIG. 1A, each of the plurality of different spatial phase changes is applied to the transformed wavefront preferably by applying a spatially uniform spatial phase delay having a known value to a given spatial region of the transformed wavefront. As seen in FIG. 13, the spatial function governing these different phase changes is designated by 'G' and an example of which, for a phase delay value of θ, is designated by reference numeral 1304.

Function 'G' is a spatial function of the phase change applied in each spatial location of the transformed wavefront. In the specific example designated by reference numeral 1304, the spatially uniform spatial phase delay, having a value of θ, is applied to a spatially central region of the transformed wavefront, as indicated by the central part of the function having a value of θ, which is greater than the value of the function elsewhere.

A plurality of expected intensity maps, indicated by spatial functions $I_1(x)$, $I_2(x)$ and $I_3(x)$, are each expressed as a function of the first complex function $f(x)$ and of the spatial function G, as indicated by reference numeral 1308.

Subsequently, a second complex function $S(x)$, which has an absolute value $|S(x)|$ and a phase $\alpha(x)$, is defined as a convolution of the first complex function $f(x)$ and of a Fourier transform of the spatial function 'G'. This second complex function, designated by reference numeral 1312, is indicated by the equation $S(x)=f(x)*\Im(G)=|S(x)|e^{i\alpha(x)}$, where the symbol '*' indicates convolution and $\Im(G)$ is the Fourier transform of the function 'G'.

The difference between $\phi(x)$, the phase of the wavefront, and $\alpha(x)$, the phase of the second complex function, is indicated by $\psi(x)$, as designated by reference numeral 1316.

The expression of each of the expected intensity maps as a function of $f(x)$ and G, as indicated by reference numeral 1308, the definition of the absolute value and the phase of $S(x)$, as indicated by reference numeral 1312 and the definition of $\psi(x)$, as indicated by reference numeral 1316, enables expression of each of the expected intensity maps as a third function of the amplitude of the wavefront $A(x)$, the absolute value of the second complex function $|S(x)|$, the difference between the phase of the wavefront and the phase of the second complex function $\psi(x)$, and the known phase delay produced by one of the at least three different phase changes which each correspond to one of the at least three intensity maps.

This third function is designated by reference numeral 1320 and includes three functions, each preferably having the general form $$I_n(x) = |A(x) + (e^{i\theta_n} - 1)|S(x)|e^{-i\psi(x)}|^2$$

where $I_n(x)$ are the expected intensity maps and n=1,2 or 3. In the three functions, $\theta_1$, $\theta_2$ and $\theta_3$ are the known values of the uniform spatial phase delays, each applied to a spatial region of the transformed wavefront, thus effecting the plurality of different spatial phase changes which produce the intensity maps $I_1(x)$, $I_2(x)$ and $I_3(x)$, respectively.

It is appreciated that preferably the third function at any given spatial location $x_0$ is a function of A, $\psi$ and |S| only at the same spatial location $x_0$.

The intensity maps are designated by reference numeral 1324.

The third function is solved for each of the specific spatial locations $x_0$, by solving at least three equations, relating to at least three intensity values $I_1(x_0)$, $I_2(x_0)$ and $I_3(x_0)$ at at least three different phase delays $\theta_1$, $\theta_2$ and $\theta_3$, thereby to obtain at least part of three unknowns $A(x_0)$, $|S(x_0)|$ and $\psi(x_0)$. This process is typically repeated for all spatial locations and results in obtaining the amplitude of the wavefront $A(x)$, the absolute value of the second complex function $|S(x)|$ and the difference between the phase of the wavefront and the phase of the second complex function $\psi(x)$, as indicated by reference numeral 1328.

Thereafter, once $A(x)$, $|S(x)|$ and $\psi(x)$ are known, the equation defining the second complex function, represented by reference numeral 1312, is typically solved globally for a substantial number of spatial locations 'x' to obtain $a(x)$, the phase of the second complex function, as designated by reference numeral 1332.

Finally, the phase $\phi(x)$ of the wavefront being analyzed is obtained by adding the phase $\alpha(x)$ of the second complex function to the difference $\psi(x)$ between the phase of the wavefront and the phase of the second complex function, as indicated by reference numeral 1336.

In accordance with an embodiment of the present invention, the absolute value |S| of the second complex function is obtained preferably for every specific spatial location $x_0$ by approximating the absolute value to a polynomial of a given degree in the spatial location x.

In accordance with another preferred embodiment of the present invention, the phase $\alpha(x)$ of the second complex function is obtained by expressing the second complex function $S(x)$ as an eigen-value problem, such as $S=S \cdot M$ where M is a matrix, and the complex function is an eigen-vector of the matrix obtained by an iterative process. An example of such an iterative process is $S_0=|S|$, $S_{n+1}=S_n M / \|S_n M\|$, where n is the iterative step number.

In accordance with yet another preferred embodiment of the present invention, the phase $\alpha(x)$ of the second complex function is obtained by approximating the Fourier transform of the spatial function 'G', governing the spatial phase change, to a polynomial in the location x, by approximating the second complex function $S(x)$ to a polynomial in the location x, and by solving, according to these approximations, the equation defining the second complex function:

$$S(x) = \left( \frac{A(x) e^{i\psi(x)}}{|S(x)|} S(x) \right) * \mathfrak{J}[G],$$

where the function $$\frac{A(x) e^{i\psi(x)}}{|S(x)|}$$

is known.

In accordance with still another preferred embodiment of the present invention, at any location x the amplitude $A(x)$ of the wavefront being analyzed, the absolute value $|S(x)|$ of the second complex function, and the difference $\psi(x)$ between the phase of the second complex function and the phase of the wavefront are obtained by a best-fit method, such as a least-square method, preferably a linear least-square method, from the values of the intensity maps at this location $I_n(x)$, where $n=1,2,\ldots,N$ and N is the number of intensity maps. The accuracy of this process increases as the number N of the plurality of intensity maps increases.

In accordance with one preferred embodiment of the present invention, the plurality of different phase changes comprises at least four different phase changes, the plurality of intensity maps comprises at least four intensity maps, and the function designated by reference numeral 1320 can express each of the expected intensity maps as a third function of:

the amplitude of the wavefront $A(x)$, the absolute value of the second complex function $|S(x)|$;

the difference between the phase of the wavefront and the phase of the second complex function $\psi(x)$;

the known phase delay produced by one of the at least four different phase changes each of which corresponds to one of the at least four intensity maps; and at least one additional unknown relating to the wavefront analysis, where the number of the at least one additional unknown is no greater than the number by which the plurality intensity maps exceeds three.

The third function 1320, is then solved by solving at least four equations, resulting from at least four intensity values at at least four different phase delays, thereby to obtain the amplitude of the wavefront being analyzed, the absolute value of the second complex function, the difference between the phase of the wavefront and the phase of the second complex function and the at least one additional unknown.

In accordance with another preferred embodiment of the present invention, the values of the uniform spatial phase delays $\theta_1, \theta_2, \ldots, \theta_N$ applied to a spatial region of the transformed wavefront, thus effecting the plurality of different spatial phase changes, producing the intensity maps $I_1(x), I_2(x), \ldots, I_N(x)$ respectively, are chosen as to maximize contrast in the intensity maps and to minimize effects of noise on the phase of the wavefront being analyzed.

In accordance with one more preferred embodiment of the present invention, the function designated by reference numeral 1320, expressing each of the expected intensity maps as a third function of the amplitude of the wavefront $A(x)$, the absolute value of the second complex function $|S(x)|$, the difference between the phase of the wavefront and the phase of the second complex function $\psi(x)$, and the known phase delay $\theta_i$ produced by one of the at least three different phase changes which each correspond to one of the at least three intensity maps, comprises several functionalities:

defining fourth, fifth and sixth complex functions, designated as $\beta_0(x)$, $\beta_s(x)$ and $\beta_c(x)$ respectively, none of which is a function of any of the plurality of intensity maps or of the spatial function 'G' governing the phase change. Each of the fourth, fifth and sixth complex functions is preferably a function of the amplitude of the wavefront $A(x)$, the absolute value of the second complex function $|S(x)|$, the difference between the phase of the wavefront and the phase of the second complex function $\psi(x)$; and expressing each of the plurality of intensity maps $I_n(x)$ as $I_n(x)=\beta_0(x)+\beta_C(x)\cos(\theta_n)+\beta_S(x)\sin(\theta_n)$, where $\theta_n$ is the value of the phase delay corresponding to intensity map $I_n(x)$. Each intensity map $I_n(x)$, where $n=1, 2, \ldots N$, preferably expressed as $$I_n(x) = |A(x) + (e^{i\theta_n} - 1)|S(x)|e^{-i\psi(x)}|^2, \quad 5$$

can be subsequently expressed as $I_n(x)=\beta_0(x)+\beta_C(x)\cos(\theta_n)+\beta_S(x)\sin(\theta_n)$, where $$\begin{cases} \beta_0(x) = A(x)^2 + 2|S(x)|^2 - 2A(x)|S(x)|\cos(\psi) \\ \beta_C(x) = 2A(x)|S(x)|\cos(\psi) - 2|S(x)|^2 \\ \beta_S(x) = 2A(x)|S(x)|\sin(\psi) \end{cases}$$

Preferably the foregoing methodology also includes solving the third function 1320 by using a linear least-square method to compute from the different intensities $I(\theta_1), \ldots, I(\theta_N)$, the values of $\beta_0$, $\beta_c$ and $\beta_s$ best fitting to $I(\theta_n)=\beta_0+\beta_c\cos\theta_n+\beta_s\sin\theta_n$. Subsequently the amplitude $A(x)$ is found by $$A(x) = \sqrt{\beta_0(x) + \beta_c(x)},$$

the absolute value $|S(x)|$ of the second complex function is found by solving the second degree equation $$|S(x)|^4 - \beta_0(x)|S(x)|^2 + \frac{\beta_C(x)^2 + \beta_S(x)^2}{4} = 0$$

for $|S(x)|^2$, and $\psi(x)$ is found by $\psi(x)=\arg(\beta_C(x)+2|S(x)|^2+i\beta_S(x))$ In accordance with yet another preferred embodiment of the present invention, solving of the third function, designated by reference numeral 1320, to obtain, as designated by reference numeral 1328, the amplitude of the wavefront $A(x)$, the absolute value of the second complex function $|S(x)|$ and the difference between the phase of the wavefront and the phase of the second complex function $\psi(x)$, includes several functionalities:

obtaining two solutions for the absolute value $|S(x)|$ of the second complex function, these two solutions, being designated by $|S_h(x)|$ and $|S_l(x)|$, namely a higher value solution and a lower value solution respectively; and combining the two solutions into an enhanced absolute value solution $|S(x)|$ for the absolute value of the second complex function, by choosing at each spatial location '$x_0$' either the higher value solution $|S_h(x_0)|$ or the lower value solution $|S_l(x_0)|$ such that the enhanced absolute value solution satisfies the second complex function, designated by reference numeral 1312.

Preferably the methodology also includes:

obtaining two solutions for each of the amplitude $A(x)$ of the wavefront being analyzed and the difference $\psi(x)$ between the phase of the wavefront and the phase of the second complex function, these two solutions being higher value solutions $A_h(x)$ and $\psi_h(x)$ and lower value solutions $A_l(x)$ and $\psi_l(x)$; and combining the two solutions $A_h(x)$ and $A_l(x)$ for the amplitude into an enhanced amplitude solution $A(x)$ by choosing at each spatial location '$x_0$' either the higher value solution $A_h(x_0)$ or the lower value solution $A_l(x_0)$ in a way that at each spatial location '$x_0$' if $|S_h(x_0)|$ is chosen for the absolute value solution, then $A_h(x_0)$ is chosen for the amplitude solution and at each location '$x_1$' if $|S_l(x_1)|$ is chosen for the absolute value solution, then $A_l(x_1)$ is chosen for the amplitude solution; and combining the two solutions $\psi_h(X)$ and $\psi_l(x)$ of the difference between the phase of the wavefront and the phase of the second complex function into an enhanced difference solution $\psi(x)$, by choosing at each spatial location '$x_0$' either the higher value solution $\psi_h(x_0)$ or the lower value solution $\psi_l(x_0)$ in a way that at each spatial location '$x_0$' if $|S_h(x_0)|$ is chosen for the absolute value solution, then $\psi_h(x_0)$ is chosen for the difference solution and at each location '$x_1$' if $|S_l(x_1)|$ is chosen for the absolute value solution, then $\psi_l(x_1)$ is chosen for the difference solution.

Additionally, in accordance with an embodiment of the present invention, the plurality of different phase changes applied to the transformed wavefront, thereby to obtain a plurality of differently phase changed transformed wavefronts, also include amplitude changes, resulting in a plurality of differently phase and amplitude changed transformed wavefronts. These amplitude changes are preferably known amplitude attenuations applied to the same spatial region of the transformed wavefront to which the uniform phase delays $\theta_1, \theta_2, \ldots, \theta_N$, are applied, the spatial region being defined by the spatial function 'G'.

The amplitude attenuations are designated by $\sigma_1, \sigma_2, \ldots, \sigma_N$, where the n-th change, where $n=1,2, \ldots N$, applied to the transformed wavefront includes a phase change $\theta_n$ and an amplitude attenuation $\sigma_n$. It is appreciated that some of the phase changes may be equal to zero, indicating no phase-change and that some of the amplitude attenuations may be equal to unity, indicating no amplitude attenuation.

In this embodiment, the function designated by reference numeral 1320, expressing each of the expected intensity maps $I_n(x)$ as a third function of the amplitude of the wavefront $A(x)$, the absolute value of the second complex function $|S(x)|$, the difference between the phase of the wavefront and the phase of the second complex function $\psi(x)$, and the phase delay $\theta_n$, also expresses each of the expected intensity maps also as a function of the amplitude attenuation $\sigma_n$ and comprises several functionalities:

defining fourth, fifth, sixth and seventh complex functions, designated by $\beta_0(x)$, $\beta_1(x)$, $\beta_2(x)$ and $\beta_3(x)$ respectively, none of which is a function of any of the plurality of intensity maps or of the spatial function 'G' governing the phase and amplitude changes. Each of the fourth, fifth, sixth and seventh complex functions is preferably a function of the amplitude of the wavefront $A(x)$, the absolute value of the second complex function $|S(x)|$, the difference between the phase of the wavefront and the phase of the second complex function $\psi(x)$;

defining an eighth function, designated $\mu$, as a combination of the phase delay and of the amplitude attenuation, where for the n-th change applied to the transformed wavefront, including a phase change $\theta_n$ and an amplitude attenuation $\sigma_n$, this eighth function is designated by $\mu_n$. Preferably the combination $\mu_n$ is defined by $\mu_n = \sigma_n e^{i\theta_n} - 1$; and expressing each of the plurality of intensity maps $I_n(x)$ as $$I_n(x) = \beta_0(x) + \beta_1(x)|\mu_n|^2 + \beta_2(x)\mu_n +$$
$$\beta_3(x)\bar{\mu}_n, \text{ where } \beta_0(x) = A^2(x); \beta_1(x) = |S(x)|^2; \beta_2(x) =$$
$$A(x)|S(x)|e^{-i\psi(x)} \text{ and } \beta_3(x) = A(x)|S(x)|e^{i\psi(x)}.$$

Preferably the foregoing methodology also includes solving the third function 1320 by computing from the different intensities $I_n(x)$, the values of $\beta_0(x)$, $\beta_1(x)$, $\beta_2(x)$ and $\beta_3(x)$ best fitting to the equation $I_n(x)=\beta_0(x)+\beta_1(x)|\mu_n|^2+\beta_2(x)\mu_n+\beta_3(x)\bar{\mu}_n$. Subsequently the amplitude $A(x)$ is found by $$A(x) = \sqrt{\beta_0(x)},$$

the absolute value $|S(x)|$ of the second complex function is found by $$|S(x)| = \sqrt{\beta_1(x)}$$

and $\psi(x)$ is found by solving $e^{i\psi(x)}=\text{angle}(\beta_3(x))$.

It is appreciated that the amplitude attenuations $\sigma_1$, $\sigma_2, \ldots, \sigma_N$, may be unknown. In such a case, additional intensity maps are obtained, where the number of the unknowns is no greater than the number by which the plurality of intensity maps exceeds three. The unknowns are obtained in a manner similar to that described hereinabove, where there exists at least one unknown relating to the wavefront analysis.

Figure 14:
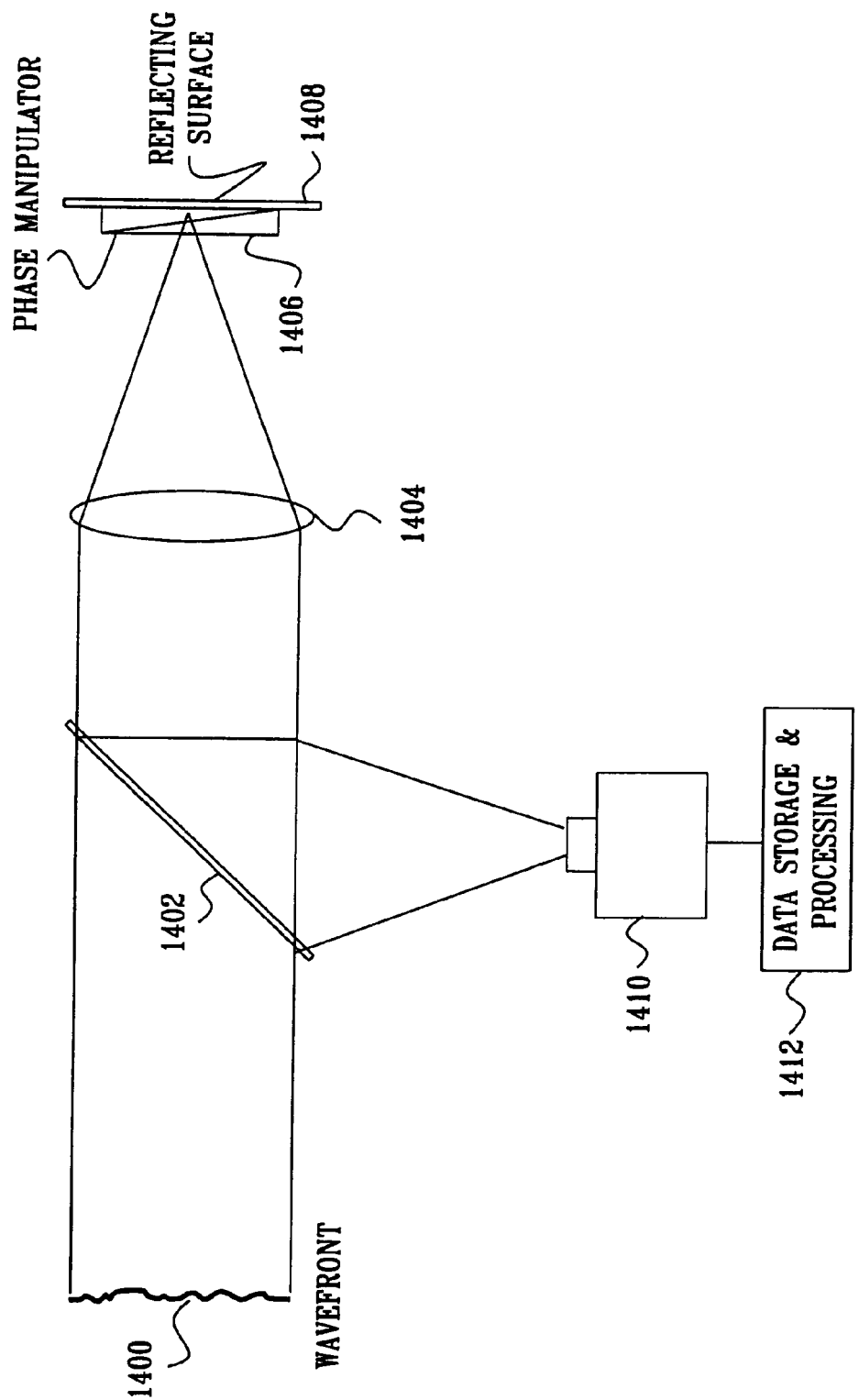
FIG. 14 is a simplified partially schematic, partially pictorial illustration of part of one preferred embodiment of a wavefront analysis system of the type shown in FIG. 1B.

Reference is now made to FIG. 14, which is a simplified partially schematic, partially pictorial illustration of part of one preferred embodiment of a wavefront analysis system of the type shown in FIG. 1B. As seen in FIG. 14, a wavefront, here designated by reference numeral 1400 is partially transmitted through a beam splitter 1402 and subsequently focused, as by a lens 1404 onto a phase manipulator 1406, which is preferably located at the focal plane of lens 1404. The phase manipulator 1406 may be, for example, a spatial light modulator or a series of different transparent, spatially non-uniform objects.

A reflecting surface 1408 is arranged so as to reflect wavefront 1400 after it passes through the phase manipulator 1406. The reflected wavefront is imaged by lens 1404 onto a detector 1410, such as a CCD detector via beam splitter 1402. Preferably the beam splitter 1402 and the detector 1410 are arranged such that the detector 1410 lies in the focal plane of lens 1404. The output of detector 1410 is preferably supplied to data storage and processing circuitry 1412, which preferably carries out functionality "C" described hereinabove with reference to FIG. 1A.

It is appreciated that adding the reflecting surface 1408 to an imaging system, doubles the phase delay generated by phase manipulator 1406, enables imaging with a single lens 1404, and generally enables realization of a more compact system.

Figure 15:
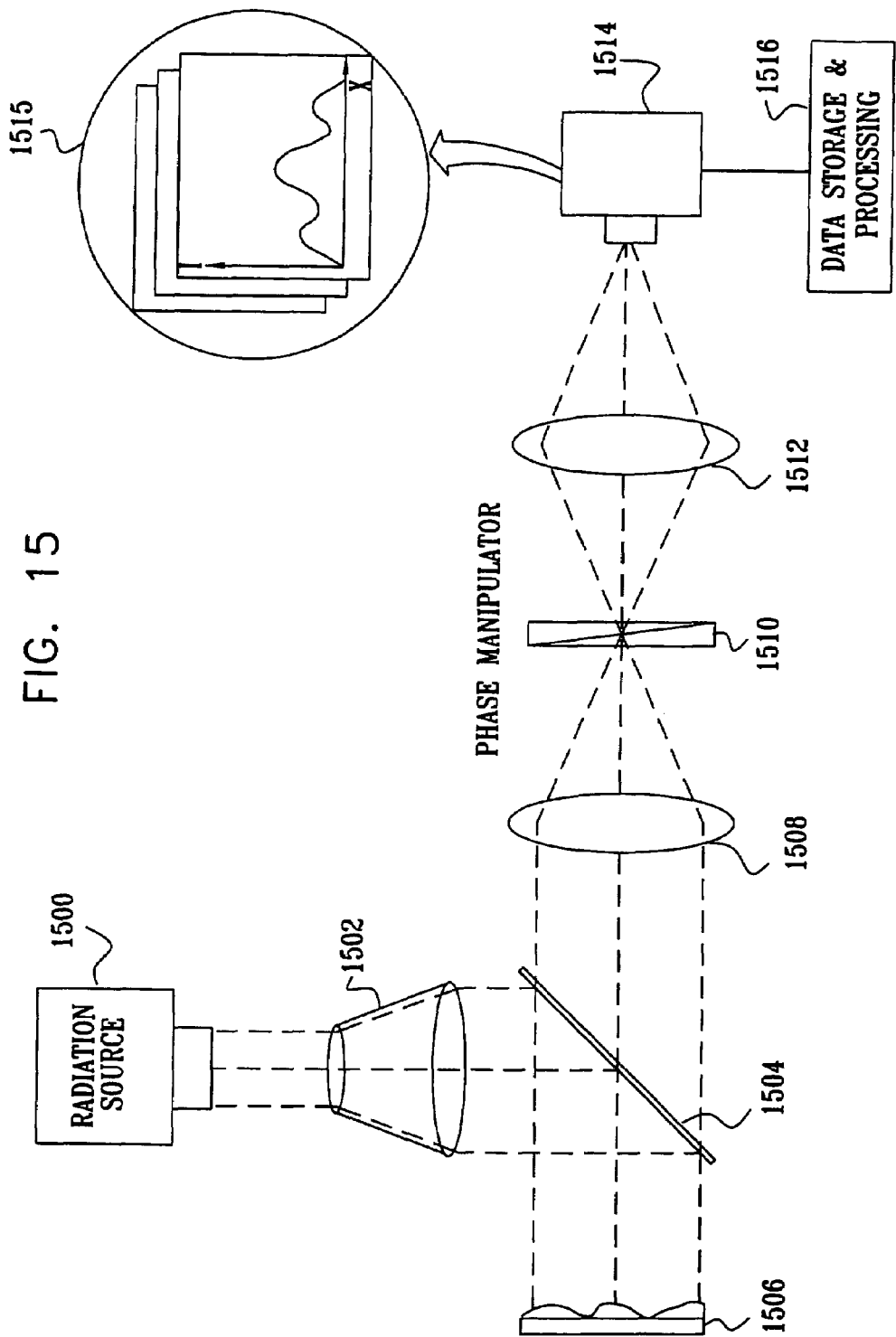
FIG. 15 is a simplified partially schematic, partially pictorial illustration of a system for surface mapping employing the functionality and structure of FIGS. 1A and 1B.

Reference is now made to FIG. 15, which is a simplified partially schematic, partially pictorial illustration of a system for surface mapping employing the functionality and structure of FIGS. 1A and 1B. As seen in FIG. 15, a beam of radiation, such as light or acoustic energy, is supplied from a radiation source 1500, optionally via a beam expander 1502, onto a beam splitter 1504, which reflects at least part of the radiation onto a surface 1506 to be inspected. The radiation reflected from the inspected surface 1506, is a surface mapping wavefront, which has an amplitude and a phase, and which contains information about the surface 1506. At least part of the radiation incident on surface 1506 is reflected from the surface 1506 and transmitted via the beam splitter 1504 and focused via a focusing lens 1508 onto a phase manipulator 1510, which is preferably located at the image plane of radiation source 1500.

The phase manipulator 1510 may be, for example, a spatial light modulator or a series of different transparent, spatially non-uniform objects. It is appreciated that phase manipulator 1510 can be configured such that a substantial part of the radiation focused thereonto is reflected therefrom. Alternatively the phase manipulator 1510 can be configured such that a substantial part of the radiation focused thereonto is transmitted therethrough.

A second lens 1512 is arranged so as to image surface 1506 onto a detector 1514, such as a CCD detector. Preferably the second lens 1512 is arranged such that the detector 1514 lies in its focal plane. The output of detector 1514, an example of which is a set of intensity maps designated by reference numeral 1515, is preferably supplied to data storage and processing circuitry 1516, which preferably carries out functionality "C" described hereinabove with reference to FIG. 1A, providing an output indicating at least one and possibly both of the phase and the amplitude of the surface mapping wavefront. This output is preferably further processed to obtain information about the surface 1506, such as geometrical variations and reflectivity of the surface.

In accordance with a preferred embodiment of the present invention, the beam of radiation supplied from radiation source 1500 has a narrow wavelength band about a given central wavelength, causing the phase of the radiation reflected from surface 1506 to be proportional to geometrical variations in the surface 1506, the proportion being an inverse linear function of the central wavelength of the radiation.

In accordance with another preferred embodiment of the present invention, the beam of radiation supplied from radiation source 1500 has at least two narrow wavelength bands, each centered about a different wavelength, designated $\lambda_1, \ldots, \lambda_n$. In such a case, the radiation reflected from the surface 1506 has at least two wavelength components, each centered around a wavelength $\lambda_1, \ldots, \lambda_n$ and at least two indications of the phase of the surface mapping wavefront are obtained. Each such indication corresponds to a different wavelength component of the reflected radiation. These at least two indications may be subsequently combined to enable enhanced mapping of the surface 1506, by avoiding ambiguity in the mapping, known as $2\pi$ ambiguity, when the value of the mapping at a given spatial location in the surface exceeds the value of the mapping at a different spatial location in the surface by the largest of the different wavelengths $\lambda_1, \ldots, \lambda_n$. A proper choice, of the wavelengths $\lambda_1, \ldots, \lambda_n$, may lead to elimination of this ambiguity when the difference in values of the mapping at different locations is smaller than the multiplication product of all the wavelengths.

In accordance with still another preferred embodiment of the present invention, the phase manipulator 1510 applies a plurality of different spatial phase changes to the radiation wavefront reflected from surface 1506 and Fourier transformed by lens 1508. Application of the plurality of different spatial phase changes provides a plurality of differently phase changed transformed wavefronts which may be subsequently detected by detector 1514.

In accordance with yet another preferred embodiment of the present invention, at least three different spatial phase changes are applied by phase manipulator 1510, resulting in at least three different intensity maps 1515. The at least three intensity maps are employed by the data storage and processing circuitry 1516 to obtain an output indicating at least the phase of the surface mapping wavefront. In such a case, the data storage and processing circuitry 1516, carries out functionality "C" described hereinabove with reference to FIG. 1A, preferably in a manner described hereinabove with reference to FIG. 13, where the wavefront being analyzed (FIG. 13) is the surface mapping wavefront.

Additionally, in accordance with a preferred embodiment of the present invention, the beam of radiation supplied from radiation source 1500 comprises a plurality of different wavelength components, thereby providing a plurality of wavelength components in the surface mapping wavefront and subsequently in the transformed wavefront impinging on phase manipulator 1510. In this case the phase manipulator may be an object, at least one of whose thickness, refractive index and surface geometry varies spatially. This spatial variance of the phase manipulator generates a different spatial phase change for each of the wavelength components, thereby providing a plurality of differently phase changed transformed wavefronts to be subsequently detected by detector 1514.

Figure 16:
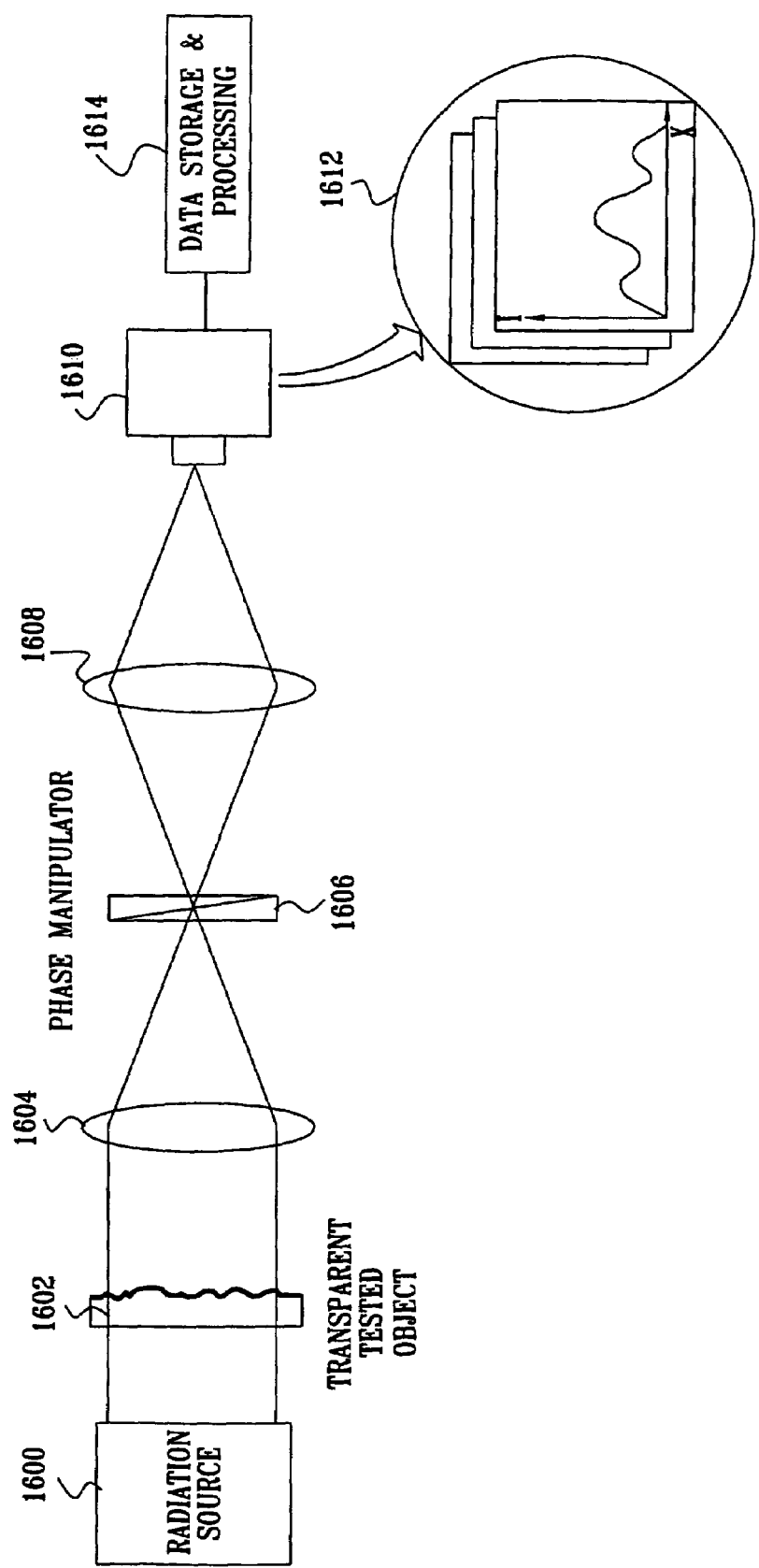
FIG. 16 is a simplified partially schematic, partially pictorial illustration of a system for object inspection employing the functionality and structure of FIGS. 1A and 1B.

Reference is now made to FIG. 16, which is a simplified partially schematic, partially pictorial illustration of a system for object inspection employing the functionality and structure of FIGS. 1A and 1B. As seen in FIG. 16, a beam of radiation, such as light or acoustic energy, is supplied from a radiation source 1600, optionally via a beam expander, onto at least partially transparent object to be inspected 1602. The radiation transmitted through the inspected object 1602, is an object inspection wavefront, which has an amplitude and a phase, and which contains information about the object 1602. At least part of the radiation transmitted through object 1602 is focused via a focusing lens 1604 onto a phase manipulator 1606, which is preferably located at the image plane of radiation source 1600.

The phase manipulator 1606 may be, for example, a spatial light modulator or a series of different transparent, spatially non-uniform objects. It is appreciated that phase manipulator 1606 can be configured such that a substantial part of the radiation focused thereonto is reflected therefrom. Alternatively the phase manipulator 1606 can be configured such that a substantial part of the radiation focused thereonto is transmitted therethrough.

A second lens 1608 is arranged so as to image object 1602 onto a detector 1610, such as a CCD detector. Preferably, the second lens 1608 is arranged such that the detector 1610 lies in its focal plane. The output of detector 1610, an example of which is a set of intensity maps designated by reference numeral 1612, is preferably supplied to data storage and processing circuitry 1614, which preferably carries out functionality "C" described hereinabove with reference to FIG. 1A, providing an output indicating at least one and possibly both of the phase and the amplitude of the object inspection wavefront. This output is preferably further processed to obtain information about the object 1602, such as a mapping of the object's thickness, refractive index or transmission.

In accordance with one preferred embodiment of the present invention, the beam of radiation supplied from radiation source 1600 has a narrow wavelength band about a given central wavelength, and the object 1602 is substantially uniform in material and other optical properties, causing the phase of the radiation transmitted through object 1602 to be proportional to thickness of the object 1602.

In accordance with one more preferred embodiment of the present invention, the beam of radiation supplied from radiation source 1600 has a narrow wavelength band about a given central wavelength, and the object 1602 is substantially uniform in thickness, causing the phase of the radiation transmitted through object 1602 to be proportional to optical properties, such as refraction index or density, of the object 1602. It is appreciated that object 1602 may be any optical conduction element, such as an optical fiber.

In accordance with another preferred embodiment of the present invention, the beam of radiation supplied from radiation source 1600 has at least two narrow wavelength bands, each centered about a different wavelength, designated $\lambda_1, \ldots, \lambda_n$. In such a case, the radiation transmitted through object 1602 has at least two wavelength components, each centered around a wavelength $\lambda_1, \ldots, \lambda_n$ and at least two indications of the phase of the object inspection wavefront are obtained. Each such indication corresponds to a different wavelength component of the transmitted radiation. These at least two indications may be subsequently combined to enable enhanced mapping of the properties, such as thickness, of object 1602, by avoiding ambiguity in the mapping, known as $2\pi$ ambiguity, when the value of the mapping at a given spatial location in the object exceeds the value of the mapping at a different spatial location in the object by the largest of the different wavelengths $\lambda_1, \ldots, \lambda_n$. A proper choice of the wavelengths $\lambda_1, \ldots, \lambda_n$, may lead to elimination of this ambiguity when the difference in values of the mapping at different locations is smaller than the multiplication product of all the wavelengths.

In accordance with still another preferred embodiment of the present invention, the phase manipulator 1606 applies a plurality of different spatial phase changes to the radiation wavefront transmitted through object 1602 and Fourier transformed by lens 1604. Application of the plurality of different spatial phase changes produces a plurality of differently phase changed transformed wavefronts which may be subsequently detected by detector 1610.

In accordance with yet another preferred embodiment of the present invention, at least three different spatial phase changes are applied by phase manipulator 1606, resulting in at least three different intensity maps 1612. The at least three intensity maps 1612 are employed by the data storage and processing circuitry 1614 to obtain an output indicating at least the phase of the object inspection wavefront. In such a case, the data storage and processing circuitry 1614, carries out functionality "C" described hereinabove with reference to FIG. 1A, preferably in a manner described hereinabove with reference to FIG. 13, where the wavefront being analyzed (FIG. 13) is the object inspection wavefront.

Additionally, in accordance with a preferred embodiment of the present invention, the beam of radiation supplied from radiation source 1600 comprises a plurality of different wavelength components, thereby providing a plurality of wavelength components in the object inspection wavefront and subsequently in the transformed wavefront impinging on phase manipulator 1606. In this case the phase manipulator 1606 may be an object, at least one of whose thickness, refractive index and surface geometry varies spatially. This spatial variance of the phase manipulator generates a different spatial phase change for each of the wavelength components, thereby providing a plurality of differently phase changed transformed wavefronts to be subsequently detected by detector 1610.

Figure 17:
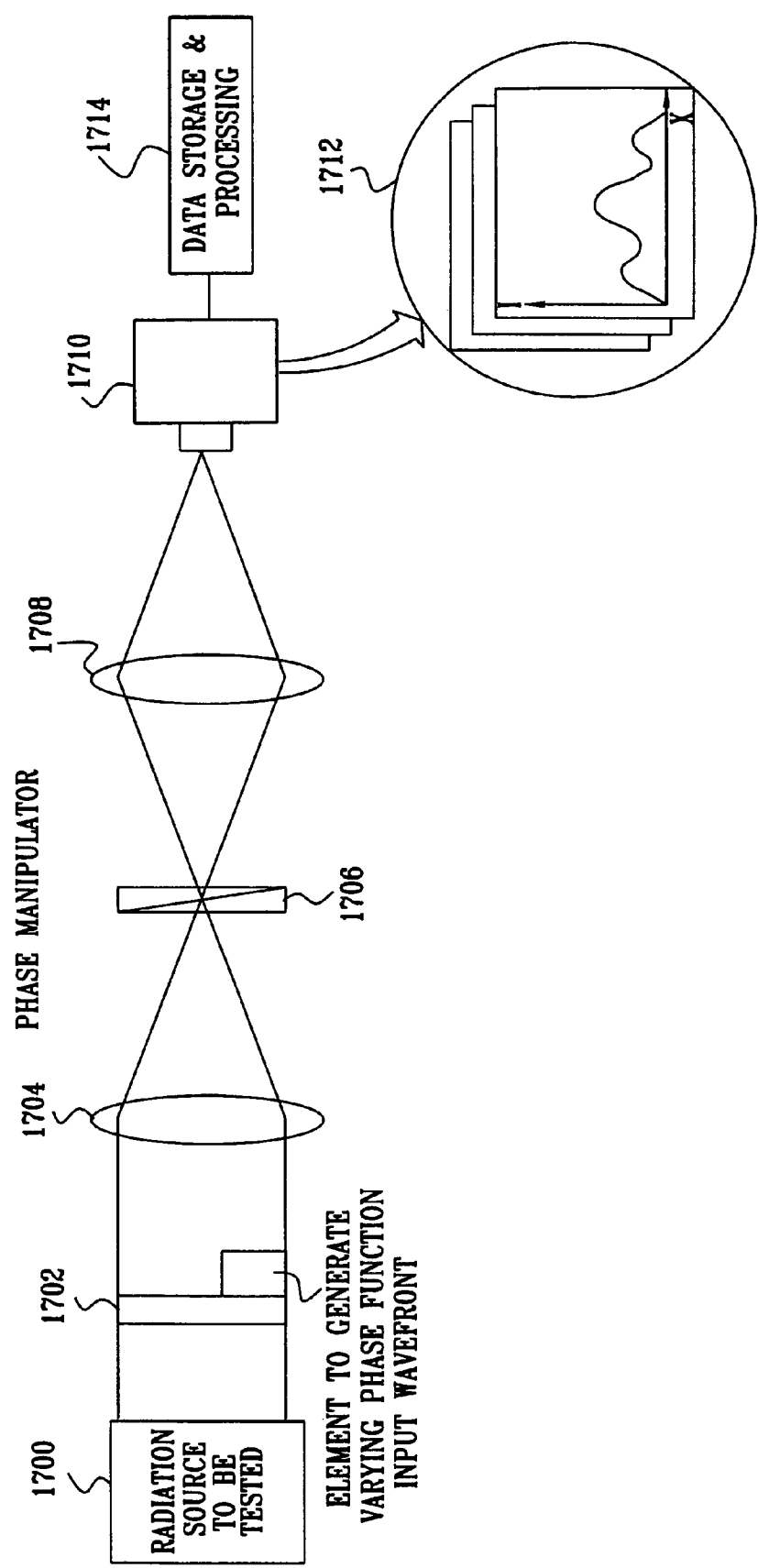
FIG. 17 is a simplified partially schematic, partially pictorial illustration of a system for spectral analysis employing the functionality and structure of FIGS. 1A and 1B.

Reference is now made to FIG. 17, which is a simplified partially schematic, partially pictorial illustration of a system for spectral analysis employing the functionality and structure of FIGS. 1A and 1B. As seen in FIG. 17, a beam of radiation, such as light or acoustic energy, is supplied from a radiation source to be tested 1700, optionally via a beam expander, onto a known element 1702, such as an Etalon or a plurality of Etalons. Element 1702 is intended to generate an input wavefront, having at least varying phase or intensity. The radiation transmitted through the element 1702, is a spectral analysis wavefront, which has an amplitude and a phase, and which contains information about the spectrum of the radiation source 1700. At least part of the radiation transmitted through element 1702 is focused via a focusing lens 1704 onto a phase manipulator 1706, which is preferably located at the image plane of radiation source 1700.

The phase manipulator 1706 may be, for example, a spatial light modulator or a series of different transparent, spatially non-uniform objects. It is appreciated that phase manipulator 1706 can be configured such that a substantial part of the radiation focused thereonto is reflected therefrom. Alternatively the phase manipulator 1706 can be configured such that a substantial part of the radiation focused thereonto is transmitted therethrough.

A second lens 1708 is arranged so as to image element 1702 onto a detector 1710, such as a CCD detector. Preferably, the second lens 1708 is arranged such that the detector 1710 lies in its focal plane. The output of detector 1710, an example of which is a set of intensity maps designated by reference numeral 1712, is preferably supplied to data storage and processing circuitry 1714, which preferably carries out functionality "C" described hereinabove with reference to FIG. 1A, providing an output indicating at least one and possibly both of the phase and the amplitude of the spectral analysis wavefront. This output is preferably further processed to obtain information about the radiation source 1700, such as the spectrum of the radiation supplied from radiation source 1700.

In accordance with a preferred embodiment of the present invention, the spectral analysis wavefront is obtained by reflecting the radiation supplied from radiation source 1700 from element 1702.

In accordance with another preferred embodiment of the present invention, the spectral analysis wavefront is obtained by transmitting the radiation supplied from radiation source 1700 through element 1702.

In accordance with one more preferred embodiment of the present invention, the beam of radiation supplied from radiation source 1700 has a narrow wavelength band about a central wavelength, causing the phase of the radiation impinged on the object 1702 to be inversely proportional to the central wavelength supplied from radiation source 1700 and related to at least one of a surface characteristic and thickness of element 1702.

In accordance with another preferred embodiment of the present invention, the plurality of intensity maps 1712 are employed by the data storage and processing circuitry 1714, to obtain an output indicating at least one and possibly both of the phase and amplitude of the spectral analysis wavefront by expressing the plurality of intensity maps as at least one mathematical function of phase and amplitude of the spectral analysis wavefront and of plurality of different phase changes applied by phase manipulator 1706, wherein at least one and possibly both of the phase and amplitude is unknown and a function generating the different phase changes is known. This at least one mathematical function is subsequently employed to obtain an output indicating at least the phase of the spectral analysis wavefront.

In accordance with still another preferred embodiment of the present invention, the phase manipulator 1706 applies a plurality of different spatial phase changes to the radiation wavefront transmitted through element 1702 and Fourier transformed by lens 1704. Application of the plurality of different spatial phase changes produces a plurality of differently phase changed transformed wavefronts which may be subsequently detected by detector 1710.

In accordance with yet another preferred embodiment of the present invention, at least three different spatial phase changes are applied by phase manipulator 1706, resulting in at least three different intensity maps 1712. The at least three intensity maps are employed by the data storage and processing circuitry 1714 to obtain an output indicating at least the phase of the spectral analysis wavefront. In such a case, the data storage and processing circuitry 1714, carries out functionality "C" described hereinabove with reference to FIG. 1A, preferably in a manner described hereinabove with reference to FIG. 13, where the wavefront being analyzed (FIG. 13) is the spectral analysis wavefront.

Additionally, in accordance with a preferred embodiment of the present invention, the beam of radiation supplied from radiation source 1700 comprises a plurality of different wavelength components, thereby providing a plurality of wavelength components in the spectral analysis wavefront and subsequently in the transformed wavefront impinging on phase manipulator 1706. In this case the phase manipulator may be an object, at least one of whose thickness, refractive index and surface geometry varies spatially. This spatial variance of the phase manipulator generates a different spatial phase change for each of the wavelength components, thereby providing a plurality of differently phase changed transformed wavefronts to be subsequently detected by detector 1710.

In accordance with an embodiment of the present invention, the phase manipulator 1706 comprises a plurality of objects, each characterized in that at least one of its thickness and refractive index varies spatially. The spatial variance of the thickness or of the refractive index of the plurality of objects may be selected in a way such that the phase changes applied by phase manipulator 1706 differ to a selected predetermined extent for at least some of the wavelength components supplied by radiation source 1700.

A specific selection of the objects is such that the phase change applied to an expected wavelength of radiation source differs substantially from the phase change applied to an actual wavelength of the radiation source. Alternatively, the spatial variance of the thickness or refractive index of the plurality of objects may be selected in a way such that the phase changes applied by phase manipulator 1706 are identical for at least some of the plurality of different wavelength components wavelength components supplied by radiation source 1700.

In accordance with another embodiment of the present invention, the known element 1702 comprises a plurality of objects, each characterized in that at least one of its thickness and refractive index varies spatially. The spatial variance of the thickness or of the refractive index of the plurality of objects may be selected in a way such that the wavelength components of the input wavefront, generated by passing the wavelength components of the radiation supplied by radiation source 1700 through the element 1702, differ to a selected predetermined extent for at least some of the wavelength components supplied by radiation source 1700.

A specific selection of the objects is such that the wavelength component of the input wavefront generated by an expected wavelength of radiation source differs substantially from the wavelength component of the input wavefront generated by an actual wavelength of the radiation source. Alternatively, the spatial variance of the thickness or refractive index of the plurality of objects may be selected in a way such that the wavelength components of the input wavefront, generated by passing the wavelength components of the radiation supplied by radiation source 1700 through the element 1702, are identical for at least some of the wavelength components supplied by radiation source 1700.

Figure 18:
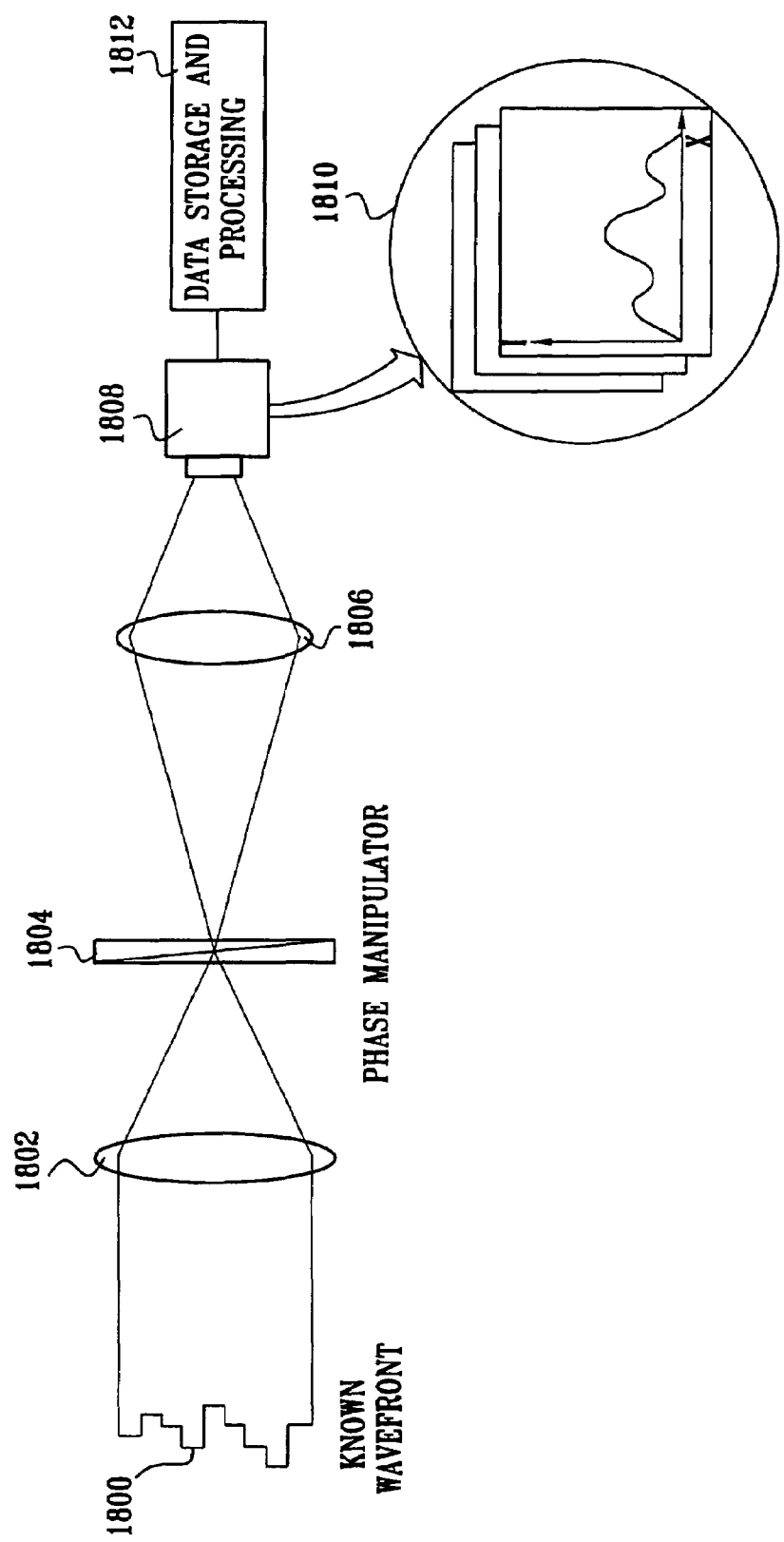
FIG. 18 is a simplified partially schematic, partially pictorial illustration of a system for phase-change analysis employing the functionality and structure of FIGS. 1A and 1B.

Reference is now made to FIG. 18, which is a simplified partially schematic, partially pictorial illustration of a system for phase-change analysis employing the functionality and structure of FIGS. 1A and 1B. As seen in FIG. 18, a known wavefront 1800, which is a phase change analysis wavefront, having an amplitude and a phase, is focused via a focusing lens 1802, preferably performing a Fourier transform to wavefront 1800, onto a phase manipulator 1804, which is preferably located at the focal plane of lens 1802. The phase manipulator applies a plurality of different phase changes to the transformed phase change analysis wavefront.

The phase manipulator 1804 may be, for example, a spatial light modulator or a series of different transparent, spatially non-uniform objects. It is appreciated that phase manipulator 1804 can be configured such that a substantial part of the radiation focused thereonto is reflected therefrom. Alternatively the phase manipulator 1804 can be configured such that a substantial part of the radiation focused thereonto is transmitted therethrough.

A second lens 1806 is arranged so as to image wavefront 1800 onto a detector 1808, such as a CCD detector. Preferably, the second lens 1806 is arranged such that the detector 1808 lies in its focal plane. The output of detector 1808, an example of which is a set of intensity maps designated by reference numeral 1810, is preferably supplied to data storage and processing circuitry 1812, which employs the plurality of intensity maps to obtain an output indication of differences between the plurality of different phase changes applied by the phase manipulator 1804.

In accordance with one preferred embodiment of the present invention, lateral shifts appear in the plurality of different phase changes. These may be produced, for example, by vibrations of the phase manipulator or by impurities in the phase manipulator. Consequently, corresponding changes appear in the plurality of intensity maps 1810, and result in obtaining an indication of these lateral shifts.

In accordance with another preferred embodiment of the present invention, the plurality of intensity maps 1810 are employed by the data storage and processing circuitry 1812 to obtain an output indicating the differences between the plurality of different phase changes applied by the phase manipulator 1804, by expressing the plurality of intensity maps as at least one mathematical function of phase and amplitude of the phase change analysis wavefront and of the plurality of different phase changes applied by phase manipulator 1804, where at least the phase and amplitude of the wavefront 1800 are known and the plurality of different phase changes are unknown. This at least one mathematical function is subsequently employed to obtain an output indicating at least the differences between the plurality of different phase changes.

In accordance with still another preferred embodiment of the present invention, the phase manipulator 1804 applies a plurality of different spatial phase changes to the wavefront 1800 Fourier transformed by lens 1802. Application of the plurality of different spatial phase changes provides a plurality of differently phase changed transformed wavefronts which may be subsequently detected by detector 1808.

In accordance with yet another preferred embodiment of the present invention, at least three different spatial phase changes are applied by phase manipulator 1804, resulting in at least three different intensity maps 1810. The at least three intensity maps are employed by the data storage and processing circuitry 1812 to obtain an output indicating at least the differences between the plurality of different phase changes. In such a case, the data storage and processing circuitry 1814, carries out functionality "C" described hereinabove with reference to FIG. 1A, preferably in a manner similar to the manner described hereinabove with reference to FIG. 13, where the wavefront being analyzed (FIG. 13) is the known phase change analysis wavefront, and the spatial phase changes applied by phase manipulator 1804 are unknown.

Additionally, in accordance with a preferred embodiment of the present invention, the wavefront 1800 comprises a plurality of different wavelength components, thereby providing a plurality of wavelength components in the transformed wavefront impinging on phase manipulator 1804. In this case the phase manipulator may be an object, at least one of whose thickness, refractive index and surface geometry varies spatially. This spatial variance of the phase manipulator generates a different spatial phase change for each of the wavelength components, thereby providing a plurality of differently phase changed transformed wavefronts to be subsequently detected by detector 1808.

Additionally, in accordance with another embodiment of the present invention, phase manipulator 1804 applies one phase change to the radiation focused onto each spatial location thereon, resulting in one intensity map 1810, as an output of detector 1808. In such a case, the data storage and processing circuitry 1812 employs the intensity map and the known wavefront 1800 to obtain at least an output indicating the phase change applied by phase manipulator 1804.

In accordance with the foregoing methodology, the phase change applied by the phase manipulator may be a phase delay, having a value selected from one of a plurality of pre-determined values, including a possible value of zero phase delay and the output indication of the phase change obtained by data storage and processing circuitry 1812 is the value of the phase delay. In such a case, the phase manipulator may be media which stores information by different values of the phase delays at each of a multiplicity of different locations thereon, where the value of the phase delay constitutes the stored information. The stored information, encoded in the different values of the phase delays, is retrieved by data storage and processing circuitry 1812. It is appreciated that in such a case, wavefront 1800 may also comprise a plurality of different, wavelength components, resulting in a plurality of intensity maps and consequently in an increase of the information encoded on the phase manipulator at each of the multiplicity of different locations.

Figure 19:
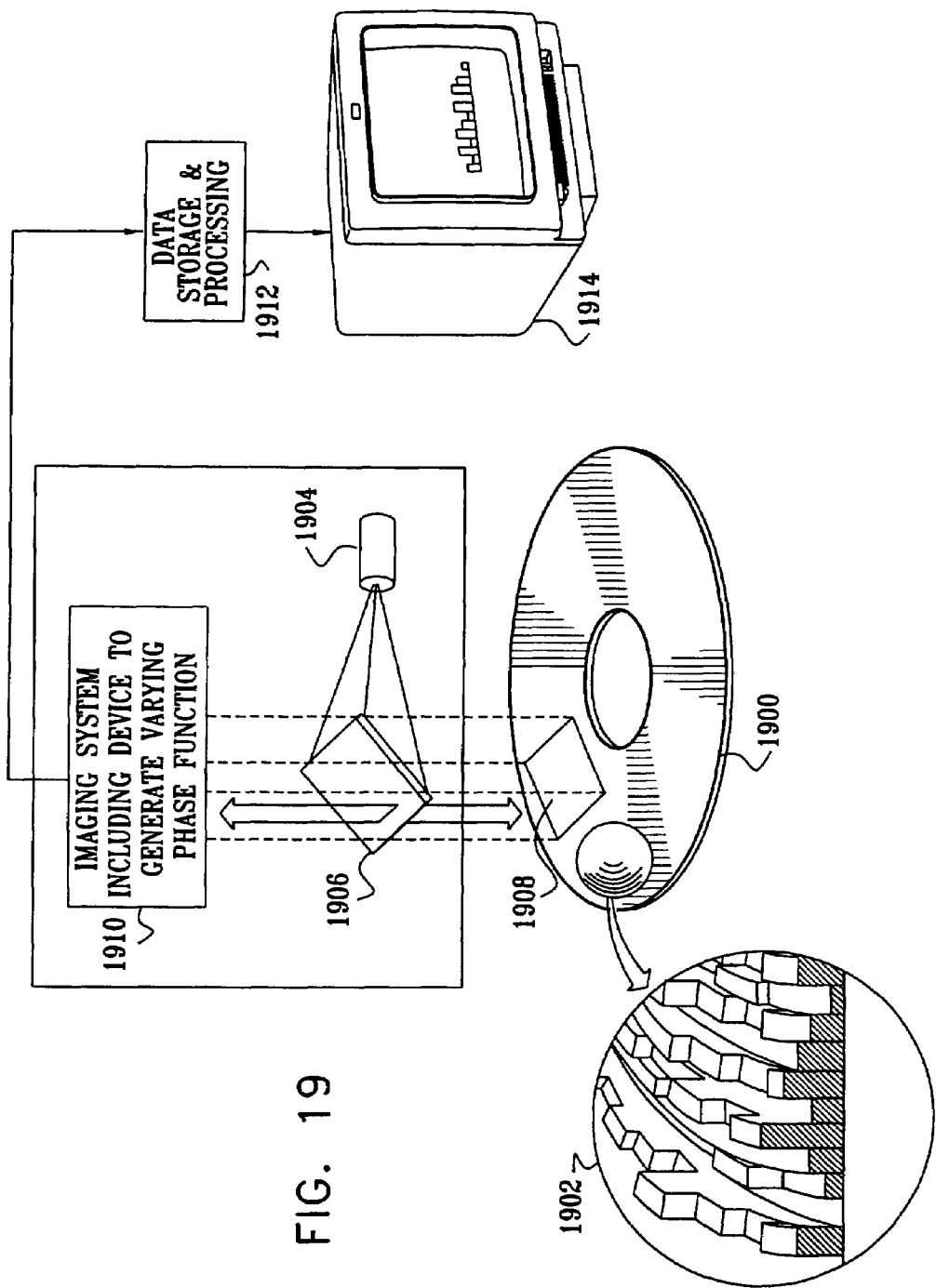
FIG. 19 is a simplified partially schematic, partially pictorial illustration of a system for stored data retrieval employing the functionality and structure of FIGS. 1A and 1B.

Reference is now made to FIG. 19, which is a simplified partially schematic, partially pictorial illustration of a system for stored data retrieval employing the functionality and structure of FIGS. 1A and 1B. As seen in FIG. 19, optical storage media 1900, such as a DVD or compact disk, has information encoded thereon by selecting the height of the media at each of a multiplicity of different locations thereon, as shown in enlargement and designated by reference numeral 1902. At each location on the media, the height of the media can be one of several given heights or levels. The specific level of the media at that location determines the information stored at that location.

A beam of radiation, such as light or acoustic energy, is supplied from a radiation source 1904, such as a laser or a LED, optionally via a beam expander, onto a beam splitter 1906, which reflects at least part of the radiation onto the surface of the media 1900. The radiation reflected from an area 1908 on the media, onto which the radiation impinges, is a stored data retrieval wavefront, which has an amplitude and a phase, and which contains information stored in area 1908. At least part of the radiation incident on area 1908 is reflected from the area 1908 and transmitted via the beam splitter 1906 onto an imaging system 1910, which may include a phase manipulator or other device which generates a varying phase function.

Imaging system 1910 preferably carries out functionalities "A" and "B" described hereinabove with reference to FIG. 1A, obtaining a plurality of differently phase changed transformed wavefronts corresponding to the stored data retrieval wavefront and obtaining a plurality of intensity maps of the plurality of phase changed transformed wavefronts.

Preferably, imaging system 1910 comprises a first lens 1508 (FIG. 15), a phase manipulator 1510 (FIG. 15), a second lens 1512 (FIG. 15) and a detector 1514 (FIG. 15). The outputs of imaging system 1910 are supplied to data storage and processing circuitry 1912, which preferably carries out functionality "C" described hereinabove with reference to FIG. 1A, providing an output indicating at least one and possibly both of the phase and amplitude of the stored data retrieval wavefront. This output is preferably further processed to read out the information encoded in area 1908 of media 1900 and displayed on display unit 1914.

In accordance with a preferred embodiment of the present invention, the beam of radiation supplied from radiation source 1904 has a narrow wavelength band about a given central wavelength, causing the phase of the radiation reflected from media 1900 to be proportional to geometrical variations in the media 1900, which contain the encoded information, the proportion being an inverse linear function of the central wavelength of the radiation.

In accordance with another preferred embodiment of the present invention, the beam of radiation supplied from radiation source 1904 has at least two narrow wavelength bands, each centered about a different wavelength, designated $\lambda_1, \ldots, \lambda_n$. In such a case, the radiation reflected from area 1908 in media 1900 has at least two wavelength components, each centered around a wavelength $\lambda_1, \ldots, \lambda_n$.

At least two indications of the phase of the stored data retrieval wavefront are obtained, each such indication corresponding to a different wavelength component of the reflected radiation. These at least two indications may be subsequently combined to enhance mapping of the surface of area 1908 of media 1900 and therefore enhance retrieval of the information, by avoiding an ambiguity in the mapping, known as $2\pi$ ambiguity, when the value of the height of the media at a given location exceeds the largest of the different wavelengths $\lambda_1, \ldots, \lambda_n$.

In such a case, the range of possible heights at each location in area 1908 can exceed the value of the largest of the different wavelengths, without ambiguity in the reading of the heights. This extended dynamic range enables storing more information on media 1900 than would otherwise be possible. A proper choice of the wavelengths $\lambda_1, \ldots, \lambda_n$, may lead to elimination of this ambiguity when the difference of heights of the media in area 1908 at different locations is smaller than the multiplication product of all the wavelengths.

In accordance with still another preferred embodiment of the present invention, a phase manipulator incorporated in imaging system 1910 applies a plurality of different spatial phase changes to the radiation wavefront reflected from media 1900 and Fourier transformed by a lens, also incorporated in imaging system 1910. Application of the plurality of different spatial phase changes provides a plurality of differently phase changed transformed wavefronts which may be subsequently detected by a detector incorporated in imaging system 1910.

In accordance with yet another preferred embodiment of the present invention, at least three different spatial phase changes are applied by a phase manipulator incorporated in imaging system 1910, resulting in an output from imaging system 1910 of at least three different intensity maps. The at least three intensity maps are employed by the data storage and processing circuitry 1912 to obtain an output indicating at least the phase of the stored data retrieval wavefront. In such a case, the data storage and processing circuitry 1912, carries out functionality "C" described hereinabove with reference to FIG. 1A, preferably in a manner described hereinabove with reference to FIG. 13, where the wavefront being analyzed (FIG. 13) is the stored data retrieval wavefront.

Additionally, in accordance with an embodiment of the present invention, the beam of radiation supplied from radiation source 1904 comprises a plurality of different wavelength components, thereby providing a plurality of wavelength components in the stored data retrieval wavefront and subsequently in the transformed wavefront impinging on a phase manipulator incorporated into imaging system 1910. In this case the phase manipulator may be an object, at least one of whose thickness, refractive index and surface geometry varies spatially. This spatial variance of the phase manipulator generates a different spatial phase change for each of the wavelength components, thereby providing a plurality of differently phase changed transformed wavefronts to be subsequently detected by a detector incorporated in imaging system 1910.

In accordance with another embodiment of the present invention, information is encoded on media 1900 by selecting the height of the media at each given location to be such that the intensity value of the intensity map resulting from light reflected from the location and passing through imaging system 1910 lies within a predetermined range of values. This range corresponds to an element of the information stored at the location. By employing the plurality of intensity maps, multiple intensity values are realized for each location, each intensity value lying within a specific range of values. The resulting plurality of ranges of intensity values provide multiple elements of information for each location on the media 1900.

It is appreciated that in such a case, retrieving the information stored at area 1908 on the media from the outputs of imaging system 1910 may be performed by data storage and processing circuitry 1912 in a straight-forward manner, as by mapping each of the resulting intensity values at each location to their corresponding ranges, and subsequently to the information stored at the location.

Preferably, the foregoing methodology also includes use of a phase manipulator incorporated in imaging system 1910, that applies an at least time-varying phase change function to the transformed data retrieval wavefront impinging thereon. This time-varying phase change function provides the plurality of intensity maps.

Alternatively or additionally, the beam of radiation supplied from radiation source 1904 comprises a plurality of different wavelength components, thereby providing a plurality of wavelength components in the stored data retrieval wavefront. The plurality of differently phase changed transformed wavefronts are obtained in imaging system 1910 by applying at least one phase change to the plurality of different wavelength components of the stored data retrieval wavefront. The phase changed transformed stored data retrieval wavefront can be detected by a single detector or alternatively separated, as by a dispersion element, into its separate plurality of different wavelength components, each component being detected by a different detector.

In accordance with yet another embodiment of the present invention, media 1900 may have different reflectivity coefficients for the radiation supplied from light source 1904 at each of a multiplicity of different locations on the media. At each location on the media, a different percentage of the radiation may be reflected. The percentage may have one of several given values, where the specific value may at least partially determine the information stored at that location.

In such a case, the information encoded on media 1900 may be encoded by selecting the height of the media at each of a multiplicity of different locations on the media and by selecting the reflectivity of the media at each of a multiplicity of different locations on the media. In such a case, more information can be stored at each location on the media, than could otherwise be stored. Furthermore, in such a case, employing an indication of the amplitude and phase of the stored data retrieval wavefront to obtain the encoded information includes employing the indication of the phase to obtain the information encoded by selecting the height of the media and employing the indication of the amplitude to obtain said information encoded by selecting the reflectivity.

In accordance with still another embodiment of the present invention, the information is encoded onto media 1900 at several layers in the media. The information is encoded on the media by selecting the height of the media at each of multiplicity of different locations on each layer of the media. Each of these layers, placed one on top of the other in media 1900, is partially reflecting and partially transmitting. The beam of radiation from source 1904 impinging onto media 1900 is partially reflected from the top, first layer of the media, and partially transmitted to the layers lying therebelow. The energy transmitted by the second layer is partially reflected and partially transmitted to the layers lying therebelow, and so on, until the radiation transmitted through all the layers is partially reflected from the undermost layer. In such a case, radiation source 1904 preferably includes a focusing system that focuses the radiation onto each one of the layers of media 1900 in order to retrieve the information stored on that layer. Alternatively or additionally, imaging system 1910 may include confocal microscopy elements operative to differentiate between the different layers.

It is appreciated that area 1908 of media 1900 may be a relatively small area, comprising a single location on which information is encoded and possibly also neighboring locations. In such a case, the detector incorporated in imaging system 1910 may define only a single or several detection pixels. Additionally, the output indicating at least one and possibly both of the phase and amplitude of the stored data retrieval wavefront provided by circuitry 1912, includes at least one and possibly both of the height of the media and the reflectivity of the media at the location or locations covered by area 1908.

In accordance with yet another embodiment of the present invention, the stored data retrieval wavefront comprises at least one one-dimensional component, corresponding to at least one one-dimensional part of area 1908 on media 1900. In such a case, the imaging system 1910 is preferably similar to the imaging system described hereinabove with reference to FIG. 10B. It preferably includes a first lens, such as cylindrical lens 1086 (FIG. 10B).

The first lens preferably produces a one-dimensional Fourier transform, performed along an axis extending perpendicularly to the direction of propagation of the data retrieval wavefront, thereby providing at least one one-dimensional component of the transformed wavefront in a dimension perpendicular to direction of propagation. The first lens, such as lens 1086, focuses the stored data retrieval wavefront onto a phase manipulator, such as a single axis displaceable phase manipulator 1087 (FIG. 10B), which is preferably located at the focal plane of lens 1086. The phase manipulator 1087 applies a plurality of different phase changes to each of the at least one one-dimensional components of the transformed wavefront, thereby obtaining at least one one-dimensional component of the plurality of phase changed transformed wave fronts.

Additionally the imaging system may include a second lens, such as cylindrical lens 1088 (FIG. 10B), arranged so as to image the at least one one-dimensional component of the stored data retrieval wavefront onto a detector 1089, such as a CCD detector. Additionally the plurality of intensity maps are employed by circuitry 1912 to obtain an output indicating al least one and possibly both of the amplitude and phase of the at least one one-dimensional component of the data retrieval wavefront.

Additionally, in accordance with the foregoing methodology, and as described hereinabove with reference to FIG. 10B, the phase manipulator 1087 preferably comprises a multiple local phase delay element, such as a spatially non-uniform transparent object, typically including several different phase delay regions, each arranged to apply a phase delay to one of the at least one one-dimensional component at a given position of the object along a phase manipulator axis, extending perpendicularly to the direction of propagation of the wavefront and perpendicular to the axis of the transform produced by lens 1086.

In such a case, there is provided relative movement between the imaging system 1910 and the media 1900 along the phase manipulator axis. This relative movement sequentially matches different phase delay regions with different wavefront components, corresponding to different parts of area 1908 on media 1900, such that preferably each wavefront component passes through each phase delay region of the phase manipulator.

It is appreciated that the relative movement between the imaging system 1910 and the at least one one-dimensional wavefront component can be obtained by the rotation of media 1900 about its axis, while the imaging system is not moving.

It is a particular feature of this embodiment, that each of the at least one one-dimensional component of the wavefront is separately processed. Thus, each of the at least one one-dimensional wavefront component, corresponding to a one-dimensional part of area 1908, is focused by a separate portion of the first cylindrical lens of imaging system 1910, is imaged by a corresponding separate portion of the second cylindrical lens and passes through a distinct region of the phase manipulator. The images of each of the one-dimensional parts of area 1908 at the detector incorporated in imaging system 1910 are thus separate and distinct images. It is appreciated that these images may appear on separate detectors or on a monolithic detector.

In accordance with an embodiment of the present invention, the transform applied to the stored data retrieval wavefront includes an additional Fourier transform. This additional Fourier transform may be performed by the first cylindrical lens of imaging system 1910 or by an additional lens and is operative to minimize cross-talk between different one-dimensional components of the wavefront. In such a case, preferably an additional transform, such as that provided by an additional lens adjacent to the second cylindrical lens, is applied to the phase changed transformed wavefront. In such a case, preferably a further transform is applied to the phase changed transformed wavefront. This further transform may be performed by the second cylindrical lens of imaging system 1910 or by an additional lens.

Figure 20:
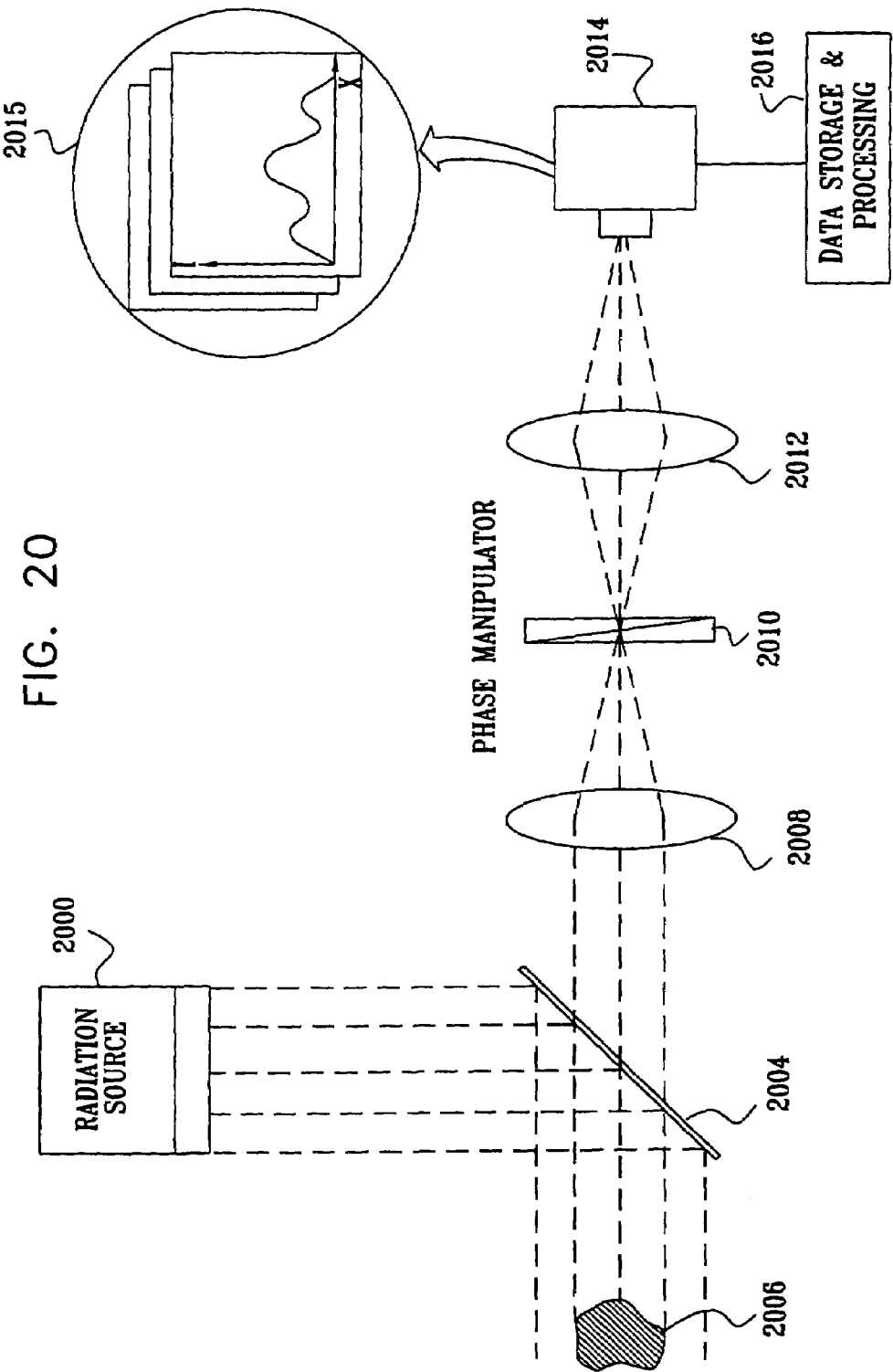
FIG. 20 is a simplified partially schematic, partially pictorial illustration of a system for 3-dimensional imaging employing the functionality and structure of FIGS. 1A and 1B.

Reference is now made to FIG. 20, which is a simplified partially schematic, partially pictorial illustration of a system for 3-dimensional imaging employing the functionality and structure of FIGS. 1A and 1B. As seen in FIG. 20, a beam of radiation, such as light or acoustic energy, is supplied from a radiation source 2000, optionally via a beam expander, onto a beam splitter 2004, which reflects at least part of the radiation onto a 3-dimensional object 2006 to be imaged. The radiation reflected from the object 2006, is a 3-dimensional imaging wavefront, which has an amplitude and a phase, and which contains information about the object 2006. At least part of the radiation incident on the surface of object 2006 is reflected from the object 2006 and transmitted via the beam splitter 2004 and focused via a focusing lens 2008 onto a phase manipulator 2010, which is preferably located at the image plane of radiation source 2000.

The phase manipulator 2010 may be, for example, a spatial light modulator or a series of different transparent, spatially non-uniform objects. It is appreciated that phase manipulator 2010 can be configured such that a substantial part of the radiation focused thereonto is reflected therefrom. Alternatively the phase manipulator 2010 can be configured such that a substantial part of the radiation focused thereonto is transmitted therethrough.

A second lens 2012 is arranged so as to image object 2006 onto a detector 2014, such as a CCD detector. Preferably the second lens 2012 is arranged such that the detector 2014 lies in its focal plane. The output of detector 2014, an example of which is a set of intensity maps designated by reference numeral 2015, is preferably supplied to data storage and processing circuitry 2016, which preferably carries out functionality "C" described hereinabove with reference to FIG. 1A, providing an output indicating at least one and possibly both of the phase and amplitude of the 3-dimensional imaging wavefront. This output is preferably further processed to obtain information about the object 2006, such as the 3-dimensional shape of the object.

In accordance with a preferred embodiment of the present invention, the beam of radiation supplied from radiation source 2000 has a narrow wavelength band about a given central wavelength, causing the phase of the radiation reflected from object 2006 to be proportional to geometrical variations in the surface 2006, the proportion being an inverse linear function of the central wavelength of the radiation.

In accordance with another preferred embodiment of the present invention, the beam of radiation supplied from radiation source 2000 has at least two narrow wavelength bands, each centered about a different wavelength, designated $\lambda_1, \ldots, \lambda_n$. In such a case, the radiation reflected from the object 2006 has at least two wavelength components, each centered around a wavelength $\lambda_1, \ldots, \lambda_n$ and at least two indications of the phase of the 3-dimensional imaging wavefront are obtained. Each such indication corresponds to a different wavelength component of the reflected radiation. These at least two indications may be subsequently combined to enable enhanced imaging of the object 2006, by avoiding $2\pi$ ambiguity in the 3-dimensional imaging.

In accordance with still another preferred embodiment of the present invention, the phase manipulator 2010 applies a plurality of different spatial phase changes to the radiation wavefront reflected from surface 2006 and Fourier transformed by lens 2008. Application of the plurality of different spatial phase changes provides a plurality of differently phase changed transformed wavefronts which may be subsequently detected by detector 2014.

In accordance with yet another preferred embodiment of the present invention, at least three different spatial phase changes are applied by phase manipulator 2010, resulting in at least three different intensity maps 2015. The at least three intensity maps are employed by the data storage and processing circuitry 2016 to obtain an output indicating at least the phase of the 3-dimensional imaging wavefront. In such a case, the data storage and processing circuitry 2016, carries out functionality "C" described hereinabove with reference to FIG. 1A, preferably in a manner described hereinabove with reference to FIG. 13, where the wavefront being analyzed (FIG. 13) is the 3-dimensional imaging wavefront.

Additionally, in accordance with a preferred embodiment of the present invention, the beam of radiation supplied from radiation source 2000 comprises a plurality of different wavelength components, thereby providing a plurality of wavelength components in the 3-dimensional imaging wavefront and subsequently in the transformed wavefront impinging on phase manipulator 2010. In this case the phase manipulator 2010 may be an object, at least one of whose thickness, refractive index and surface geometry varies spatially. This spatial variance of the phase manipulator generates a different spatial phase change for each of the wavelength components, thereby providing a plurality of differently phase changed transformed wavefronts to be subsequently detected by detector 2014.

Reference is now made to FIG. 21A, which is a simplified partially schematic, partially pictorial illustration of wavefront analysis functionality operative in accordance with another preferred embodiment of the present invention. The functionality of FIG. 21A can be summarized as including the following sub-functionalities:

A. obtaining a plurality of differently amplitude changed transformed wavefronts corresponding to a wavefront being analyzed, which has an amplitude and a phase;

B. obtaining a plurality of intensity maps of the plurality of amplitude changed transformed wavefronts; and C. employing the plurality of intensity maps to obtain an output indicating at least one and possibly both of the phase and the amplitude of the wavefront being analyzed.

As seen in FIG. 21A, the first sub-functionality, designated "A" may be realized by the following functionalities:

A wavefront, which may be represented by a plurality of point sources of light, is generally designated by reference numeral 2100. Wavefront 2100 has a phase characteristic which is typically spatially non-uniform, shown as a solid line and indicated generally by reference numeral 2102. Wavefront 2100 also has an amplitude characteristic which is typically spatially non-uniform, shown as a dashed line and indicated generally by reference numeral 2103. Such a wavefront may be obtained in a conventional manner by receiving light from any suitable object, such as by reading an optical disk, for example, a DVD or compact disk 2104.

A principal purpose of the present invention is to measure the phase characteristic, such as that indicated by reference numeral 2102, which is not readily measured. Another purpose of the present invention is to measure the amplitude characteristic, such as that indicated by reference numeral 2103 in an enhanced manner. A further purpose of the present invention is to measure both the phase characteristic 2102 and the amplitude characteristic 2103. While there exist various techniques for carrying out such measurements, the present invention provides a methodology which is believed to be superior to those presently known, inter alia due to its relative insensitivity to noise.

A transform, indicated here symbolically by reference numeral 2106, is applied to the wavefront being analyzed 2100, thereby to obtain a transformed wavefront. A preferred transform is a Fourier transform. The resulting transformed wavefront is symbolically indicated by reference numeral 2108.

A plurality of different amplitude changes, preferably spatial amplitude changes, represented by optical attenuation components 2110, 2112 and 2114 are applied to the transformed wavefront 2108, thereby to obtain a plurality of differently amplitude changed transformed wavefronts, represented by reference numerals 2120, 2122 and 2124 respectively. It is appreciated that the illustrated difference between the individual ones of the plurality of differently amplitude changed transformed wavefronts is that portions of the transformed wavefront are attenuated differently relative to the remainder thereof.

As seen in FIG. 21A, the second sub-functionality, designated "B", may be realized by applying a transform, preferably a Fourier transform, to the plurality of differently amplitude changed transformed wavefronts. Alternatively, the sub-functionality B may be realized without the use of a Fourier transform, such as by propagation of the differently amplitude changed transformed wavefronts over an extended space. Finally, functionality B requires detection of the intensity characteristics of plurality of differently amplitude changed transformed wavefronts. The outputs of such detection are the intensity maps, examples of which are designated by reference numerals 2130, 2132 and 2134.

As seen in FIG. 21A, the third sub-functionality, designated "C" may be realized by the following functionalities:

expressing, such as by employing a computer 2136, the plurality of intensity maps, such as maps 2130, 2132 and 2134, as at least one mathematical function of phase and amplitude of the wavefront being analyzed and of the plurality of different amplitude changes, wherein at least one and possibly both of the phase and the amplitude are unknown and the plurality of different amplitude changes, typically represented by optical attenuation components 2110, 2112 and 2114 applied to the transformed wavefront 2108, are known; and employing, such as by means of the computer 2136, the at least one mathematical function to obtain an indication of at least one and possibly both of the phase and the amplitude of the wavefront being analyzed, here represented by the phase function designated by reference numeral 2138 and the amplitude function designated by reference numeral 2139, which, as can be seen, respectively represent the phase characteristics 2102 and the amplitude characteristics 2103 of the wavefront 2100. In this example, wavefront 2100 may represent the information contained in the compact disk or DVD 2104.

In accordance with an embodiment of the present invention, the plurality of intensity maps comprises at least four intensity maps. In such a case, employing the plurality of intensity maps to obtain an output indicating at least the phase of the wavefront being analyzed includes employing a plurality of combinations, each of at least three of the plurality of intensity maps, to provide a plurality of indications at least of the phase of the wavefront being analyzed.

Preferably, the methodology also includes employing the plurality of indications of at least the phase of the wavefront being analyzed to provide an enhanced indication at least of the phase of the wavefront being analyzed.

Also in accordance with an embodiment of the present invention, the plurality of intensity maps comprises at least four intensity maps. In such a case, employing the plurality of intensity maps to obtain an output indicating at least the amplitude of the wavefront being analyzed includes employing a plurality of combinations, each of at least three of the plurality of intensity maps, to provide a plurality of indications at least of the amplitude of the wavefront being analyzed.

Preferably, the methodology also includes employing the plurality of indications of at least the amplitude of the wavefront being analyzed to provide an enhanced indication at least of the amplitude of the wavefront being analyzed.

It is appreciated that in this manner, enhanced indications of both phase and amplitude of the wavefront may be obtained.

In accordance with a preferred embodiment of the present invention, at least some of the plurality of indications of the amplitude and phase are at least second order indications of the amplitude and phase of the wavefront being analyzed.

In accordance with one preferred embodiment of the present invention, the plurality of intensity maps are employed to provide an analytical output indicating the amplitude and phase.

Preferably, the amplitude changed transformed wavefronts are obtained by interference of the wavefront being analyzed along a common optical path.

In accordance with another preferred embodiment of the present invention, the plurality of intensity maps are employed to obtain an output indicating the phase of the wavefront being analyzed, which is substantially free from halo and shading off distortions, which are characteristic of many of the existing 'phase-contrast' methods.

In accordance with still another embodiment of the present invention, the plurality of intensity maps may be employed to obtain an output indicating the phase of the wavefront being analyzed by combining the plurality of intensity maps into a second plurality of combined intensity maps, the second plurality being less than the first plurality, obtaining at least an output indicative of the phase of the wavefront being analyzed from each of the second plurality of combined intensity maps and combining the outputs to provide an enhanced indication of the phase of the wavefront being analyzed.

In accordance with yet another embodiment of the present invention, the plurality of intensity maps may be employed to obtain an output indicating amplitude of the wavefront being analyzed by combining the plurality of intensity maps into a second plurality of combined intensity maps, the second plurality being less than the first plurality, obtaining at least an output indicative of the amplitude of the wavefront being analyzed from each of the second plurality of combined intensity maps and combining the outputs to provide an enhanced indication of the amplitude of the wavefront being analyzed.

Additionally in accordance with a preferred embodiment of the present invention, the foregoing methodology may be employed for obtaining a plurality of differently amplitude changed transformed wavefronts corresponding to a wavefront being analyzed, obtaining a plurality of intensity maps of the plurality of amplitude changed transformed wavefronts and employing the plurality of intensity maps to obtain an output of an at least second order indication of phase of the wavefront being analyzed.

Additionally or alternatively in accordance with a preferred embodiment of the present invention, the foregoing methodology may be employed for obtaining a plurality of differently amplitude changed transformed wavefronts corresponding to a wavefront being analyzed, obtaining a plurality of intensity maps of the plurality of amplitude changed transformed wavefronts and employing the plurality of intensity maps to obtain an output of an at least second order indication of amplitude of the wavefront being analyzed.

In accordance with yet another embodiment of the present invention, the obtaining of the plurality of differently amplitude changed transformed wavefronts comprises applying a transform to the wavefront being analyzed, thereby to obtain a transformed wavefront, and then applying a plurality of different phase and amplitude changes to the transformed wavefront, where each of these changes can be a phase change, an amplitude change or a combined phase and amplitude change, thereby to obtain a plurality of differently phase and amplitude changed transformed wavefronts.

In accordance with yet another embodiment of the present invention, a wavefront being analyzed comprises at least two wavelength components. In such a case, obtaining a plurality of intensity maps also includes dividing the amplitude changed transformed wavefronts according to the at least two wavelength components in order to obtain at least two wavelength components of the amplitude changed transformed wavefronts and in order to obtain at least two sets of intensity maps, each set corresponding to a different one of the at least two wavelength components of the amplitude changed transformed wavefronts.

Subsequently, the plurality of intensity maps are employed to provide an output indicating the amplitude and phase of the wavefront being analyzed by obtaining an output indicative of the phase of the wavefront being analyzed from each of the at least two sets of intensity maps and combining the outputs to provide an enhanced indication of phase of the wavefront being analyzed. In the enhanced indication, there is no $2\pi$ ambiguity once the value of the phase exceeds $2\pi$, which conventionally results when detecting phase of a single wavelength wavefront.

It is appreciated that the wavefront being analyzed may be an acoustic radiation wavefront.

It is also appreciated that the wavefront being analyzed may be an electromagnetic radiation wavefront, of any suitable wavelength, such as visible light, infrared, ultraviolet and X-ray radiation.

It is further appreciated that wavefront 2100 may be represented by a relatively small number of point sources and defined over a relatively small spatial region. In such a case, the detection of the intensity characteristics of the plurality of differently amplitude changed transformed wavefronts may be performed by a detector comprising only a single detection pixel or several detection pixels. Additionally, the output indicating at least one and possibly both of the phase and amplitude of the wavefront being analyzed may be provided by computer 2136 in a straight-forward manner.

In accordance with an embodiment of the present invention, the plurality of different amplitude changes 2110, 2112 and 2114, preferably spatial amplitude changes, are effected by applying a time-varying spatial amplitude change to part of the transformed wavefront 2108.

In accordance with a preferred embodiment of the present invention, the plurality of different amplitude changes 2110, 2112 and 2114 are effected by applying a spatially uniform, time-varying spatial amplitude change to part of the transformed wavefront 2108.

In accordance with an embodiment of the present invention, each of the wavefront 2100 and the transformed wavefront 2108 comprises a plurality of different wavelength components. In such a case, the plurality of different spatial amplitude changes may be effected by applying an amplitude change to each of the plurality of different wavelength components of the transformed wavefront. It is appreciated that the amplitude changes may be spatially different or that the amplitude may be differently attenuated for each different wavelength component.

In accordance with another embodiment of the present invention, each of the wavefront 2100 and the transformed wavefront 2108 comprises a plurality of different polarization components. In such a case, the plurality of different spatial amplitude changes may be effected by applying an amplitude change to each of the plurality of different polarization components of the transformed wavefront. It is appreciated that the amplitude changes may be spatially different or that the amplitude may be differently attenuated for each different polarization component.

In accordance with another embodiment of the present invention, the transform 2106 applied to the wavefront 2100 is a Fourier transform, the plurality of different spatial amplitude changes comprise at least three different amplitude changes, effected by applying a spatially uniform, time-varying spatial amplitude attenuation to part of the transformed wavefront 2108, and the plurality of intensity maps 2130, 2132 and 2134 comprises at least three intensity maps. In such a case, employing the plurality of intensity maps to obtain an output indicating the amplitude and phase of the wavefront being analyzed preferably includes:

expressing the wavefront being analyzed 2100 as a first complex function which has an amplitude and phase identical to the amplitude and phase of the wavefront being analyzed;

expressing the plurality of intensity maps as a function of the first complex function and of a spatial function governing the spatially uniform, time-varying spatial amplitude change;

defining a second complex function, having an absolute value and a phase, as a convolution of the first complex function and of a Fourier transform of the spatial function governing the spatially uniform, time-varying spatial amplitude attenuation;

expressing each of the plurality of intensity maps as a third function of:
the amplitude of the wavefront being analyzed;
the absolute value of the second complex function;
a difference between the phase of the wavefront being analyzed and the phase of the second complex function; and a known amplitude attenuation produced by one of the at least three different amplitude changes, to each of which one of the at least three intensity maps corresponds;

solving the third function to obtain the amplitude of the wavefront being analyzed, the absolute value of the second complex function and the difference between the phase of the wavefront being analyzed and the phase of the second complex function;

solving the second complex function to obtain the phase of the second complex function; and obtaining the phase of the wavefront being analyzed by adding the phase of the second complex function to the difference between the phase of the wavefront being analyzed and the phase of the second complex function.

Reference is now made to FIG. 21B, which is a simplified partially schematic, partially block diagram illustration of a wavefront analysis system suitable for carrying out the functionality of FIG. 21A in accordance with a preferred embodiment of the present invention. As seen in FIG. 21B, a wavefront, here designated by reference numeral 2150 is focused, as by a lens 2152, onto an amplitude attenuator 2154, which is preferably located at the focal plane of lens 2152. The amplitude attenuator 2154 generates amplitude changes, such as amplitude attenuation, and may be, for example, a spatial light modulator or a series of different partially transparent objects.

A second lens 2156 is arranged so as to image wavefront 2150 onto a detector 2158, such as a CCD detector. Preferably the second lens 2156 is arranged such that the detector 2158 lies in its focal plane. The output of detector 2158 is preferably supplied to data storage and processing circuitry 2160, which preferably carries out functionality "C" described hereinabove with reference to FIG. 21A.

Reference is now made to FIG. 22, which is a simplified partially schematic, partially pictorial illustration of a system for surface mapping employing the functionality and structure of FIGS. 21A and 21B. As seen in FIG. 22, a beam of radiation, such as light or acoustic energy, is supplied from a radiation source 2200, optionally via a beam expander 2202, onto a beam splitter 2204, which reflects at least part of the radiation onto a surface 2206 to be inspected. The radiation reflected from the inspected surface, is a surface mapping wavefront, which has an amplitude and a phase, and which contains information about the surface 2206. At least part of the radiation incident on surface 2206 is reflected from the surface 2206 and transmitted via the beam splitter 2204 and focused via a focusing lens 2208 onto an amplitude attenuator 2210, which is preferably located at the image plane of radiation source 2200.

The amplitude attenuator 2210 may be, for example, a spatial light modulator or a series of different partially transparent non-spatially uniform objects. It is appreciated that amplitude attenuator 2210 can be configured such that a substantial part of the radiation focused thereonto is reflected therefrom. Alternatively the amplitude attenuator 2210 can be configured such that a substantial part of the radiation focused thereonto is transmitted therethrough.

A second lens 2212 is arranged so as to image surface 2206 onto a detector 2214, such as a CCD detector. Preferably the second lens 2212 is arranged such that the detector 2214 lies in its focal plane. The output of detector 2214, an example of which is a set of intensity maps designated by reference numeral 2215, is preferably supplied to data storage and processing circuitry 2216, which preferably carries out functionality "C" described hereinabove with reference to FIG. 21A, providing an output indicating at least one and possibly both of the phase and the amplitude of the surface mapping wavefront. This output is preferably further processed to obtain information about the surface 2206, such as geometrical variations and reflectivity of the surface.

In accordance with a preferred embodiment of the present invention, the beam of radiation supplied from radiation source 2200 has a narrow wavelength band about a given central wavelength, causing the phase of the radiation reflected from surface 2206 to be proportional to geometrical variations in the surface 2206, the proportion being an inverse linear function of the central wavelength of the radiation.

In accordance with an embodiment of the present invention, the beam of radiation supplied from radiation source 2200 has at least two narrow wavelength bands, each centered about a different wavelength, designated $\lambda_1, \ldots, \lambda_n$. In such a case, the radiation reflected from the surface 2206 has at least two wavelength components, each centered around a wavelength $\lambda_1, \ldots, \lambda_n$.

At least two indications of the phase of the surface mapping wavefront are obtained. Each such indication corresponds to a different wavelength component of the reflected radiation. These at least two indications may be subsequently combined to enable enhanced mapping of the surface 2206, by avoiding ambiguity in the mapping, known as $2\pi i$ ambiguity, when the value of the mapping at a given spatial location in the surface exceeds the value of the mapping at a different spatial location in the surface by the largest of the different wavelengths $\lambda_1, \ldots, \lambda_n$. A proper choice of the wavelengths $\lambda_1, \ldots, \lambda_n$, may lead to elimination of this ambiguity when the difference in values of the mapping at different locations is smaller than the multiplication product of all the wavelengths.

In accordance with a preferred embodiment of the present invention, the amplitude attenuator 2210 applies a plurality of different spatial amplitude changes to the radiation wavefront reflected from surface 2206 and Fourier transformed by lens 2208. Application of the plurality of different spatial amplitude changes provides a plurality of differently amplitude changed transformed wavefronts which may be subsequently detected by detector 2214.

In accordance with yet another preferred embodiment of the present invention, at least three different spatial amplitude changes are applied by amplitude attenuator 2210, resulting in at least three different intensity maps 2215. The at least three intensity maps are employed by the data storage and processing circuitry 2216 to obtain an output indicating at least one and possibly both of the phase and amplitude of the surface mapping wavefront. In such a case, the data storage and processing circuitry 2216, carries out functionality "C" described hereinabove with reference to FIG. 21A, where the wavefront being analyzed (FIG. 21A) is the surface mapping wavefront.

Additionally, in accordance with a preferred embodiment of the present invention, the beam of radiation supplied from radiation source 2200 comprises a plurality of different wavelength components, thereby providing a plurality of wavelength components in the surface mapping wavefront and subsequently in the transformed wavefront impinging on amplitude attenuator 2210. In this case the amplitude attenuator may be an object, at least one of whose reflection and transmission varies spatially. This spatial variance of the amplitude attenuator generates a different spatial amplitude change for each of the wavelength components, thereby providing a plurality of differently amplitude changed transformed wavefronts to be subsequently detected by detector 2214. It is appreciated that the amplitude attenuation generated by attenuator 2210 may be different for each of the different wavelength components.

In accordance with an embodiment of the present invention, the surface 2206 is a surface of media in which information is encoded by selecting the height of the media at each of a multiplicity of different locations on the media. In such a case, the indications of the amplitude and phase of the surface mapping wavefront provided by data storage and processing circuitry 2216 are employed to obtain the information encoded on the media.

It is appreciated that other applications, such as those described hereinabove with respect to FIGS. 16-20 may also be provided in accordance with the present invention wherein amplitude attenuation is performed instead of phase manipulation. It is further appreciated that all of the applications described hereinabove with reference to FIGS. 15-20 may also be provided in accordance with the present invention wherein both amplitude attenuation and phase manipulation are performed.

It will be appreciated by persons skilled in the art that the present invention is not limited by what has been particularly shown and described hereinabove. Rather the present invention includes both combinations and subcombinations of features described hereinabove as well as modifications and variations of such features which would occur to a person of ordinary skill in the art upon reading the foregoing description and which are not in the prior art.

The invention claimed is:

1. A method of wavefront analysis comprising:
utilizing a light source to illuminate an object and to generate a wavefront being analyzed having an amplitude and a phase;
applying a transform to said wavefront being analyzed, thereby to obtain a transformed wavefront;
applying a plurality of different phase changes by applying a spatially uniform time-varying spatial phase change to said transformed wavefront, thereby to obtain a plurality of differently phase changed transformed wavefronts;
obtaining a plurality of intensity maps of said plurality of differently phase changed transformed wavefronts;
employing said plurality of intensity maps to obtain an output indicating said amplitude and phase of said wavefront being analyzed;
wherein said transformed wavefront includes a non spatially modulated region representing an image of said light source, and a spatially modulated region and wherein said phase changes are applied to said spatially modulated region.

2. An apparatus for wavefront analysis comprising:
a light source to illuminate an object and to generate a wavefront being analyzed having an amplitude and a phase;
a wavefront transformer operating to transform said wavefront being analyzed, thereby to obtain a transformed wavefront, and to apply a plurality of different phase changes by applying a spatially uniform time-varying spatial phase change to said transformed wavefront, thereby to obtain a plurality of differently phase changed transformed wavefronts;
an intensity map generator operating to provide a plurality of intensity maps of said plurality of phase changed transformed wavefronts;
an intensity map utilizer, employing the plurality of intensity maps for providing an output indicating the amplitude and phase of the wavefront being analyzed; wherein said transformed wavefront includes a non spatially modulated region representing an image of said light source, and a spatially modulated region and wherein said spatial phase changes are applied to said spatially modulated region.

3. A method of wavefront analysis comprising:
applying a transform to a wavefront being analyzed which has an amplitude and a phase, thereby to obtain a transformed wavefront;
obtaining a plurality of differently phase changed transformed wavefronts by splitting the transformed wavefront into several wavefronts, and applying spatial phase changes to each of said several wavefronts;
obtaining a plurality of intensity maps of said plurality of differently phase changed transformed wavefronts;
employing said plurality of intensity maps to obtain an output indicating said amplitude and phase of said wavefront being analyzed;
wherein each of said spatial phase changes is generated by a different transparent, spatially non-uniform object.

4. An apparatus for wavefront analysis comprising:
a wavefront transformer operating to transform said wavefront being analyzed, thereby to obtain a transformed wavefront and to apply a plurality of different phase changes by splitting the transformed wavefront into several wavefronts, and applying spatial phase changes to each of said several wavefronts;
an intensity map generator operating to provide a plurality of intensity maps of said plurality of differently phase changed transformed wavefronts;
an intensity map utilizer, employing said plurality of intensity maps for providing an output indicating the amplitude and phase of the wavefront being analyzed. wherein each of said spatial phase changes is generated by a different transparent, spatially non-uniform object.

5. A method of wavefront analysis comprising:
transmitting a wavefront being analyzed, which has an amplitude and a phase, through an imaging system to obtain an imaged wavefront, having amplitude and phase proportional to said amplitude and phase of said wavefront being analyzed;
obtaining a plurality of differently phase changed transformed wavefronts corresponding to said imaged wavefront;
obtaining a plurality of intensity maps of said plurality of phase changed transformed wavefronts;
and employing said plurality of intensity maps to obtain an output indicating said amplitude and phase of said wavefront being analyzed.

6. An apparatus for wavefront analysis comprising:
an imaging system, providing an imaged wavefront having amplitude and phase, proportional to amplitude and phase of a wavefront being analyzed;
a wavefront transformer operating to provide a plurality of differently phase changed transformed wavefronts corresponding to the imaged wavefront;
an intensity map generator operating to provide a plurality of intensity maps of said plurality of phase changed transformed wavefronts;
an intensity map utilizer, employing the plurality of intensity maps for providing an output indicating the amplitude and phase of the wavefront being analyzed.

* * * * *